(12) United States Patent
Kim et al.

(10) Patent No.: US 11,891,446 B2
(45) Date of Patent: Feb. 6, 2024

(54) HIGHLY POTENT ANTIBODIES BINDING TO DEATH RECEPTOR 5

(71) Applicant: GALAXY BIOTECH, LLC, Cupertino, CA (US)

(72) Inventors: Kyung Jin Kim, Cupertino, CA (US); Hangil Park, San Francisco, CA (US); Lihong Wang, Hayward, CA (US); Yi Ding, Milpitas, CA (US); April Zhang, San Jose, CA (US); Maximiliano Vasquez, Palo Alto, CA (US)

(73) Assignee: GALAXY BIOTECH, LLC, Cupertino, CA (US)

(*) Notice: Subject to any disclaimer, the term of this patent is extended or adjusted under 35 U.S.C. 154(b) by 362 days.

(21) Appl. No.: 17/165,818

(22) Filed: Feb. 2, 2021

(65) Prior Publication Data
US 2021/0238297 A1 Aug. 5, 2021

Related U.S. Application Data

(62) Division of application No. 15/772,014, filed as application No. PCT/US2016/059517 on Oct. 28, 2016, now Pat. No. 10,941,204.

(Continued)

(51) Int. Cl.
*A61K 39/395* (2006.01)
*C07K 16/28* (2006.01)
(Continued)

(52) U.S. Cl.
CPC .. *C07K 16/2878* (2013.01); *A61K 39/001117* (2018.08); *A61P 35/00* (2018.01); *A61K 2039/505* (2013.01); *C07K 2317/24* (2013.01); *C07K 2317/31* (2013.01); *C07K 2317/72* (2013.01); *C07K 2317/73* (2013.01); *C07K 2317/75* (2013.01); *C07K 2317/76* (2013.01)

(58) Field of Classification Search
None
See application file for complete search history.

(56) References Cited

U.S. PATENT DOCUMENTS 7,744,881 B2 6/2010 Chuntharapai et al.
7,807,153 B2* 10/2010 Adams ............... A61P 35/00
424/139.1

(Continued)

FOREIGN PATENT DOCUMENTS

FR 2967676 B1 9/2014
JP 2005-517021 A 6/2005
(Continued)

OTHER PUBLICATIONS

Dubuisson et al., Antibodies and Derivatives Targeting DR4 and DR5 for Cancer Therapy, Antibodies, 6:16, 31 pages, doi:10.3390/antib6040016, Oct. 2017.*

(Continued)

*Primary Examiner* — Claire Kaufman
(74) *Attorney, Agent, or Firm* — Alston & Bird LLP

(57) ABSTRACT

The present invention is directed toward monoclonal antibodies that bind to death receptor 4 and/or death receptor 5, a pharmaceutical composition comprising same, and methods of treatment comprising administering such a pharmaceutical composition to a patient.

11 Claims, 29 Drawing Sheets

Specification includes a Sequence Listing.

Related U.S. Application Data

(60) Provisional application No. 62/248,782, filed on Oct. 30, 2015.

(51) Int. Cl.
*A61K 39/00* (2006.01)
*A61P 35/00* (2006.01)

(56) References Cited

U.S. PATENT DOCUMENTS

| | | | |
|---|---|---|---|
| 8,409,570 B2 * | 4/2013 | Adams | C07K 16/2878 |
| | | | 424/139.1 |
| 9,120,855 B2 * | 9/2015 | Cromie | A61P 13/12 |
| 9,725,517 B2 * | 8/2017 | Zheng | A61P 35/00 |
| 10,501,552 B2 * | 12/2019 | Moore | C07K 16/30 |
| 10,633,440 B2 * | 4/2020 | Bonvini | C07K 16/283 |
| 10,941,204 B2 | 3/2021 | Kim et al. | |
| 2004/0120947 A1 | 6/2004 | Ashkenazi et al. | |
| 2005/0265998 A1 | 12/2005 | Elson | |
| 2014/0093504 A1 | 4/2014 | Hu et al. | |
| 2014/0271648 A1 | 9/2014 | Chi et al. | |

FOREIGN PATENT DOCUMENTS

| | | |
|---|---|---|
| WO | WO 2003/066661 A2 | 8/2003 |
| WO | WO 2017/075484 A2 | 5/2017 |

OTHER PUBLICATIONS

U.S. Appl. No. 62/248,789, filed Oct. 30, 2015, Expired.
U.S. Appl. No. 62/248,782, filed Oct. 30, 2015, Expired.
PCT/US2016/059517, Oct. 28, 2016, WO 2017/075484, Expired.
U.S. Appl. No. 15/772,014, filed Apr. 27, 2018, U.S. Pat. No. 10,941,204, Issued.
PCT/US2016/059517 International Search Report and Written Opinion dated Apr. 25, 2017.
PCT/US2016/059517 International Preliminary Report on Patentability dated May 1, 2018.
PCT/US2016/059517 Invitation of Pay Additional Fees and, Where Applicable, Protest Fees dated Feb. 23, 2017.
EP 16860964.2 Extended European Search Report dated Jul. 31, 2019.
Mimoto, et al., "Engineered antibody Fc variant with selectively enhanced FcγRIIb binding over both FcγRIIa$^{R131}$ and FcγRIIa$^{H131}$," Protein Engineering, Design & Selection, vol. 26, No. 10, pp. 589-598, (2013).
U.S. Appl. No. 15/772,014 Notice of Allowance dated Nov. 2, 2020.
U.S. Appl. No. 15/772,014 Non-Final Office Action dated Jun. 10, 2020.
U.S. Appl. No. 15/772,014 Restriction Requirement dated Feb. 13, 2020.
EP 16860964.2 Supplementary Partial European Search Report dated Apr. 26, 2019.

* cited by examiner

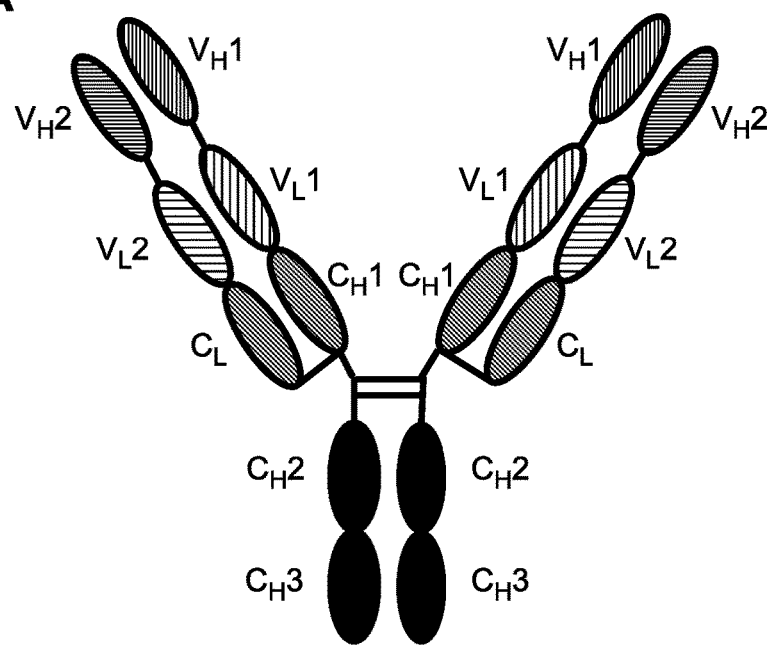
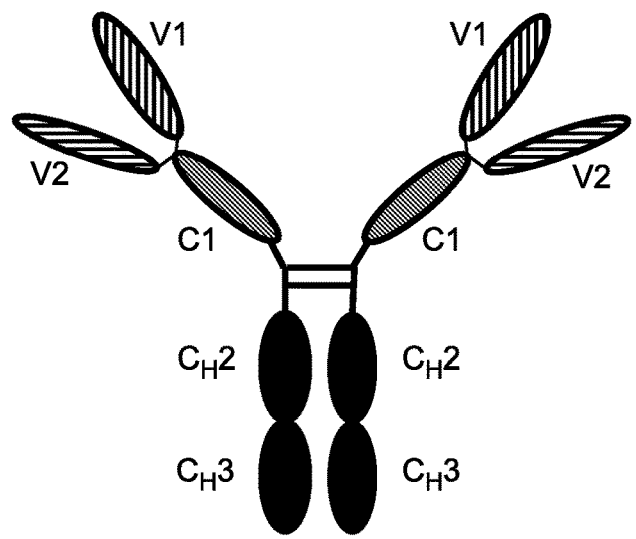
Figures 1A, B

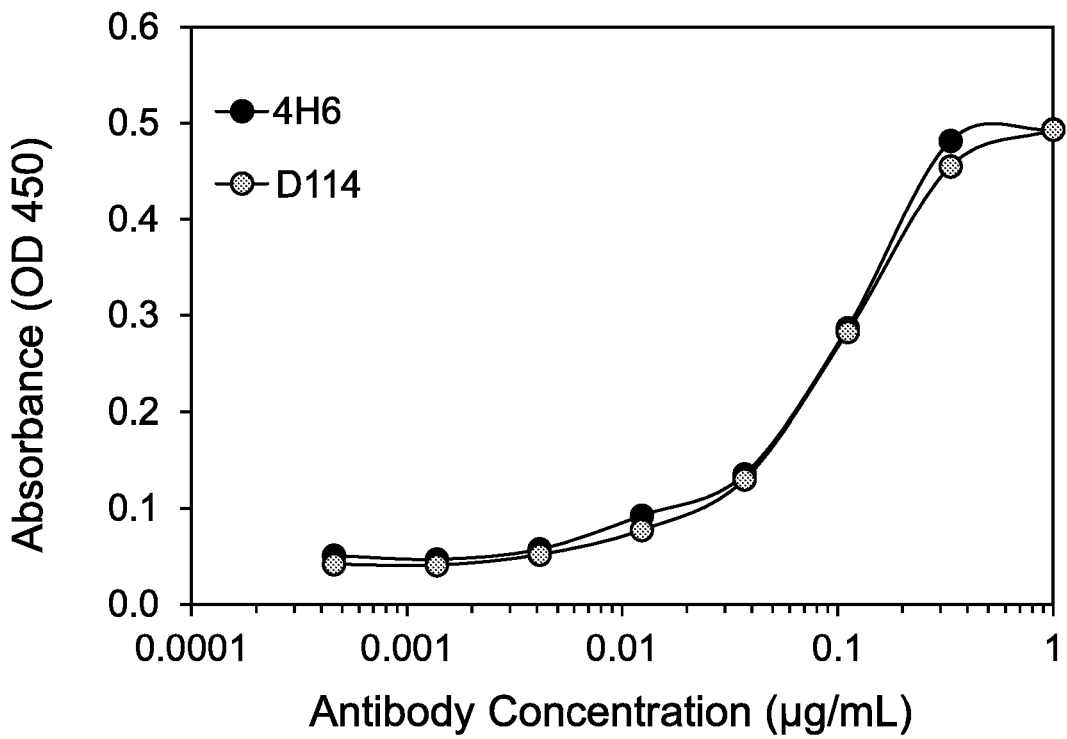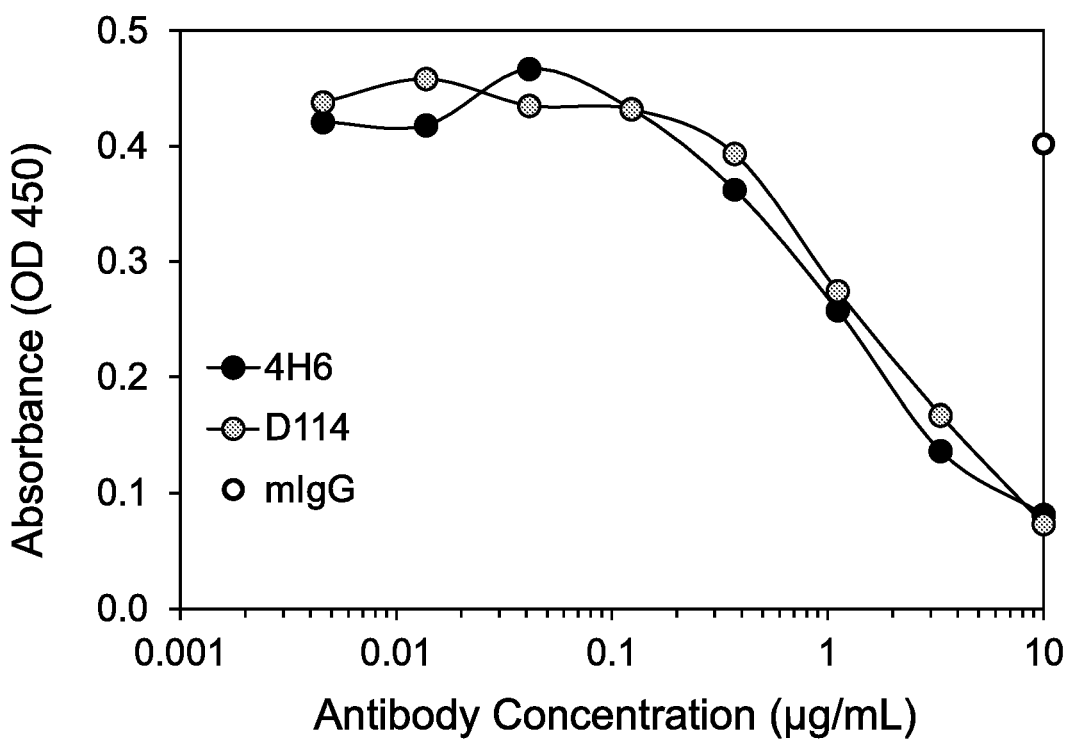
Figures 2A, B

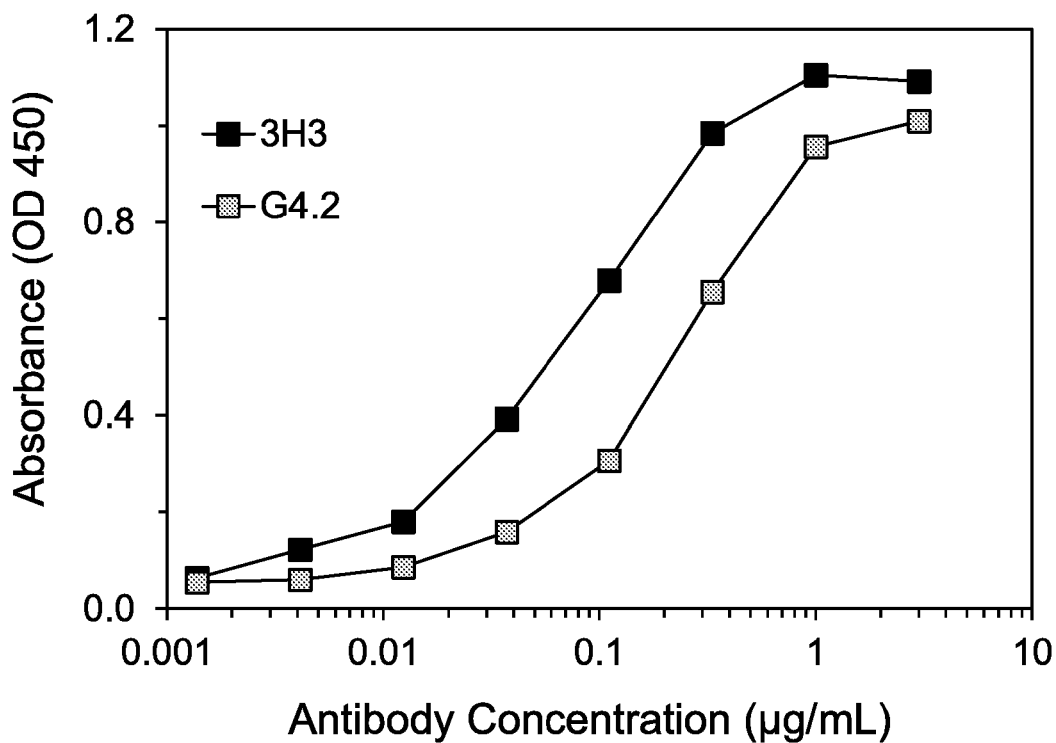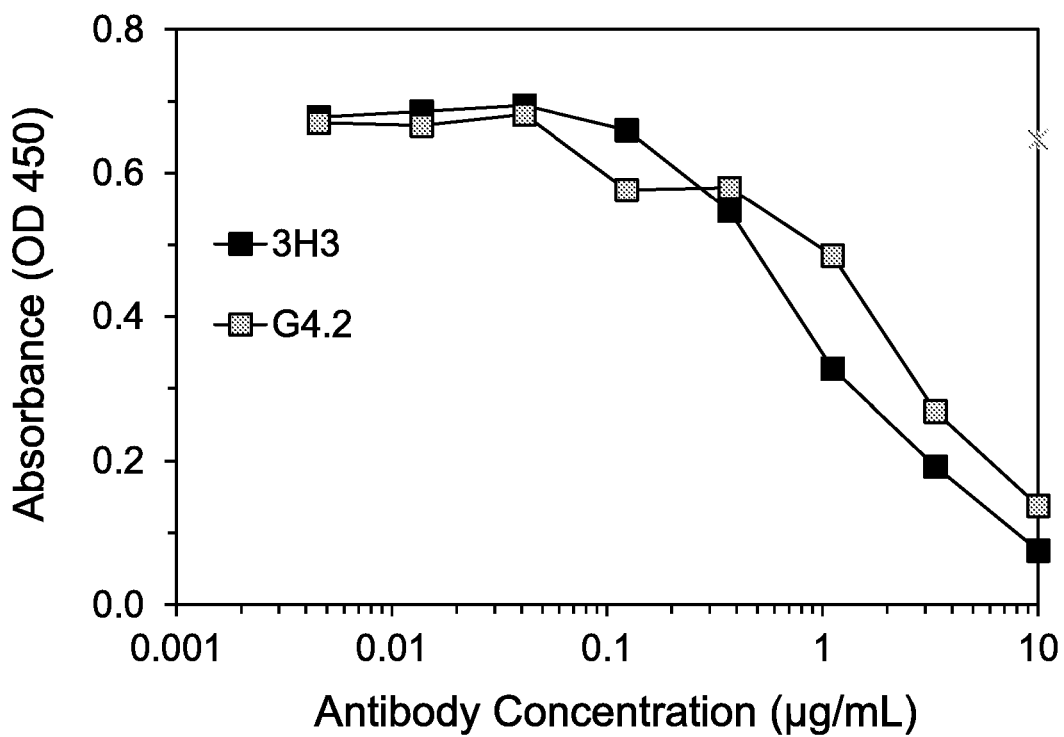
Figures 2C, D

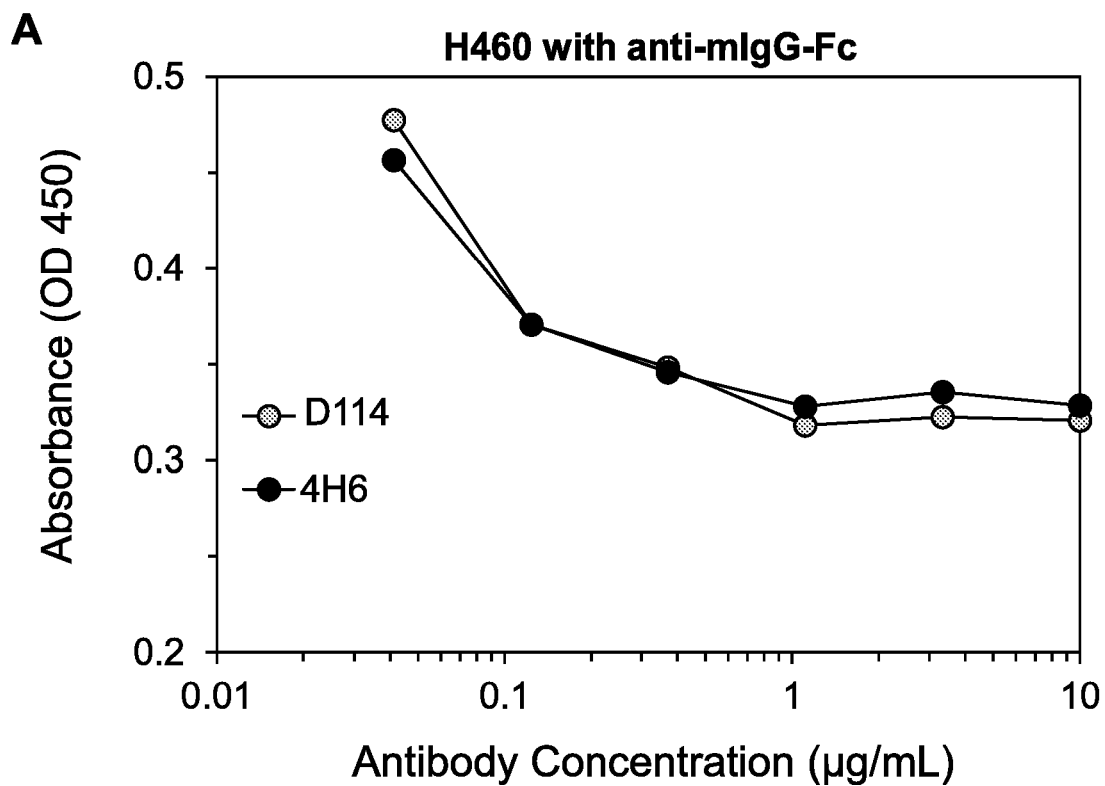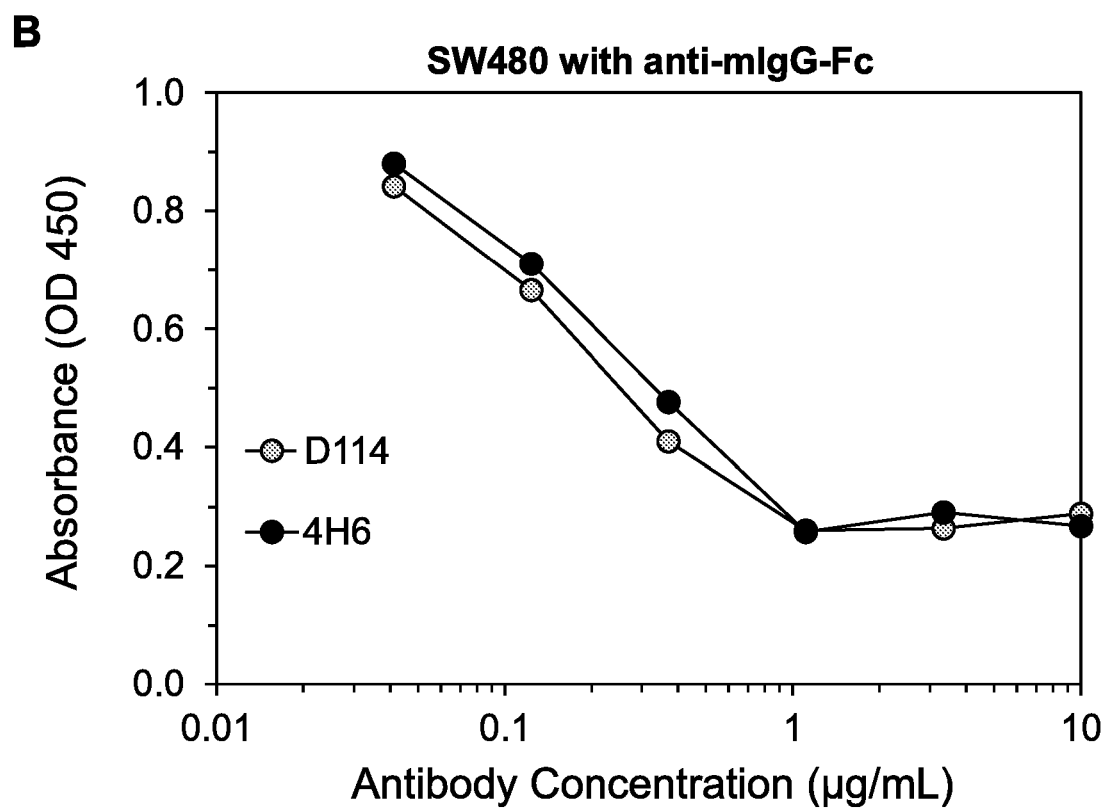
Figures 3A, B

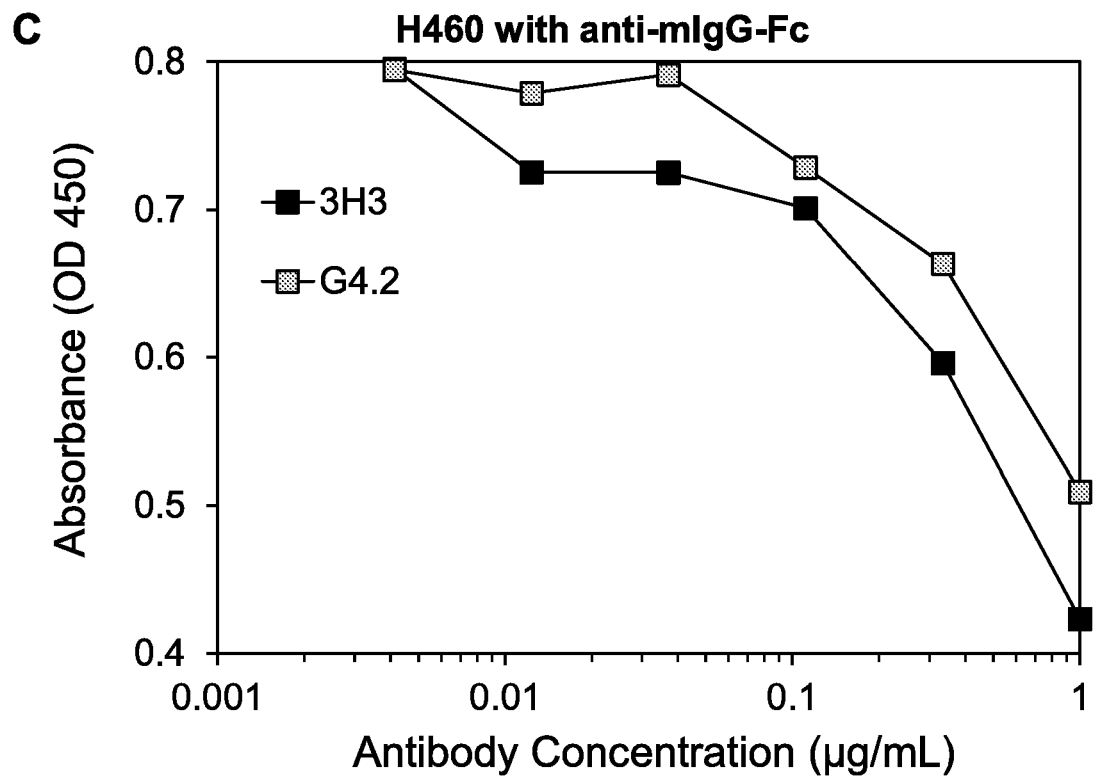
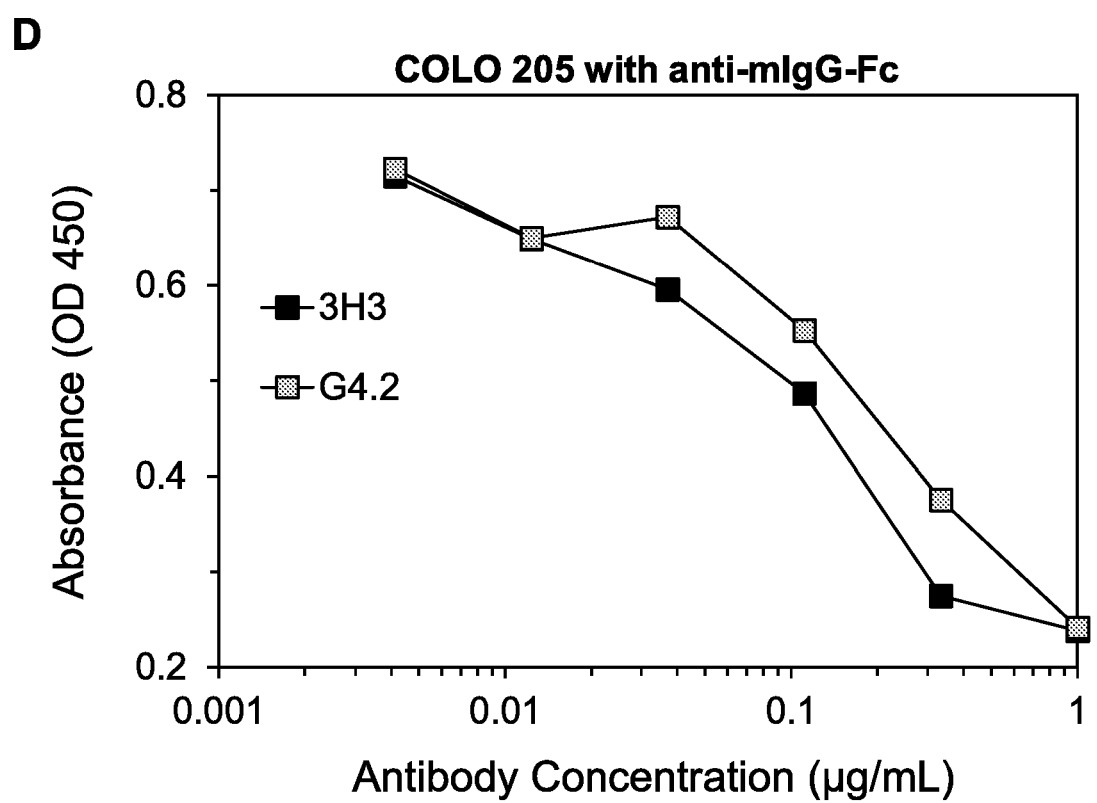
Figures 3C, D

A

4H6 V$_H$

QVQLKESGPGLVAPSQSLSITCTVSGFSLTSYGVHWVRQPPGKGLEWLGVIWAVGSTNYN

SALMSRLSISKDNSKSQVFLKMNSLQTDDTAMYYCAREGEFDYYGSSLLSYHSMNFWGQG

TSVTVSS

B

4H6 V$_L$

DIQMTQTTSSLSASLGDRVTISCRASQDISNYLNWYQRKPDGTVKLLIYYTSRLHSGVPS

RFSGSGSGTDYSLTISNLEQEDIATYFCQQGNTLPFTFGSGTKLEIK

C

3H3 V$_H$

EVQLQQSGPELVKPGASVKMSCKASGYTFTSYVMHWVKQKPGQGLEWIGYIIPYNDGTKY

NEKFKGKATLTSDKSSSTAYMELSRLTSEDSAVYYCARGGINYDYLYYFDYWGQGTTLTV

SS

D

3H3 V$_L$

DVVMTQIPLSLPVSLGDQASISCRSSQSLVHSNGNTYLHWYLQKPGQSPKLLIYKVSNRF

SGVPDRFSGSGSGTDFTLKISRVEAEDLGVYFCSQSTHVPHTFGGGTKLEIK

```
                        1          2          3          4
               1234567890 1234567890 1234567890 1234567890
D114           DIQMTQTTSS LSASLGDRVT ISCSASQDIT NYLNWYQQKP
HuD114-L1      DIQMTQSPSS LSASVGDRVT ITCSASQDIT NYLNWYQQKP
AIT38746       DIQMTQSPSS LSASVGDRVT ITCQASQDIS NYLNWYQQKP 5          6          7          8
               1234567890 1234567890 1234567890 1234567890
D114           DGTIKLLVYY TSSLHSGVPS RFSGSGSGTD YSLTISNLEP
HuD114-L1      GKAPKLLVYY TSSLHSGVPS RFSGSGSGTD YTFTISSLQP
AIT38746       GKAPKLLIYD ASNLETGVPS RFSGSGSGTD FTFTISSLQP 9         10
               1234567890 1234567890 1234567
D114           EDIATYYCHQ YSKLPWTFGG GTSLEIK
HuD114-L1      EDIATYYCHQ YSKLPWTFGQ GTKVEIK
AIT38746       EDIATYYCQQ YDNLTWTFGQ GTKVEIK
```

B

```
                        1          2          3          4
               1234567890 1234567890 1234567890 1234567890
D114           QIQLQQSGPE LMKPGSSVKI SCKASGYTFT NYYINWVKQR
HuD114-H1      QVQLVQSGAE VKKPGASVKV SCKASGYTFT NYYINWVRQA
HuD114-H2      QVQLVQSGAE VKKPGASVKV SCKASGYTFT NYYINWVRQA
AAC18293       QVQLVQSGAE VKKPGASVKV SCKASGYTFT GYYMHWVRQA 5          a          6           7          8
               1234567890 12234567890 1234567890 1234567890
D114           PGQGLEWLGW IYPGIGDIKYN EKFKGRATLT ADTSSNTAYM
HuD114-H1      PGQGLEWLGW IYPGIGDIKYN EKFKGRVTMT ADTSISTAYM
HuD114-H2      PGQGLEWLGW IYPGIGDIKYN EKFKGRATLT ADTSISTAYM
AAC18293       PGQGLEWMGW INPNSGGTNYA QKFQGRVTMT RDTSISTAYM abc         9         10a         11
               1222234567890 1234567890 1234567890123
D114           QLNRLTSDDTGVY FCARSGWAWF- VDWGQGTLVSVSS
HuD114-H1      ELSRLRSDDTAVY YCARSGWAWF- VDWGQGTLVTVSS
HuD114-H2      ELSRLRSDDTAVY YCARSGWAWF- VDWGQGTLVTVSS
AAC18293       ELSRLRSDDTAVY YCARTAGAAYF DYWGQGTLVTVSS
```

```
                         1          2          abcdef  3          4
              1234567890 1234567890 1234567777777890 1234567890
G4.2          NIVLTQSPAS LAVSLGQRAT MSCRASESVDI--YGN SFMHWYQQKP
HuG4.2-L1     DIVLTQSPDS LAVSLGERAT INCRASESVDI--YGN SFMHWYQQKP
HuG4.2-L2     NIVLTQSPDS LAVSLGERAT INCRASESVDI--YGN SFMHWYQQKP
AAQ02698      DIVMTQSPDS LAVSLGERAT INCKSSQSVLYSSNNK NYLAWYQQKP 5          6          7          8
              1234567890 1234567890 1234567890 1234567890
G4.2          GQPPKLLIYL SSNLESGVPA RFSGSGSRTD FTLTIDPVEA
HuG4.2-L1     GQPPKLLIYL SSNLESGVPD RFSGSGSRTD FTLTISSLQA
HuG4.2-L2     GQPPKLLIYL SSNLESGVPD RFSGSGSRTD FTLTISSLQA
AAQ02698      GQPPKLLIYW ASTRESGVPD RFSGSGSGTD FTLTISSLQA 9          10         11
              1234567890 1234567890 1234567
G4.2          DDAATYYCQQ SYEDPLTFGA GTKLDLK
HuG4.2-L1     EDVAVYYCQQ SYEDPLTFGG GTKVEIK
HuG4.2-L2     EDVAVYYCQQ SYEDPLTFGG GTKVEIK
AAQ02698      EDVAVYYCQQ YYSTPLTFGG GTKVEIK
```

D

```
                         1          2          3          4
              1234567890 1234567890 1234567890 1234567890
G4.2          DVKLVESGGG LVKLGGSLKL SCAASGLPFN SYYMSWVRQT
HuG4.2-H1     EVQLVESGGG LVQPGGSLRL SCAASGLPFN SYYMSWVRQA
HuG4.2-H2     EVQLVESGGG LVQPGGSLRL SCAASGLPFN SYYMSWVRQA
AAC50998      EVQLVESGGG LVQPGGSLRL SCAASGFTFS SYWMSWVRQA 5          a    6          7          8
              1234567890 12234567890 1234567890 1234567890
G4.2          PEKRLELVAA INSNGGRIHYP DTVKGRFTIS RDNAKNTLYL
HuG.4.2-H1    PGKGLEWVAA INSNGGRIHYP DTVKGRFTIS RDNAKNSLYL
HuG.4.2-H2    PGKGLELVAA INSNGGRIHYP DTVKGRFTIS RDNAKNSLYL
AAC50998      PGKGLEWVAN IKQDGSEKYYV DSVKGRFTIS RDNAKNSLYL abc    9          10abcd      11
              1222234567890 12345678900000 1234567890123
G4.2          QMSSLKSEDTALY YCTRLTYYGNPAWF AYWGQGTLVTVSA
HuG4.2-H1     QMNSLRAEDTAVY YCTRLTYYGNPAWF AYWGQGTLVTVSS
HuG4.2-H2     QMNSLRAEDTAVY YCTRLTYYGNPAWF AYWGQGTLVTVSS
AAC50998      QMNSLRAEDTAVY YCARGSSDM----- DYWGQGTLVTVSS
```

B-4H6/3H3-hFc heavy chain**

~~MEFGLSWVFLVALLRGVQC~~QVQLKESGPGLVAPSQSLSITCTVSGFSLTSYGVHWVRQPP

GKGLEWLGVIWAVGSTNYNSALMSRLSISKDNSKSQVFLKMNSLQTDDTAMYYCAREGEF

DYYGSSLLSYHSMNFWGQGTSVTVSSASGSGGGGSGGGGSGGGGSDIQMTQTTSSLSASL

GDRVTISCRASQDISNYLNWYQRKPDGTVKLLIYYTSRLHSGVPSRFSGSGSGTDYSLTI

SNLEQEDIATYFCQQGNTLPFTFGSGTKLEIKSSASTKGPSVFPLAPSSKSTSGGTAALG

CLVKDYFPEPVTVSWNSGALTSGVHTFPAVLQSSGLYSLSSVVTVPSSSLGTQTYICNVN

HKPSNTKVDKRVEPKSCDKTHTCPPCPAPELLGGPSVFLFPPKPKDTLMISRTPEVTCVV

VDVEHEDPEVKFNWYVDGVEVHNAKTKPREEQYNSTYRVVSVLTVLHQDWLNGKEYKCKV

SNKAFPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKSLSL

SPGK

B

B-4H6/3H3-hFc light chain**

~~MEWSWIFLFLLSGTAGVHS~~EVQLQQSGPELVKPGASVKMSCKASGYTFTSYVMHWVKQKP

GQGLEWIGYIIPYNDGTKYNEKFKGKATLTSDKSSSTAYMELSRLTSEDSAVYYCARGGI

NYDYLYYFDYWGQGTTLTVSSASGSGGGGSGGGGSGGGGSDVVMTQIPLSLPVSLGDQAS

ISCRSSQSLVHSNGNTYLHWYLQKPGQSPKLLIYKVSNRFSGVPDRFSGSGSGTDFTLKI

SRVEAEDLGVYFCSQSTHVPHTFGGGTKLEIKRTVAAPSVFIFPPSDEQLKSGTASVVCL

LNNFYPREAKVQWKVDNALQSGNSQESVTEQDSKDSTYSLSSTLTLSKADYEKHKVYACE

VTHQGLSSPVTKSFNRGEC

Figures 6A, B

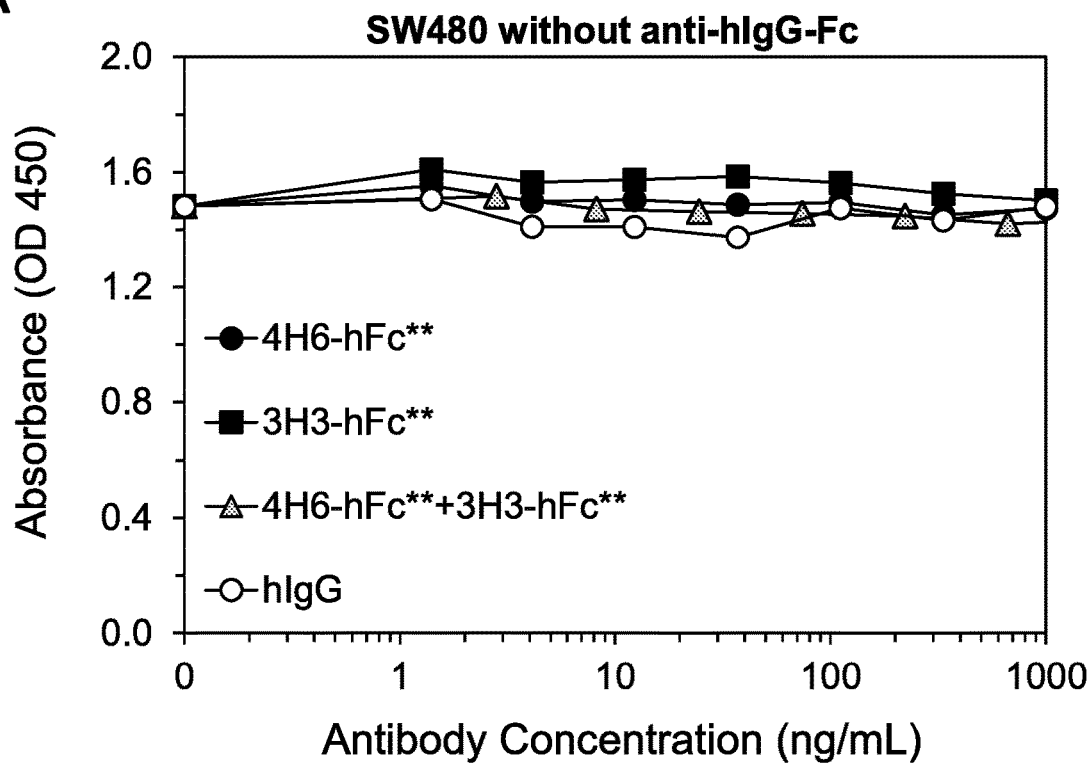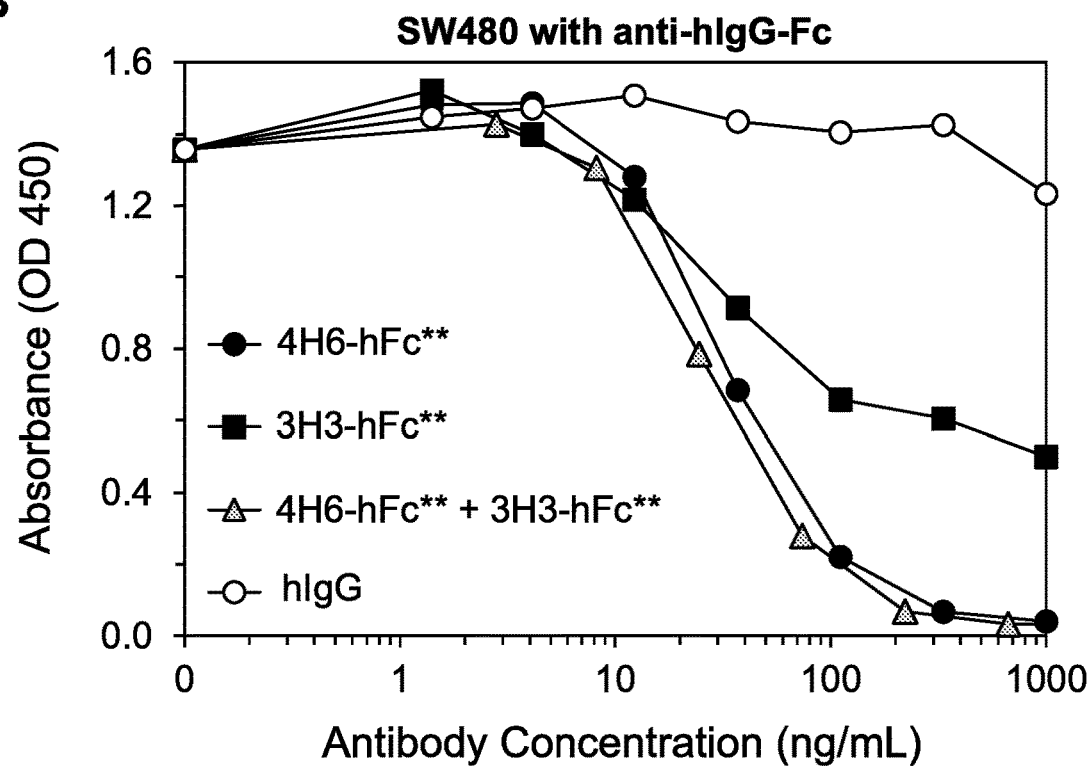
Figures 7A, B

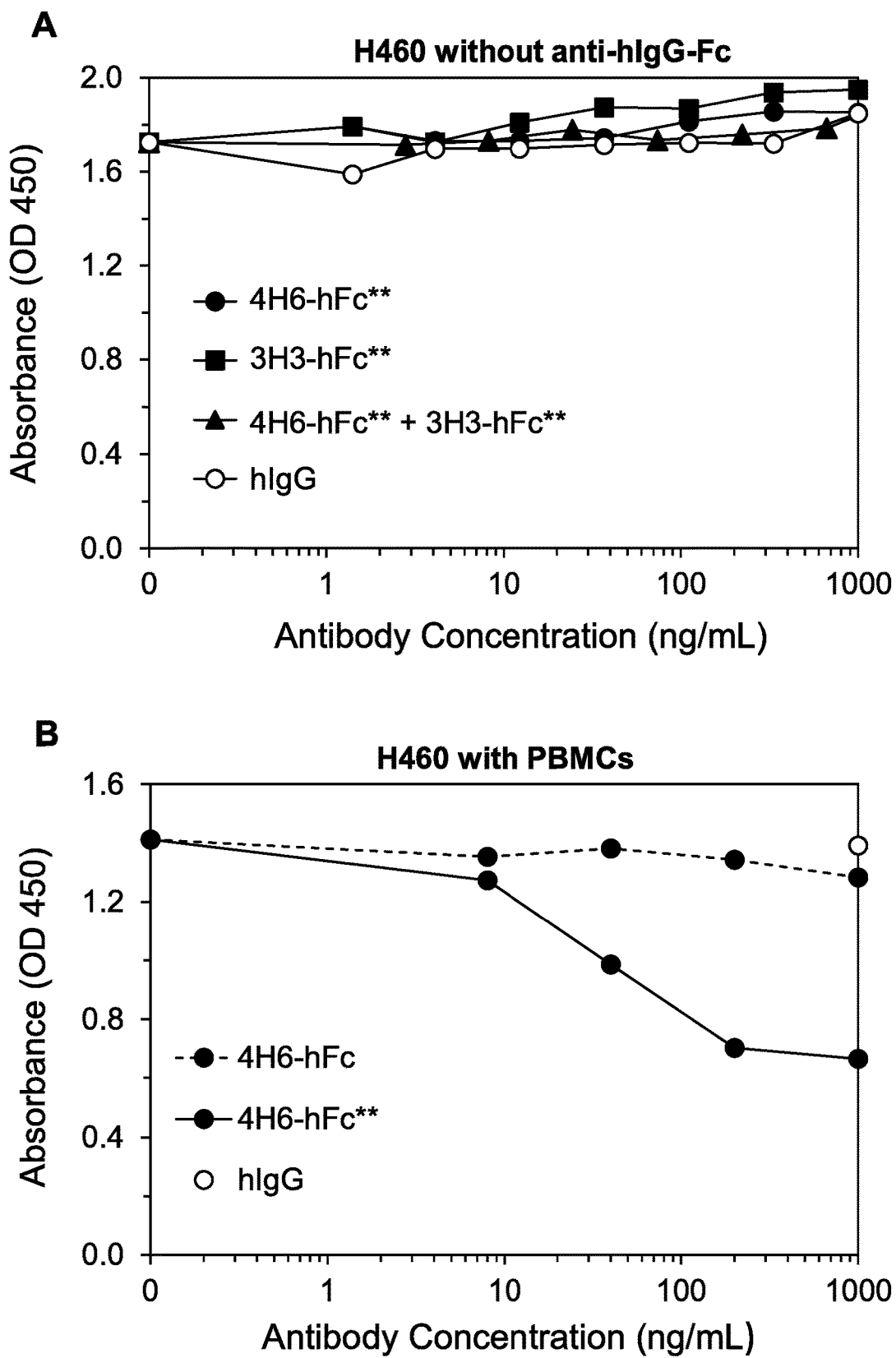
Figures 8A, B

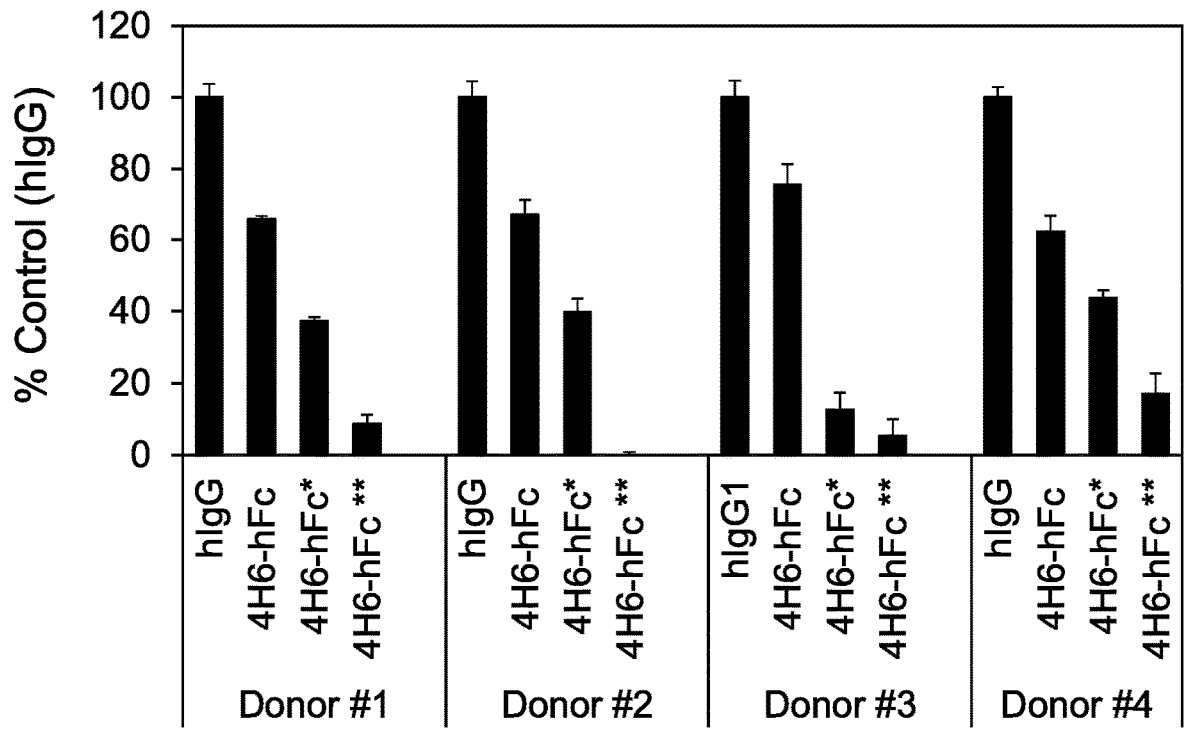
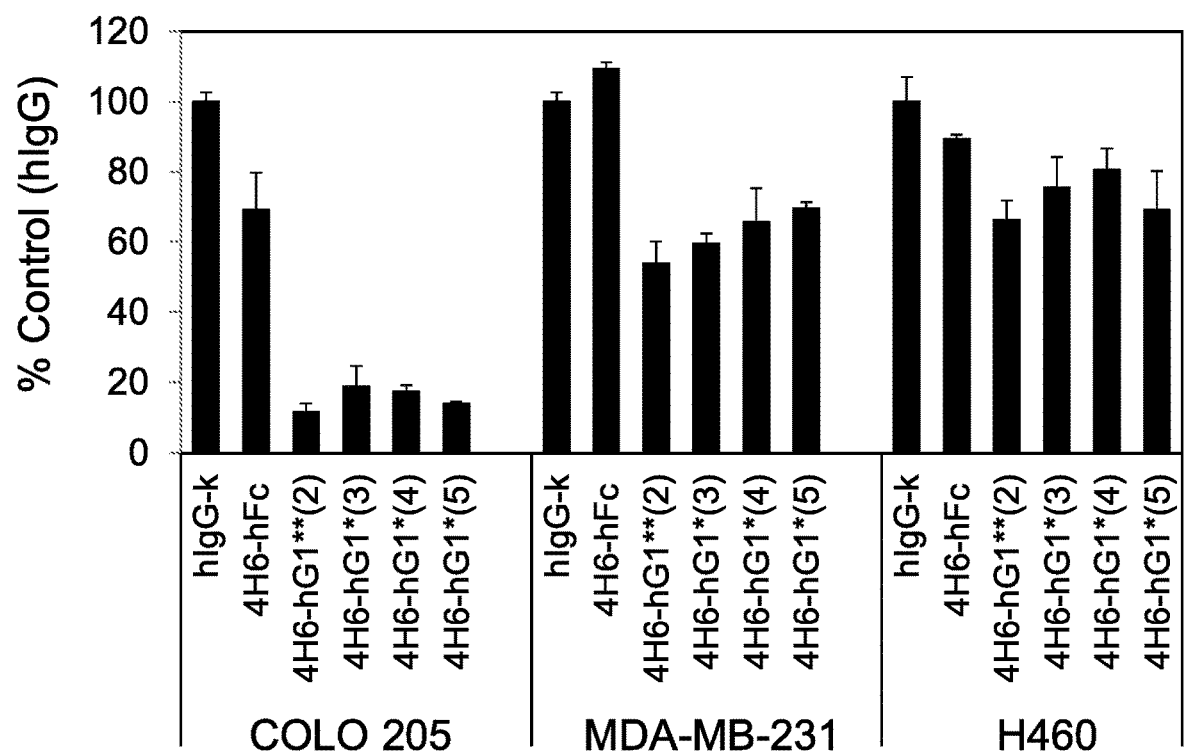
Figures 9A, B

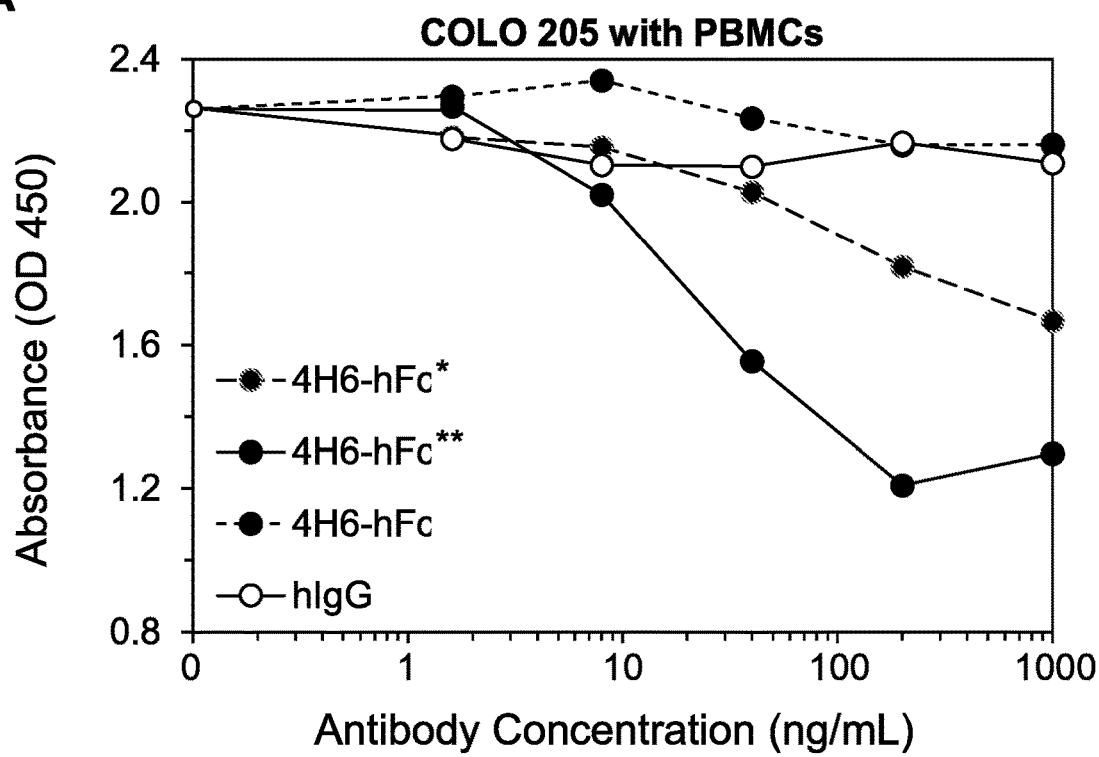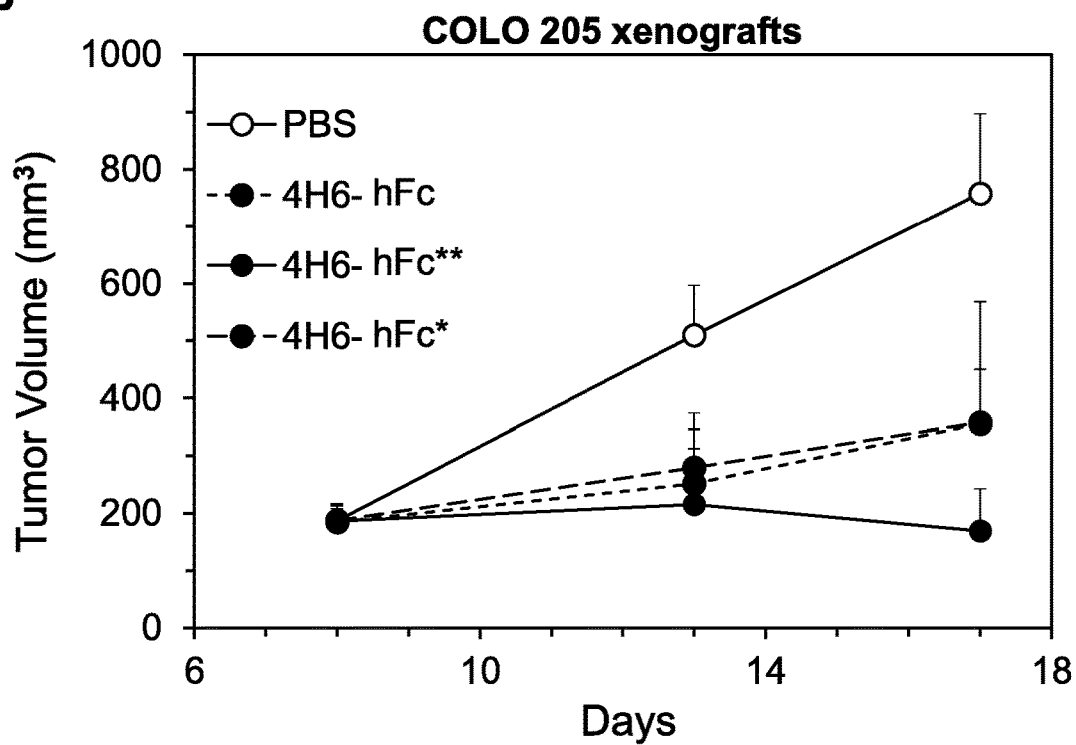
Figures 10A, B

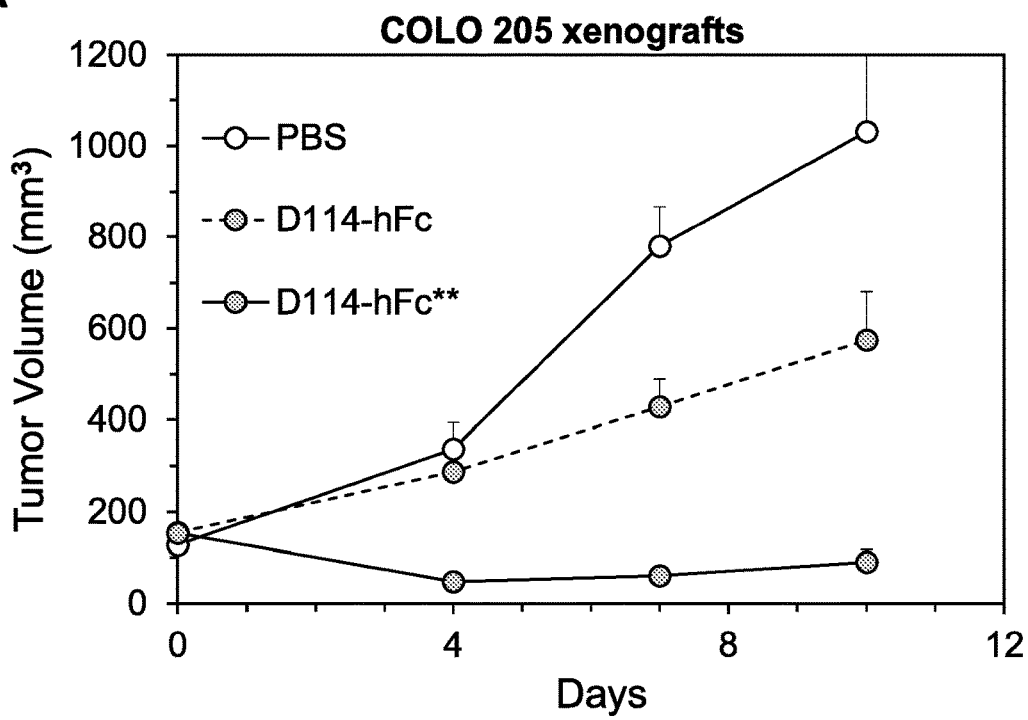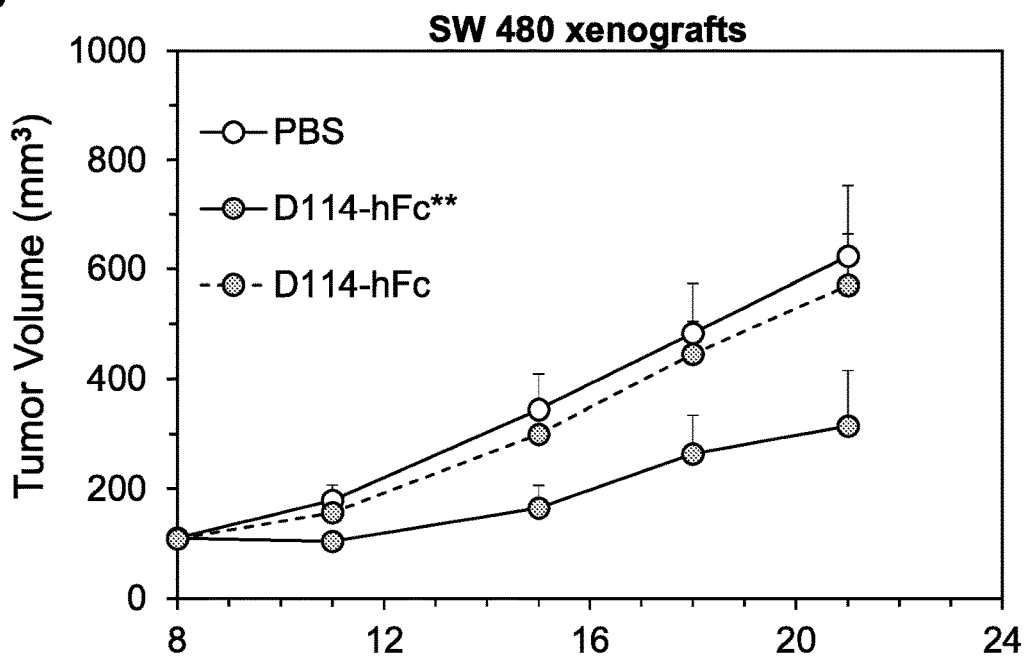
Figures 11A, B

C

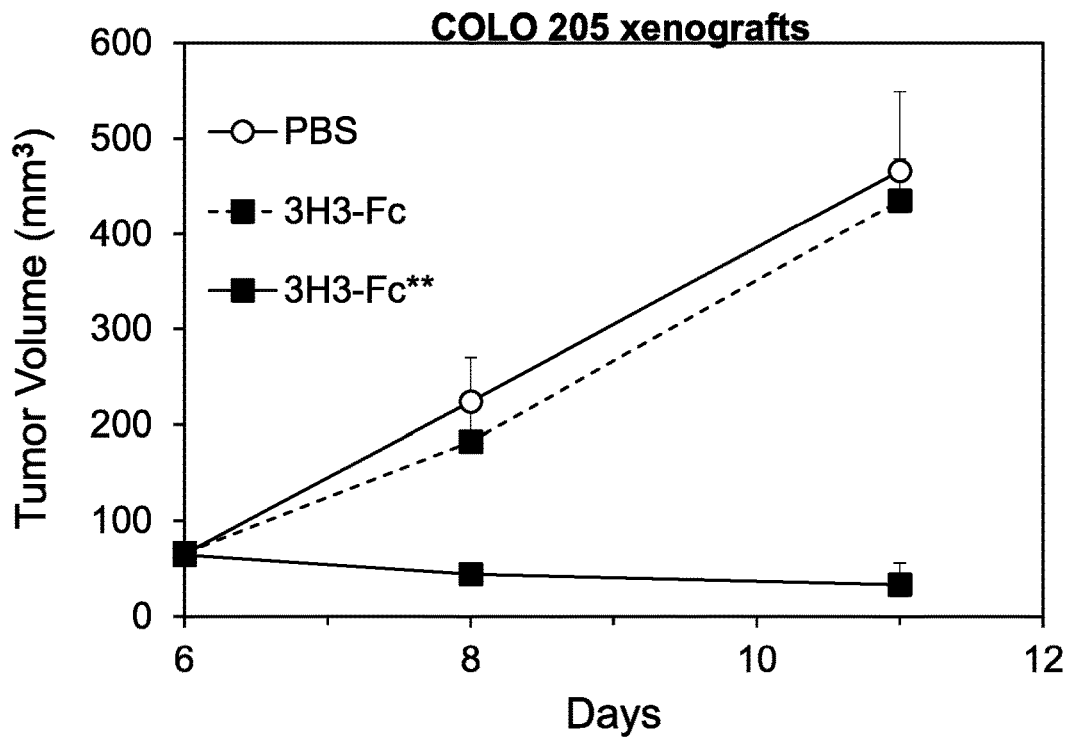
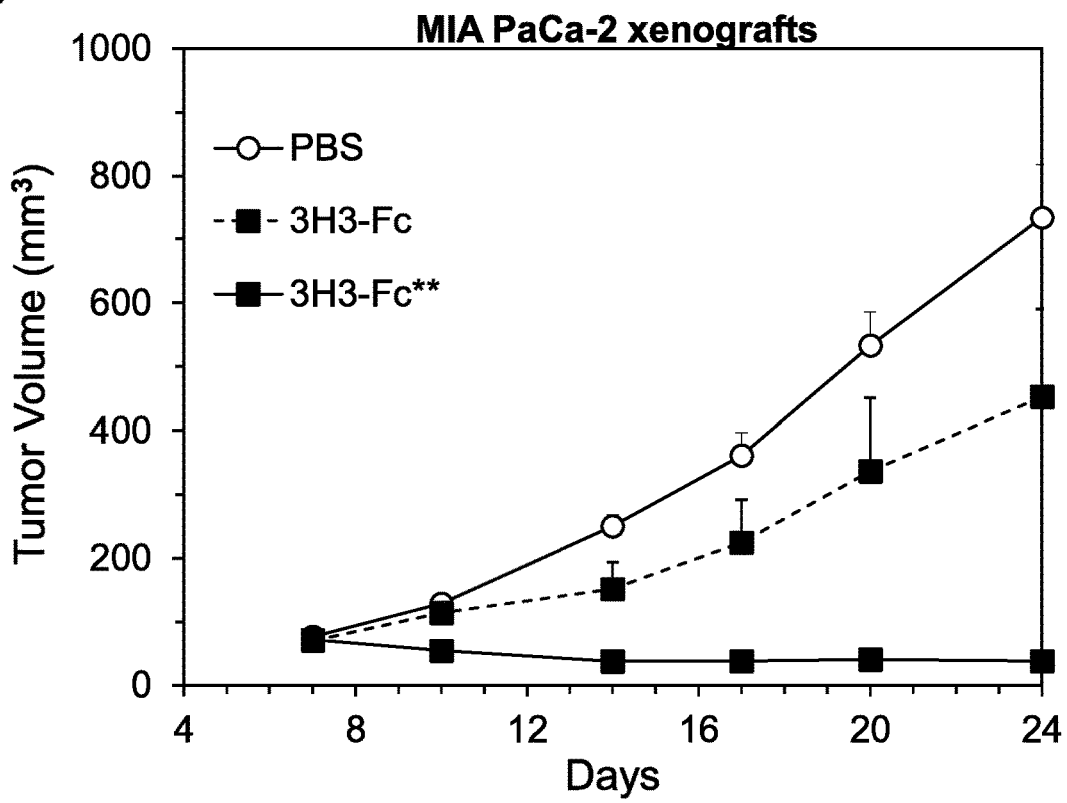
Figures 12A, B

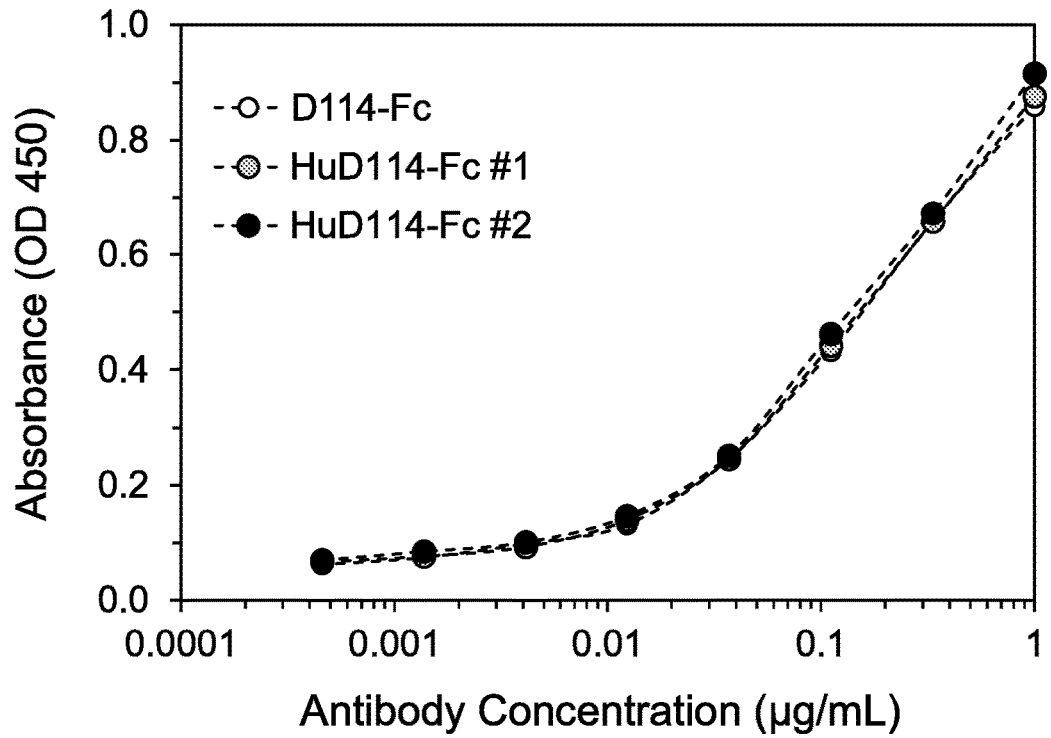
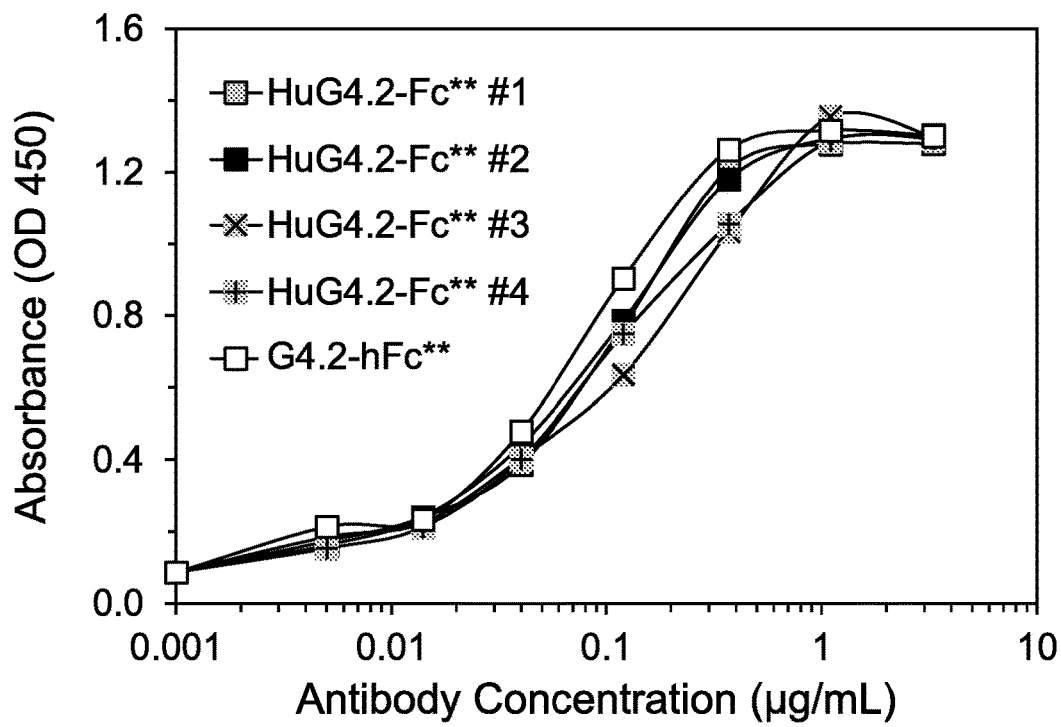
Figures 13A, B

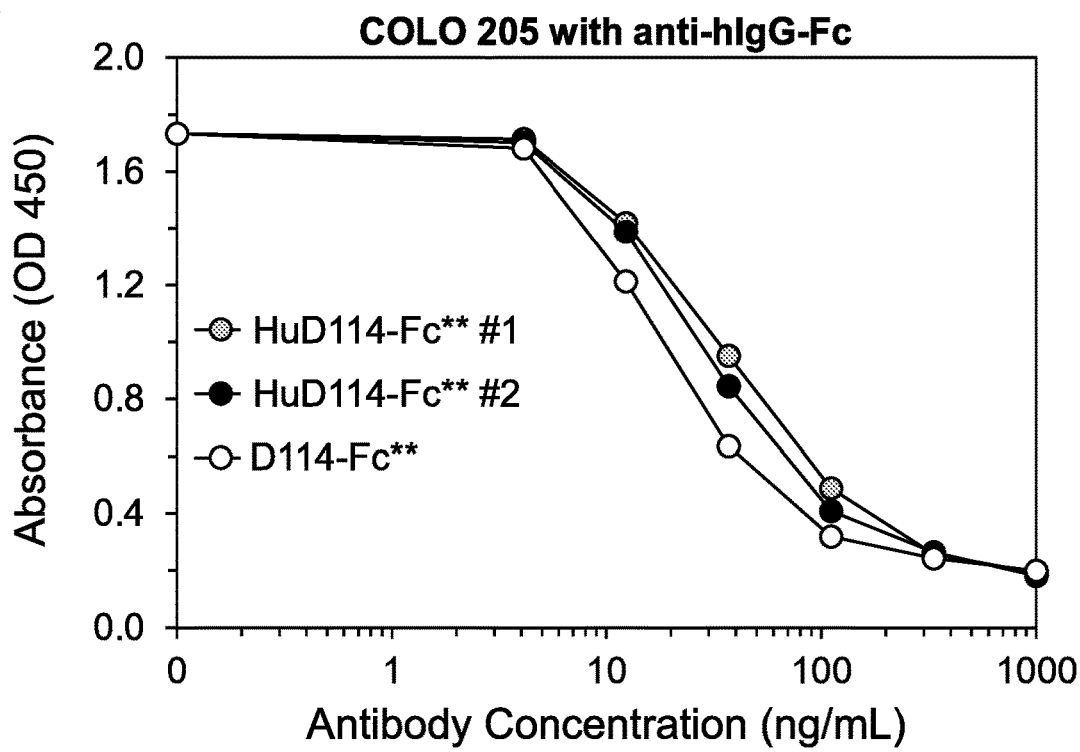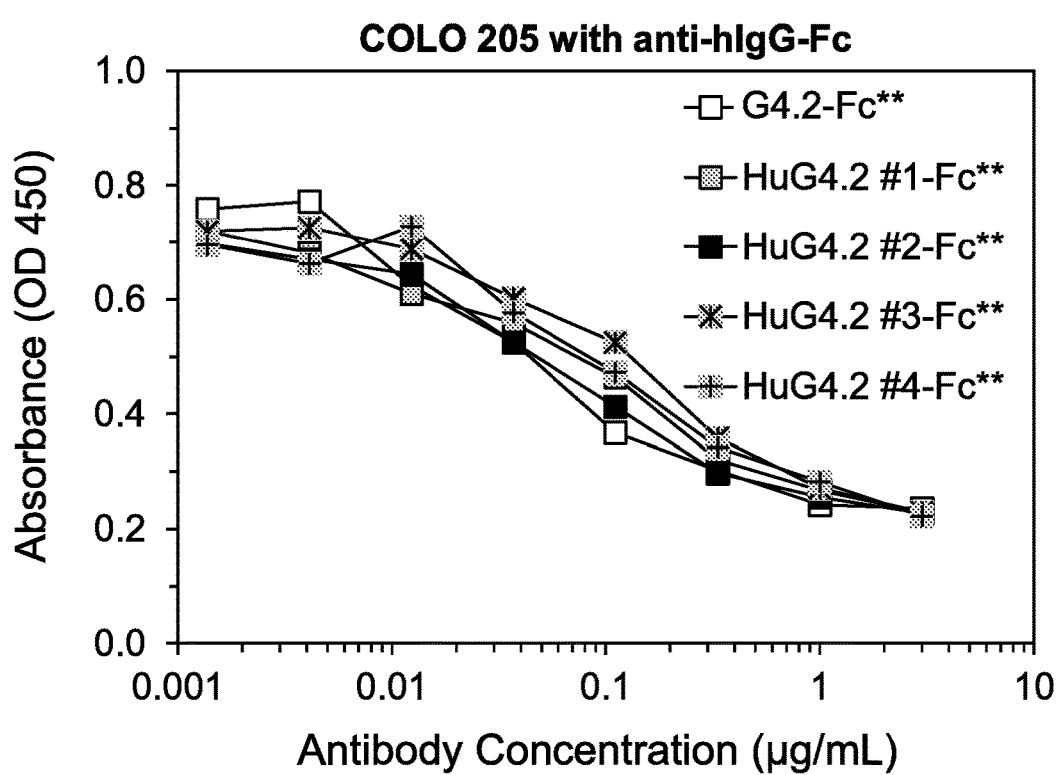
Figures 14A, B

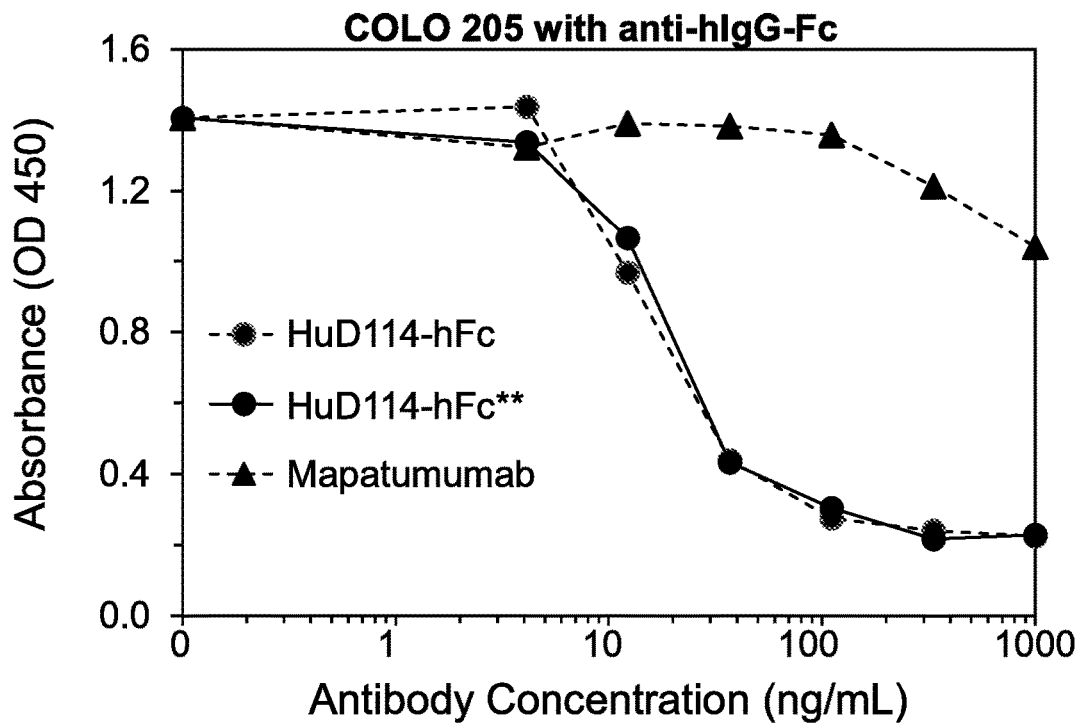
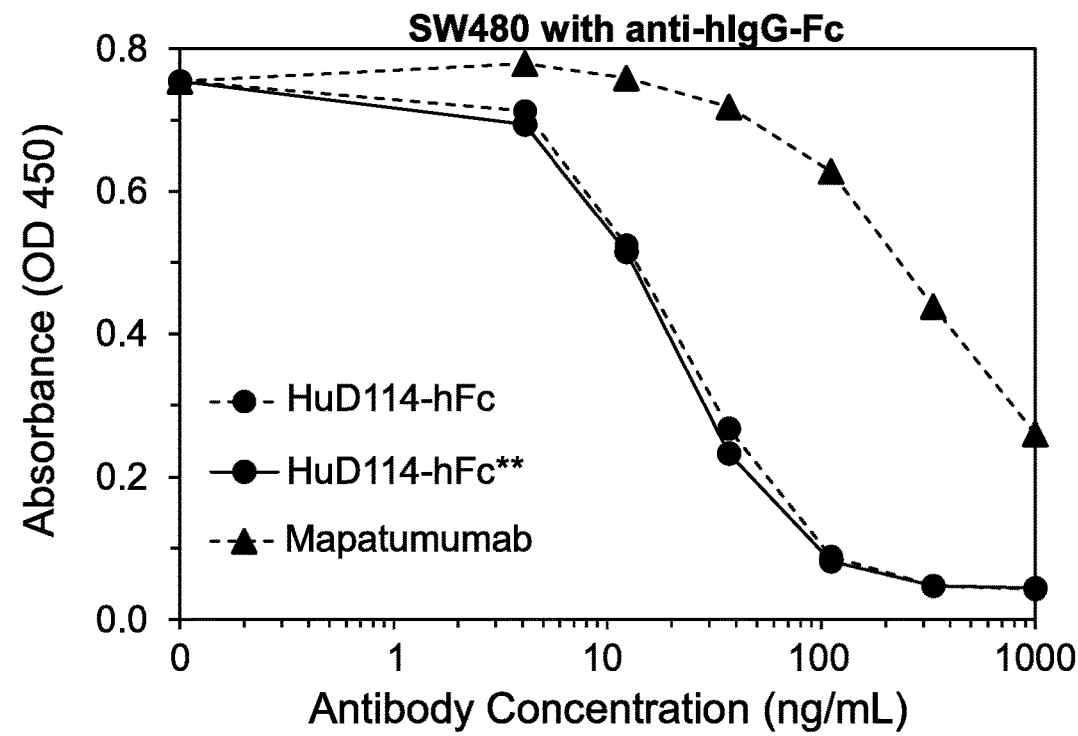
Figures 15A, B

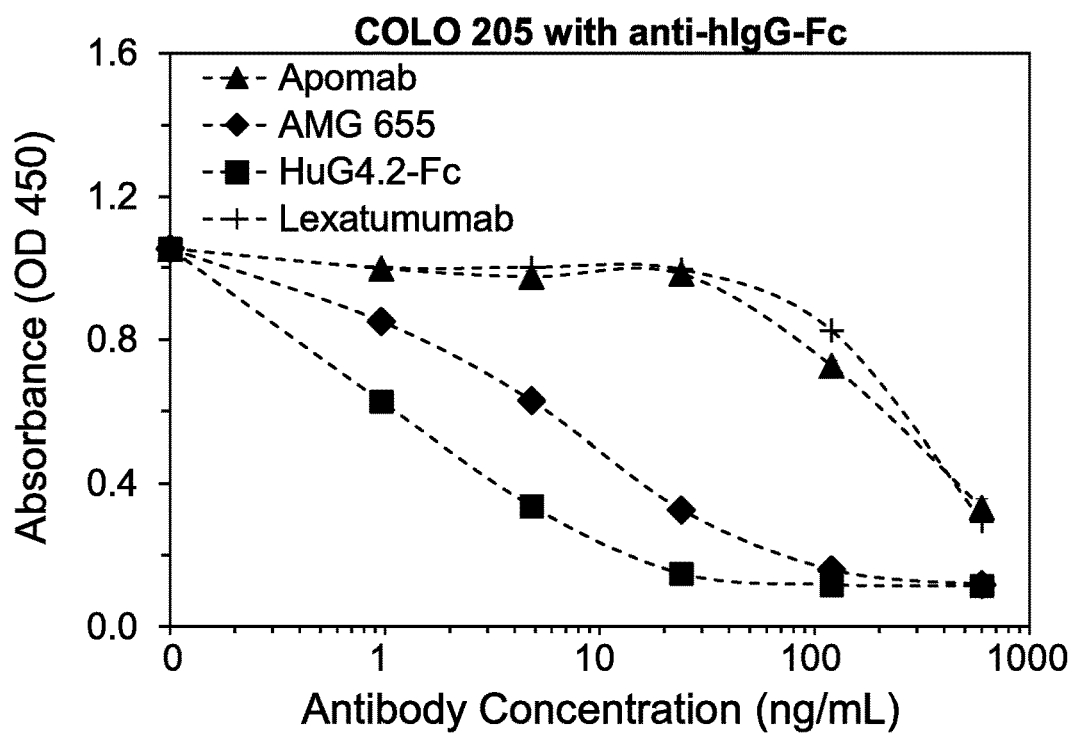
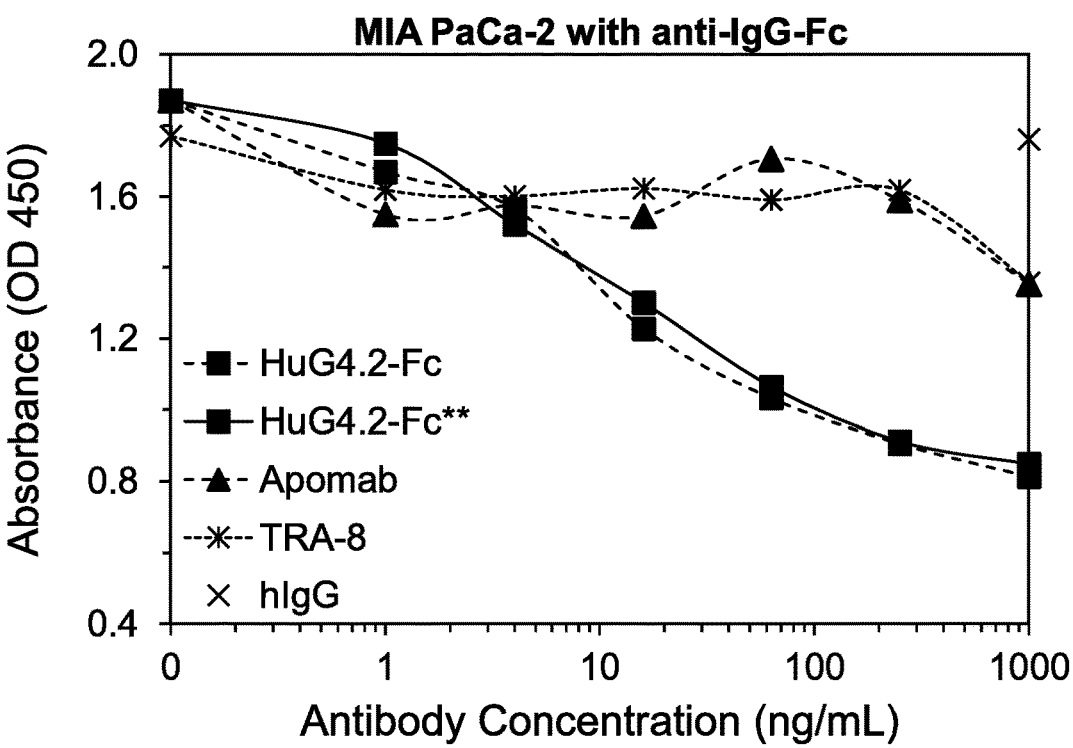
Figures 15C, D

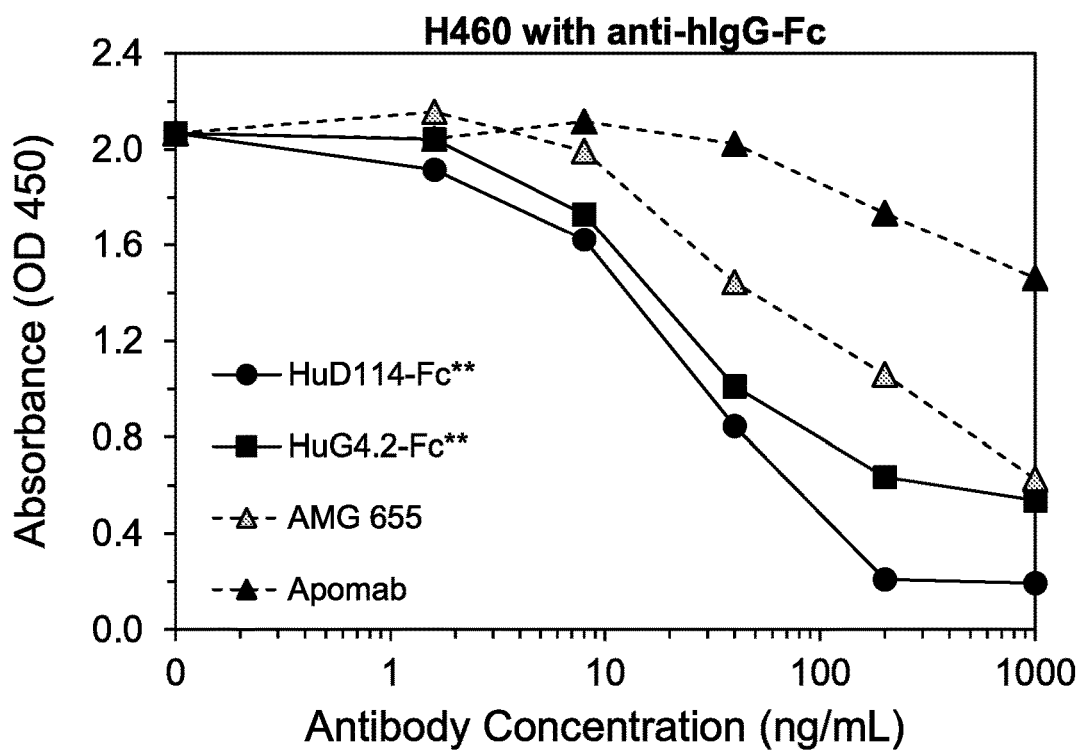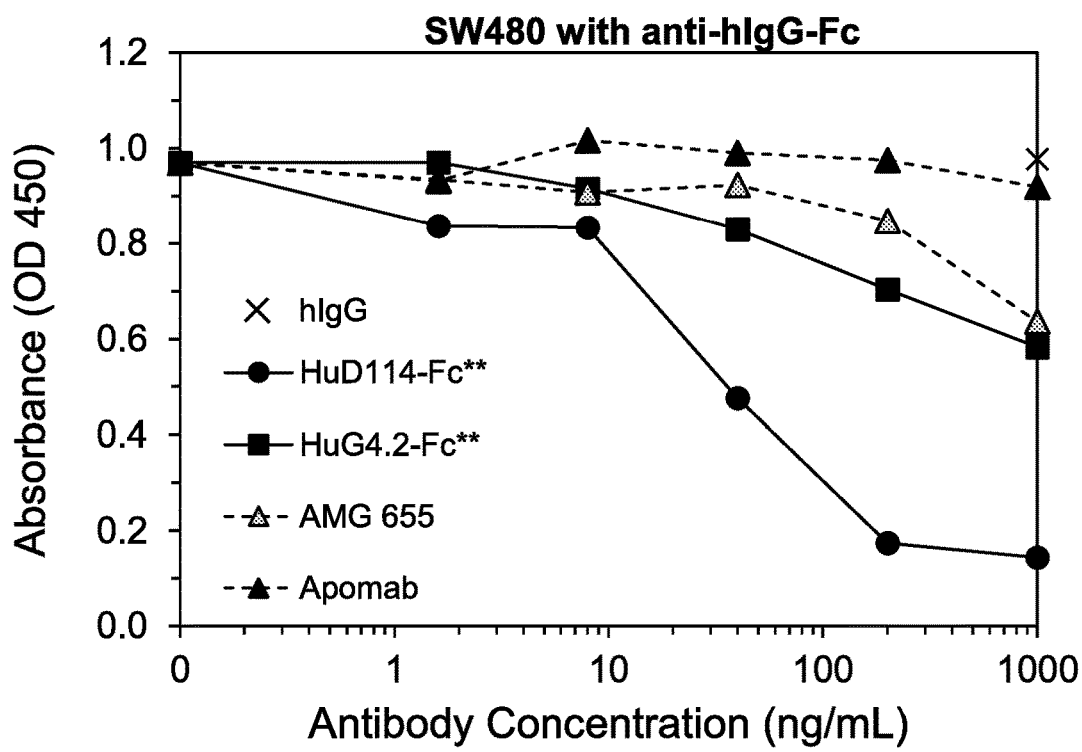
Figures 16A, B

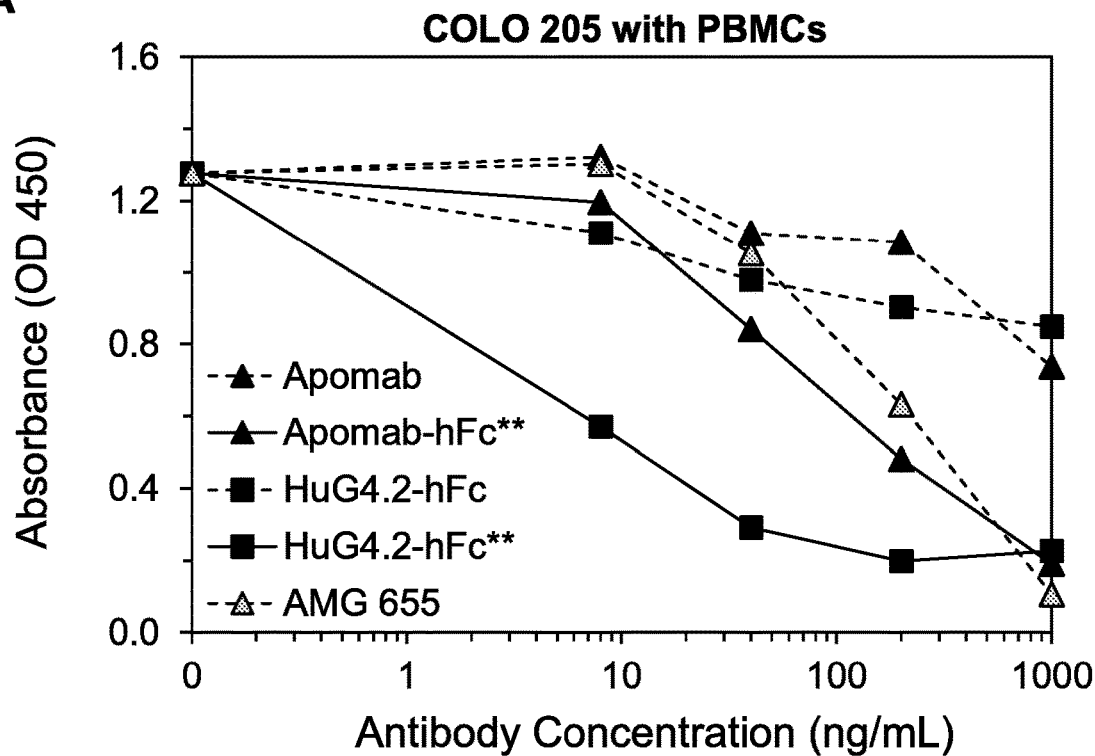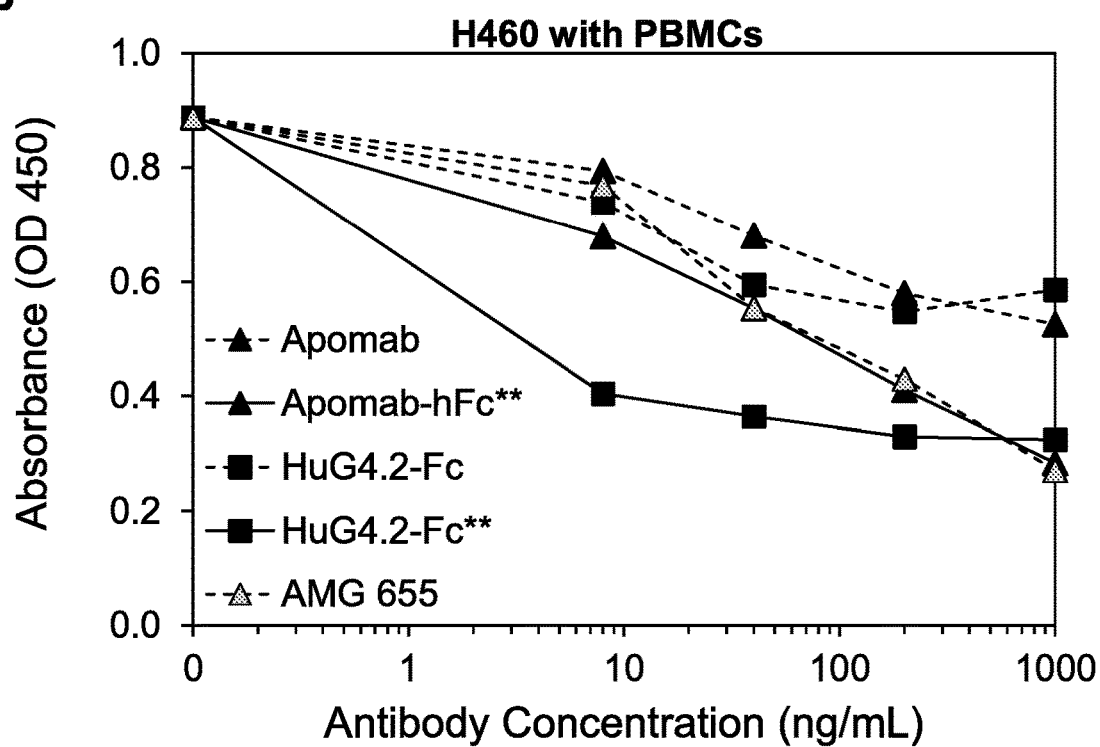
Figures 17A, B

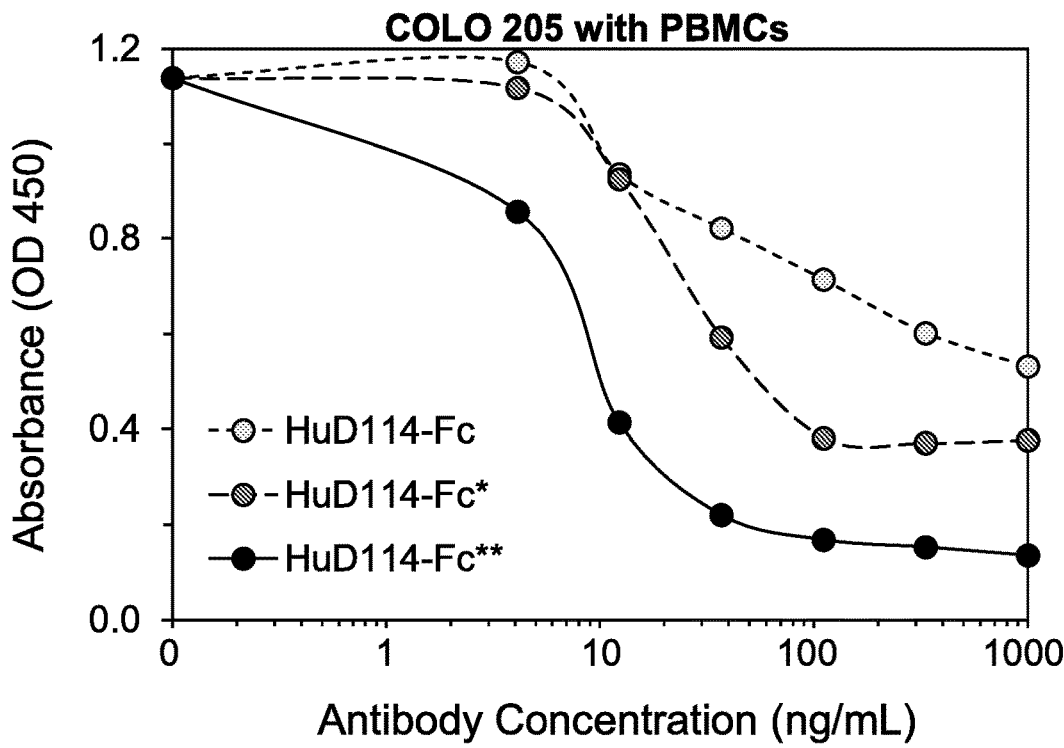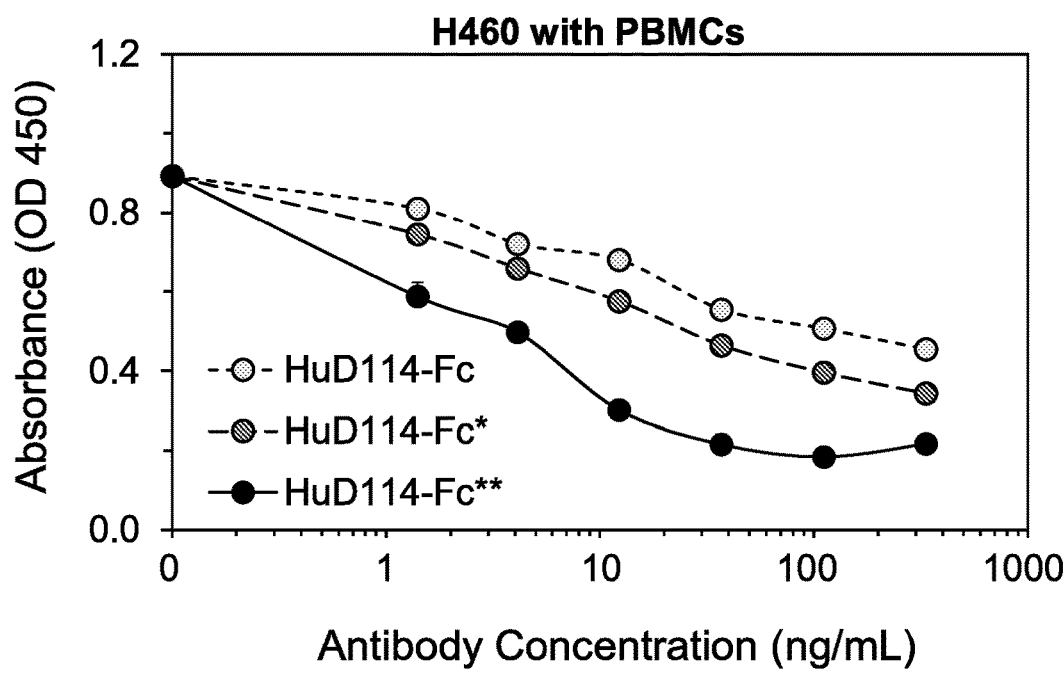
Figures 17C, D

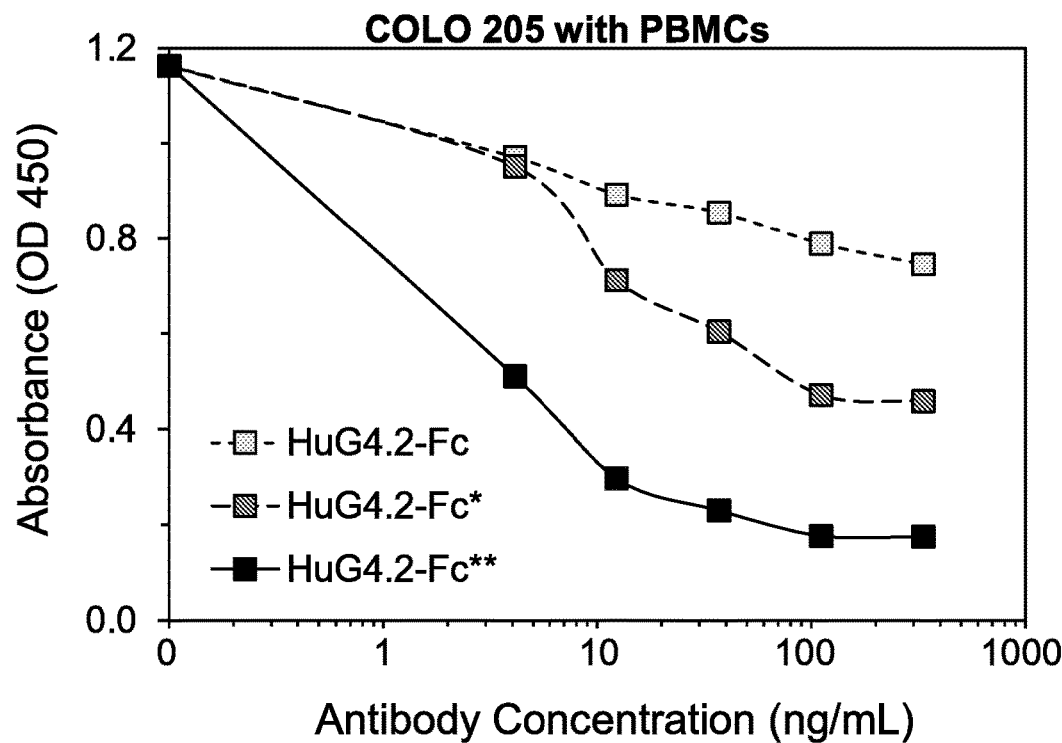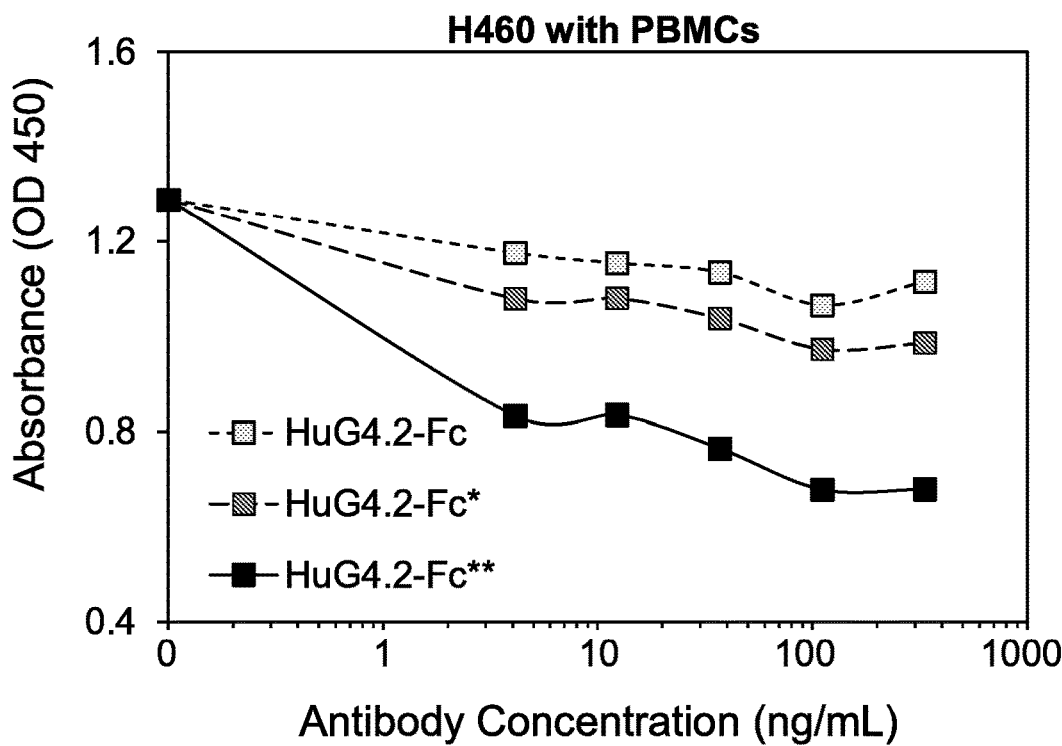
Figures 17E, F

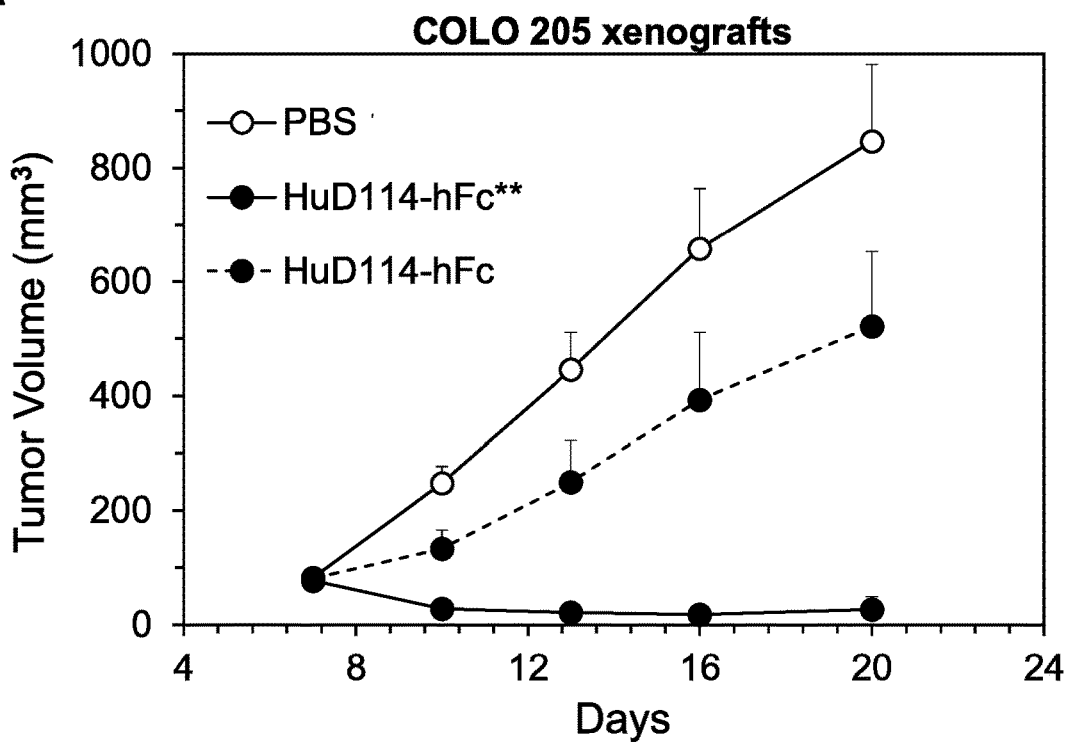
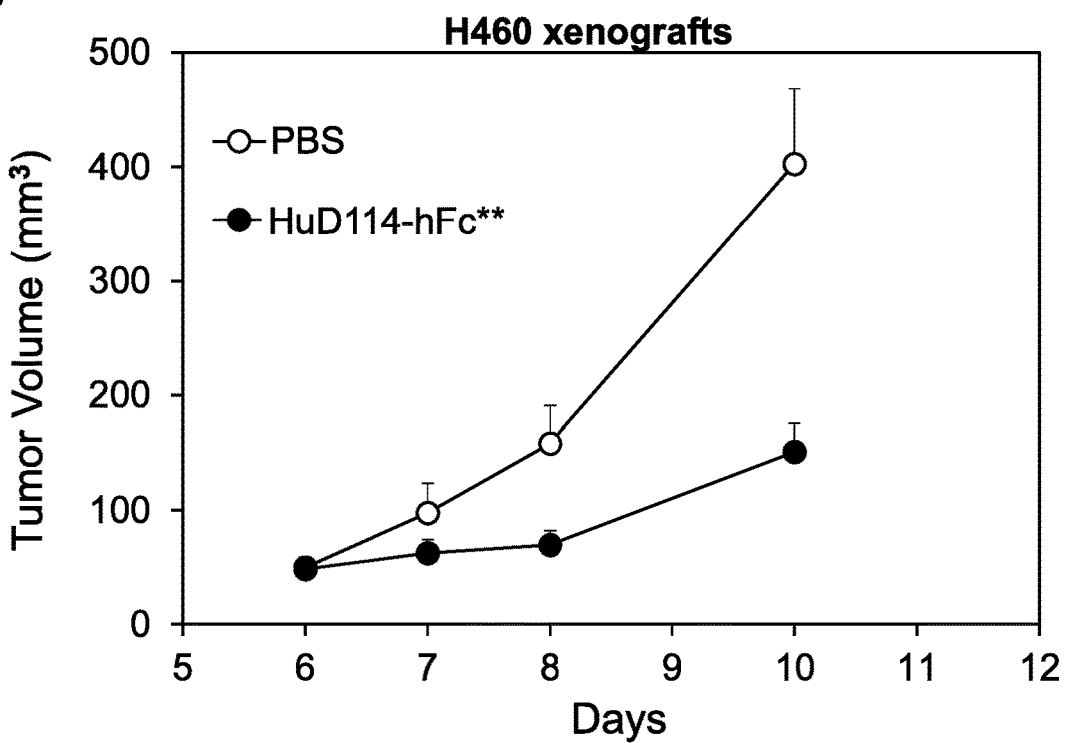
Figures 18A, B

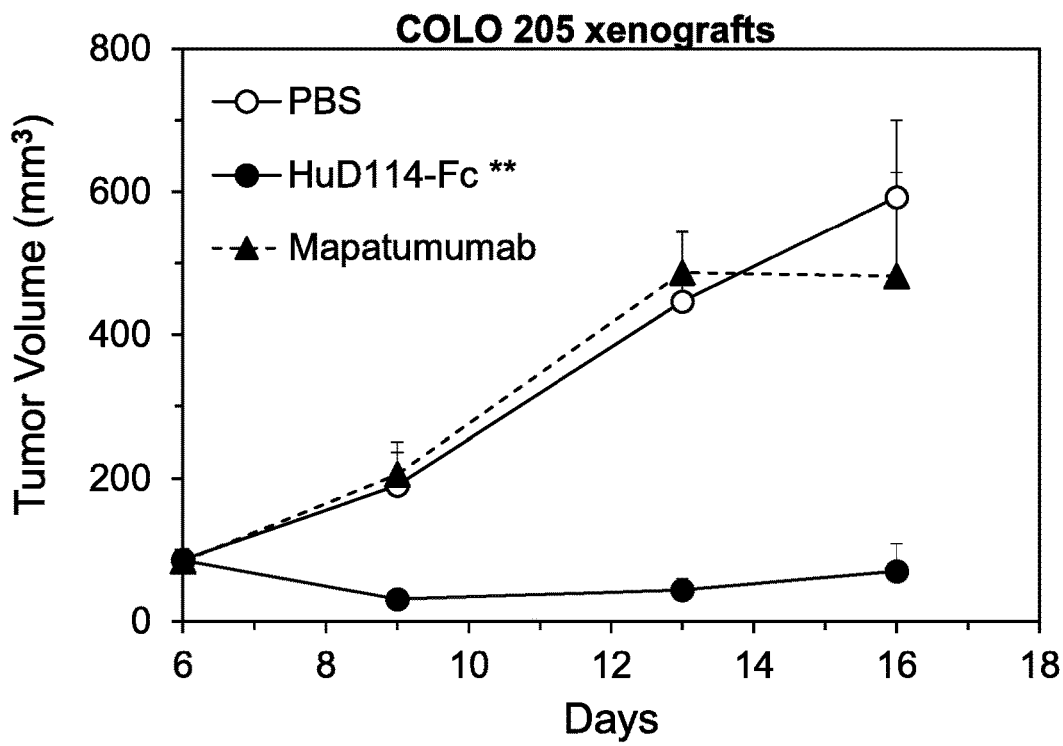
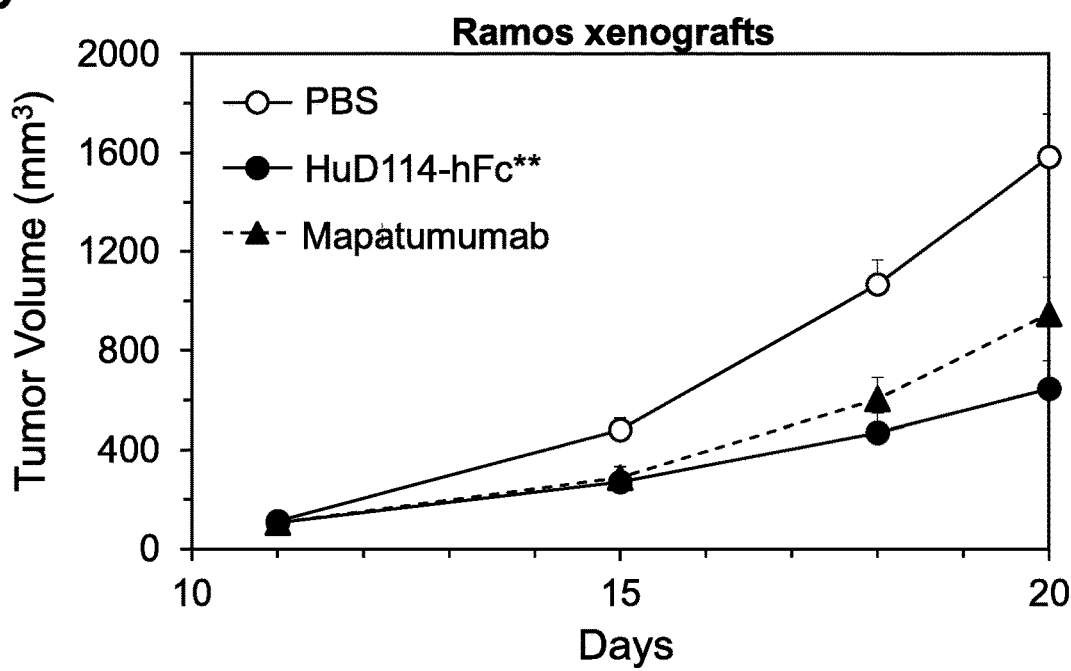
Figures 18C, D

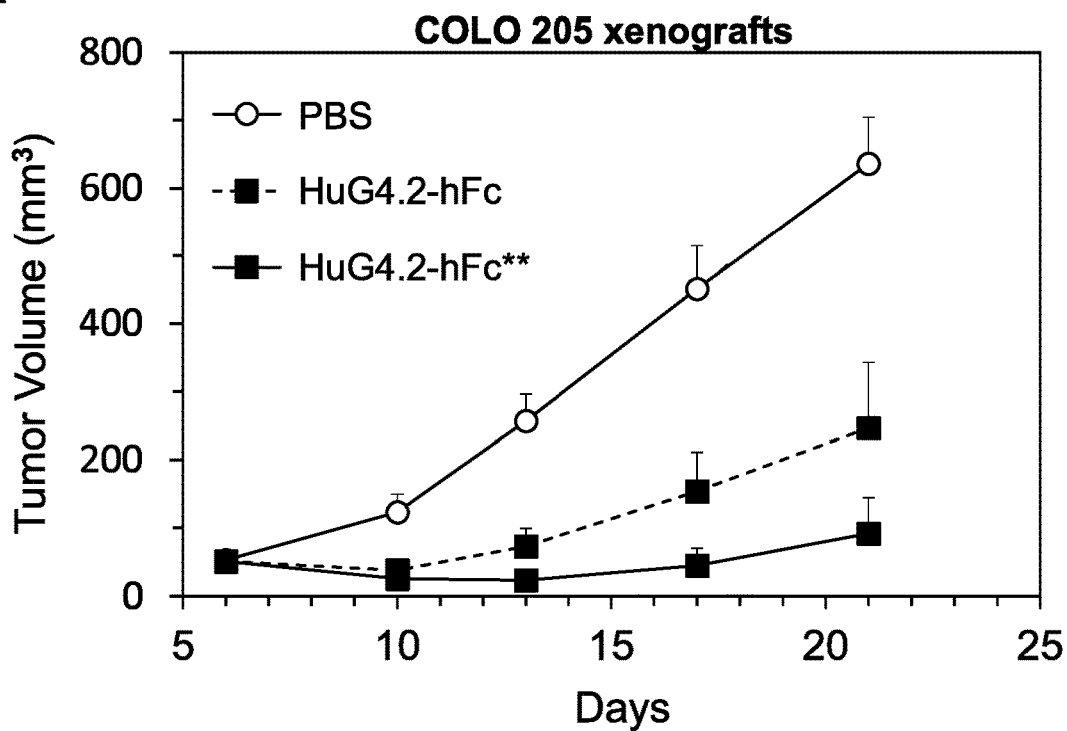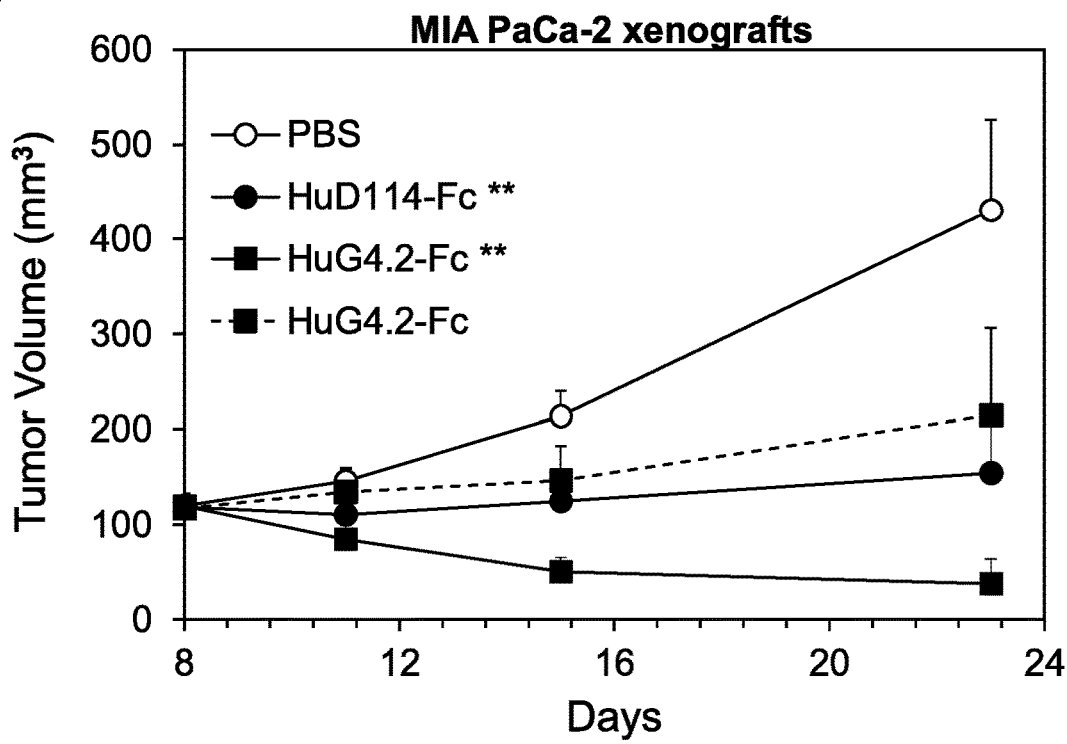
Figures 19A, B

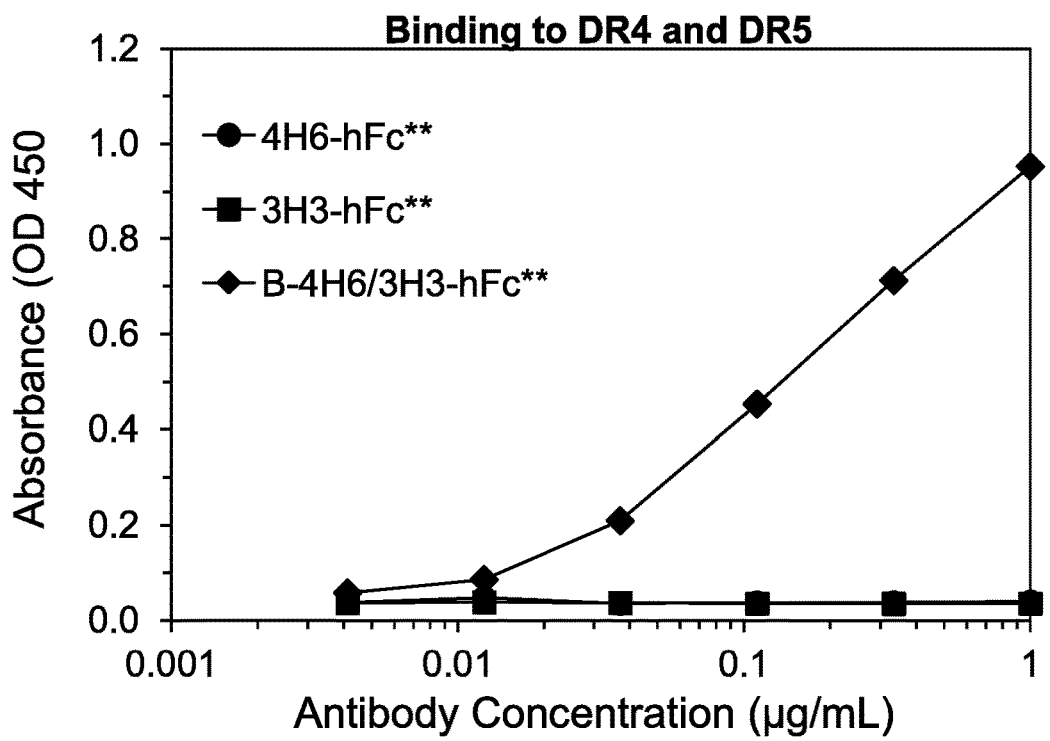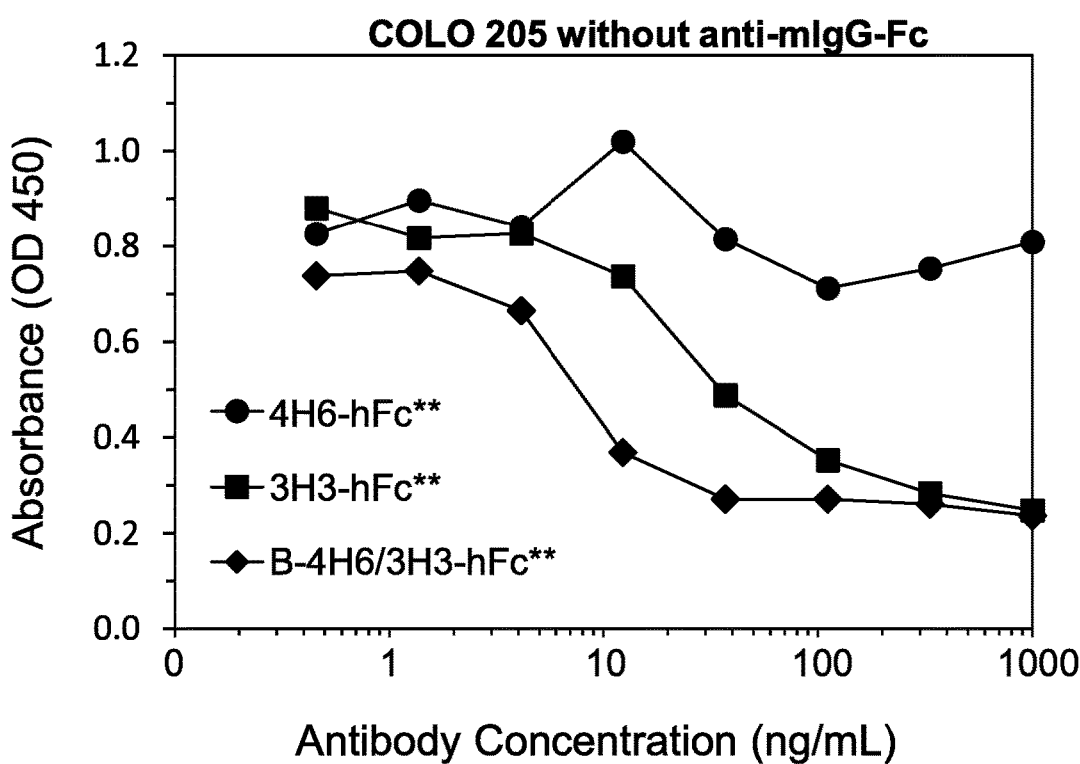
Figures 20A, B

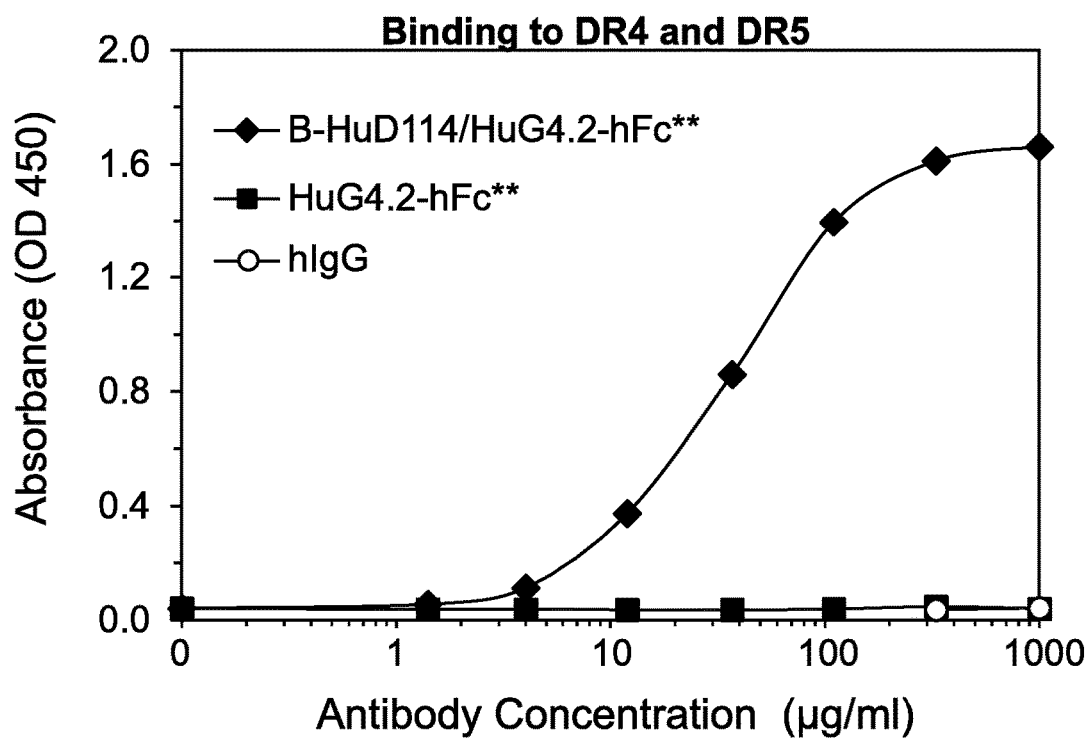
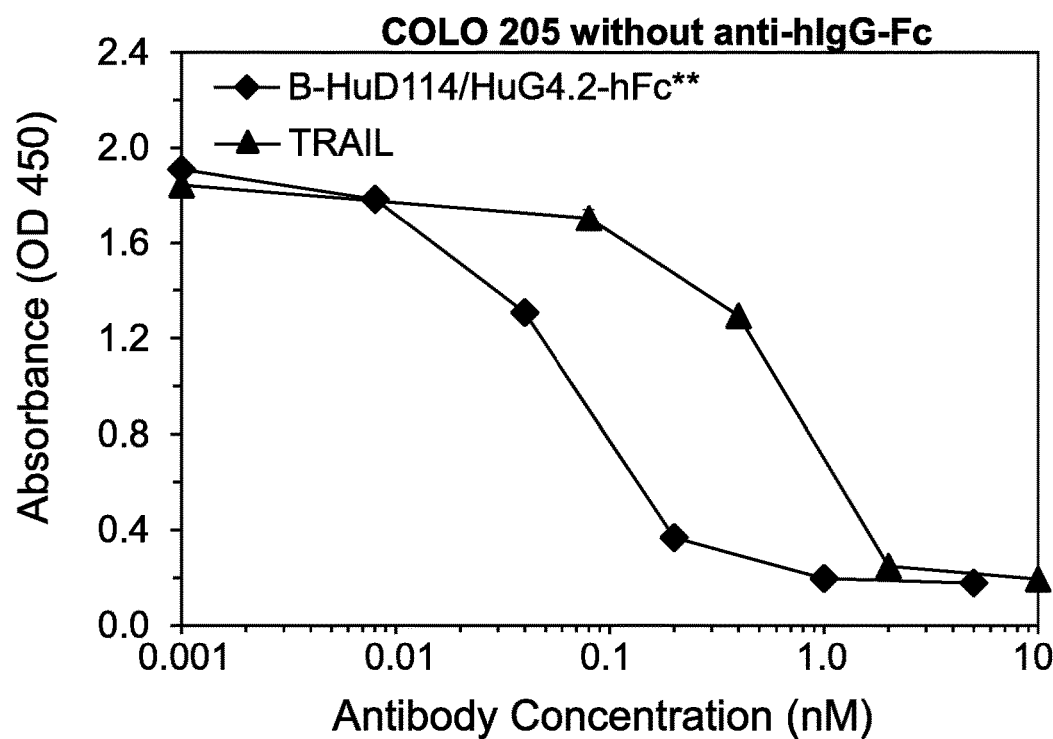
Figures 20C, D

SEQUENCE LISTING

```
<160> NUMBER OF SEQ ID NOS: 41

<210> SEQ ID NO 1
<211> LENGTH: 127
<212> TYPE: PRT
<213> ORGANISM: Mus musculus
<220> FEATURE:
<221> NAME/KEY: MISC_FEATURE
<223> OTHER INFORMATION: Mature heavy chain variable region of 4H6 mAb

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Val Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
            85                  90                  95

Arg Glu Gly Glu Phe Asp Tyr Tyr Gly Ser Ser Leu Leu Ser Tyr His
            100                 105                 110

Ser Met Asn Phe Trp Gly Gln Gly Thr Ser Val Thr Val Ser Ser
            115                 120                 125

<210> SEQ ID NO 2
<211> LENGTH: 107
<212> TYPE: PRT
<213> ORGANISM: Mus musculus
<220> FEATURE:
<221> NAME/KEY: MISC_FEATURE
<223> OTHER INFORMATION: Mature light chain variable region of 4H6 mAb

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80
```

```
Glu Asp Ile Ala Thr Tyr Phe Cys Gln Gln Gly Asn Thr Leu Pro Phe
                85                  90                  95

Thr Phe Gly Ser Gly Thr Lys Leu Glu Ile Lys
            100                 105

<210> SEQ ID NO 3
<211> LENGTH: 122
<212> TYPE: PRT
<213> ORGANISM: Mus musculus
<220> FEATURE:
<221> NAME/KEY: MISC_FEATURE
<223> OTHER INFORMATION: Mature heavy chain variable region of 3H3 mAb

<400> SEQUENCE: 3

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Arg Leu Thr Ser Glu Asp Ser Ala Val Tyr Tyr Cys
                85                  90                  95

Ala Arg Gly Gly Ile Asn Tyr Asp Tyr Leu Tyr Tyr Phe Asp Tyr Trp
            100                 105                 110

Gly Gln Gly Thr Thr Leu Thr Val Ser Ser
        115                 120

<210> SEQ ID NO 4
<211> LENGTH: 112
<212> TYPE: PRT
<213> ORGANISM: Mus musculus
<220> FEATURE:
<221> NAME/KEY: MISC_FEATURE
<223> OTHER INFORMATION: Mature light chain variable region of 3H3 mAb

<400> SEQUENCE: 4

Asp Val Val Met Thr Gln Ile Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro His Thr Phe Gly Gly Gly Thr Lys Leu Glu Ile Lys
            100                 105                 110

<210> SEQ ID NO 5
<211> LENGTH: 107
<212> TYPE: PRT
<213> ORGANISM: Mus musculus
```

<220> FEATURE:
<221> NAME/KEY: MISC_FEATURE
<223> OTHER INFORMATION: mature light chain variable region mouse D114

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Thr Asn Tyr
            20                  25                  30

Leu Asn Trp Tyr Gln Gln Lys Pro Asp Gly Thr Ile Lys Leu Leu Val
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys His Gln Tyr Ser Lys Leu Pro Trp
                85                  90                  95

Thr Phe Gly Gly Gly Thr Ser Leu Glu Ile Lys
            100                 105

<210> SEQ ID NO 6
<211> LENGTH: 107
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: Mature variable region of HuD114-L1 light chain

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Thr Asn Tyr
            20                  25                  30

Leu Asn Trp Tyr Gln Gln Lys Pro Gly Lys Ala Pro Lys Leu Leu Val
        35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys His Gln Tyr Ser Lys Leu Pro Trp
                85                  90                  95

Thr Phe Gly Gln Gly Thr Lys Val Glu Ile Lys
            100                 105

<210> SEQ ID NO 7
<211> LENGTH: 107
<212> TYPE: PRT
<213> ORGANISM: Homo sapiens
<220> FEATURE:
<221> NAME/KEY: MISC_FEATURE
<223> OTHER INFORMATION: human acceptor AIT38746  VK sequence

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile

```
                    35                  40                  45
Tyr Asp Ala Ser Asn Leu Glu Thr Gly Val Pro Ser Arg Phe Ser Gly
         50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Thr Trp
                 85                  90                  95
Thr Phe Gly Gln Gly Thr Lys Val Glu Ile Lys
            100                 105

<210> SEQ ID NO 8
<211> LENGTH: 117
<212> TYPE: PRT
<213> ORGANISM: Mus musculus
<220> FEATURE:
<221> NAME/KEY: MISC_FEATURE
<223> OTHER INFORMATION: mature heavy chain variable region mouse D114

<400> SEQUENCE: 8

Gln Ile Gln Leu Gln Gln Ser Gly Pro Glu Leu Met Lys Pro Gly Ser
1               5                   10                  15
Ser Val Lys Ile Ser Cys Lys Ala Ser Gly Tyr Thr Phe Thr Asn Tyr
            20                  25                  30
Tyr Ile Asn Trp Val Lys Gln Arg Pro Gly Gln Gly Leu Glu Trp Leu
        35                  40                  45
Gly Trp Ile Tyr Pro Gly Ile Gly Asp Ile Lys Tyr Asn Glu Lys Phe
    50                  55                  60
Lys Gly Arg Ala Thr Leu Thr Ala Asp Thr Ser Ser Asn Thr Ala Tyr
65                  70                  75                  80
Met Gln Leu Asn Arg Leu Thr Ser Asp Asp Thr Gly Val Tyr Phe Cys
                85                  90                  95
Ala Arg Ser Gly Trp Ala Trp Phe Val Asp Trp Gly Gln Gly Thr Leu
            100                 105                 110
Val Ser Val Ser Ser
        115

<210> SEQ ID NO 9
<211> LENGTH: 117
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: Mature variable region of HuD114-H1 heavy chain

<400> SEQUENCE: 9

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Tyr Ile Asn Trp Val Arg Gln Ala Pro Gly Gln Gly Leu Glu Trp Leu
        35                  40                  45
Gly Trp Ile Tyr Pro Gly Ile Gly Asp Ile Lys Tyr Asn Glu Lys Phe
    50                  55                  60
Lys Gly Arg Val Thr Met Thr Ala Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
```

Ala Arg Ser Gly Trp Ala Trp Phe Val Asp Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: Mature variable region of HuD114-H2 heavy chain

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Asn Trp Val Arg Gln Ala Pro Gly Gln Gly Leu Glu Trp Leu
        35                  40                  45

Gly Trp Ile Tyr Pro Gly Ile Gly Asp Ile Lys Tyr Asn Glu Lys Phe
    50                  55                  60

Lys Gly Arg Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Trp Ala Trp Phe Val Asp Trp Gly Gln Gly Thr Leu
            100                 105                 110

Val Thr Val Ser Ser
        115

<210> SEQ ID NO 11
<211> LENGTH: 118
<212> TYPE: PRT
<213> ORGANISM: Homo sapiens
<220> FEATURE:
<221> NAME/KEY: MISC_FEATURE
<223> OTHER INFORMATION: human acceptor AAC18293 VH sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Ala Gly Ala Ala Tyr Phe Asp Tyr Trp Gly Gln Gly Thr
            100                 105                 110

Leu Val Thr Val Ser Ser
        115

<210> SEQ ID NO 12
<211> LENGTH: 111
<212> TYPE: PRT
<213> ORGANISM: Mus musculus
<220> FEATURE:
<221> NAME/KEY: MISC_FEATURE
<223> OTHER INFORMATION: mature light chain variable region mouse G4.2

<400> SEQUENCE: 12

```
Asn Ile Val Leu Thr Gln Ser Pro Ala Ser Leu Ala Val Ser Leu Gly
1               5                   10                  15

Gln Arg Ala Thr Met Ser Cys Arg Ala Ser Glu Ser Val Asp Ile Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ser Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Ser Tyr
                85                  90                  95

Glu Asp Pro Leu Thr Phe Gly Ala Gly Thr Lys Leu Asp Leu Lys
            100                 105                 110
```

<210> SEQ ID NO 13
<211> LENGTH: 111
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: mature variable region of HuG4.2-L1 light chain

<400> SEQUENCE: 13

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Ile Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ser Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Tyr
                85                  90                  95

Glu Asp Pro Leu Thr Phe Gly Gly Gly Thr Lys Val Glu Ile Lys
            100                 105                 110
```

<210> SEQ ID NO 14
<211> LENGTH: 111
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: mature variable region of HuG4.2-L2 light chain

<400> SEQUENCE: 14

-continued

Asn Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Ile Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ser Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Tyr
                85                  90                  95

Glu Asp Pro Leu Thr Phe Gly Gly Gly Thr Lys Val Glu Ile Lys
            100                 105                 110

<210> SEQ ID NO 15
<211> LENGTH: 113
<212> TYPE: PRT
<213> ORGANISM: Homo sapiens
<220> FEATURE:
<221> NAME/KEY: MISC_FEATURE
<223> OTHER INFORMATION: human acceptor AAQ02698 VK sequence

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 16
<211> LENGTH: 121
<212> TYPE: PRT
<213> ORGANISM: Mus musculus
<220> FEATURE:
<221> NAME/KEY: MISC_FEATURE
<223> OTHER INFORMATION: mature heavy chain variable region mouse G4.2

<400> SEQUENCE: 16

Asp Val Lys Leu Val Glu Ser Gly Gly Gly Leu Val Lys Leu Gly Gly
1               5                   10                  15

Ser Leu Lys Leu Ser Cys Ala Ala Ser Gly Leu Pro Phe Asn Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Arg Ile His Tyr Pro Asp Thr Val
    50                  55                  60

Lys Gly Arg Phe Thr Ile Ser Arg Asp Asn Ala Lys Asn Thr Leu Tyr

```
                65                  70                  75                  80
Leu Gln Met Ser Ser Leu Lys Ser Glu Asp Thr Ala Leu Tyr Tyr Cys
                        85                  90                  95

Thr Arg Leu Thr Tyr Tyr Gly Asn Pro Ala Trp Phe Ala Tyr Trp Gly
                    100                 105                 110

Gln Gly Thr Leu Val Thr Val Ser Ala
            115                 120

<210> SEQ ID NO 17
<211> LENGTH: 121
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: mature variable region of HuG4.2-H1 heavy chain

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Pro Phe Asn Ser Tyr
            20                  25                  30

Tyr Met Ser Trp Val Arg Gln Ala Pro Gly Lys Gly Leu Glu Trp Val
        35                  40                  45

Ala Ala Ile Asn Ser Asn Gly Gly Arg Ile His Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                        85                  90                  95

Thr Arg Leu Thr Tyr Tyr Gly Asn Pro Ala Trp Phe Ala Tyr Trp Gly
                    100                 105                 110

Gln Gly Thr Leu Val Thr Val Ser Ser
            115                 120

<210> SEQ ID NO 18
<211> LENGTH: 121
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: mature variable region of HuG4.2-H2 heavy chain

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Pro Phe Asn Ser Tyr
            20                  25                  30

Tyr Met Ser Trp Val Arg Gln Ala Pro Gly Lys Gly Leu Glu Leu Val
        35                  40                  45

Ala Ala Ile Asn Ser Asn Gly Gly Arg Ile His Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                        85                  90                  95
```

Thr Arg Leu Thr Tyr Tyr Gly Asn Pro Ala Trp Phe Ala Tyr Trp Gly
            100                 105                 110

Gln Gly Thr Leu Val Thr Val Ser Ser
        115                 120

<210> SEQ ID NO 19
<211> LENGTH: 116
<212> TYPE: PRT
<213> ORGANISM: Homo sapiens
<220> FEATURE:
<221> NAME/KEY: MISC_FEATURE
<223> OTHER INFORMATION: human acceptor AAC50998 VH sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ser Asp Met Asp Tyr Trp Gly Gln Gly Thr Leu Val
            100                 105                 110

Thr Val Ser Ser
        115

<210> SEQ ID NO 20
<211> LENGTH: 11
<212> TYPE: PRT
<213> ORGANISM: Mus musculus
<220> FEATURE:
<221> NAME/KEY: MISC_FEATURE
<223> OTHER INFORMATION: CDR-L1 of D114

<400> SEQUENCE: 20

Ser Ala Ser Gln Asp Ile Thr Asn Tyr Leu Asn
1               5                   10

<210> SEQ ID NO 21
<211> LENGTH: 7
<212> TYPE: PRT
<213> ORGANISM: Mus musculus
<220> FEATURE:
<221> NAME/KEY: MISC_FEATURE
<223> OTHER INFORMATION: CDR-L2 of D114

<400> SEQUENCE: 21

Tyr Thr Ser Ser Leu His Ser
1               5

<210> SEQ ID NO 22
<211> LENGTH: 9
<212> TYPE: PRT
<213> ORGANISM: Mus musculus
<220> FEATURE:
<221> NAME/KEY: MISC_FEATURE
<223> OTHER INFORMATION: CDR-L3 of D114

<400> SEQUENCE: 22

His Gln Tyr Ser Lys Leu Pro Trp Thr
1               5

<210> SEQ ID NO 23
<211> LENGTH: 5
<212> TYPE: PRT
<213> ORGANISM: Mus musculus
<220> FEATURE:
<221> NAME/KEY: MISC_FEATURE
<223> OTHER INFORMATION: CDR-H1 of D114

<400> SEQUENCE: 23

Asn Tyr Tyr Ile Asn
1               5

<210> SEQ ID NO 24
<211> LENGTH: 17
<212> TYPE: PRT
<213> ORGANISM: Mus musculus
<220> FEATURE:
<221> NAME/KEY: MISC_FEATURE
<223> OTHER INFORMATION: CDR-H2 of D114

<400> SEQUENCE: 24

Trp Ile Tyr Pro Gly Ile Gly Asp Ile Lys Tyr Asn Glu Lys Phe Lys
1               5                   10                  15

Gly

<210> SEQ ID NO 25
<211> LENGTH: 8
<212> TYPE: PRT
<213> ORGANISM: Mus musculus
<220> FEATURE:
<221> NAME/KEY: MISC_FEATURE
<223> OTHER INFORMATION: CDR-H3 of D114

<400> SEQUENCE: 25

Ser Gly Trp Ala Trp Phe Val Asp
1               5

<210> SEQ ID NO 26
<211> LENGTH: 15
<212> TYPE: PRT
<213> ORGANISM: Mus musculus
<220> FEATURE:
<221> NAME/KEY: MISC_FEATURE
<223> OTHER INFORMATION: CDR-L1 of G4.2

<400> SEQUENCE: 26

Arg Ala Ser Glu Ser Val Asp Ile Tyr Gly Asn Ser Phe Met His
1               5                   10                  15

<210> SEQ ID NO 27
<211> LENGTH: 7
<212> TYPE: PRT
<213> ORGANISM: Mus musculus
<220> FEATURE:
<221> NAME/KEY: MISC_FEATURE
<223> OTHER INFORMATION: CDR-L2 of G4.2

<400> SEQUENCE: 27

Leu Ser Ser Asn Leu Glu Ser
1               5

<210> SEQ ID NO 28
<211> LENGTH: 9

```
<212> TYPE: PRT
<213> ORGANISM: Mus musculus
<220> FEATURE:
<221> NAME/KEY: MISC_FEATURE
<223> OTHER INFORMATION: CDR-L3 of G4.2

<400> SEQUENCE: 28

Gln Gln Ser Tyr Glu Asp Pro Leu Thr
1               5

<210> SEQ ID NO 29
<211> LENGTH: 5
<212> TYPE: PRT
<213> ORGANISM: Mus musculus
<220> FEATURE:
<221> NAME/KEY: MISC_FEATURE
<223> OTHER INFORMATION: CDR-H1 of G4.2

<400> SEQUENCE: 29

Ser Tyr Tyr Met Ser
1               5

<210> SEQ ID NO 30
<211> LENGTH: 17
<212> TYPE: PRT
<213> ORGANISM: Mus musculus
<220> FEATURE:
<221> NAME/KEY: MISC_FEATURE
<223> OTHER INFORMATION: CDR-H2 of G4.2

<400> SEQUENCE: 30

Ala Ile Asn Ser Asn Gly Gly Arg Ile His Tyr Pro Asp Thr Val Lys
1               5                   10                  15

Gly

<210> SEQ ID NO 31
<211> LENGTH: 12
<212> TYPE: PRT
<213> ORGANISM: Mus musculus
<220> FEATURE:
<221> NAME/KEY: MISC_FEATURE
<223> OTHER INFORMATION: CDR-H3 of G4.2

<400> SEQUENCE: 31

Leu Thr Tyr Tyr Gly Asn Pro Ala Trp Phe Ala Tyr
1               5                   10

<210> SEQ ID NO 32
<211> LENGTH: 604
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: complete heavy chain of B-4H6/3H3-hFc**
      bispecific antibody including signal peptide

<400> SEQUENCE: 32

Met Glu Phe Gly Leu Ser Trp Val Phe Leu Val Ala Leu Leu Arg Gly
1               5                   10                  15

Val Gln Cys Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Pro Pro Gly Lys Gly Leu
```

-continued

```
                 50                  55                  60
Glu Trp Leu Gly Val Ile Trp Ala Val Gly Ser Thr Asn Tyr Asn Ser
 65                  70                  75                  80

Ala Leu Met Ser Arg Leu Ser Ile Ser Lys Asp Asn Ser Lys Ser Gln
                 85                  90                  95

Val Phe Leu Lys Met Asn Ser Leu Gln Thr Asp Asp Thr Ala Met Tyr
                100                 105                 110

Tyr Cys Ala Arg Glu Gly Glu Phe Asp Tyr Tyr Gly Ser Ser Leu Leu
                115                 120                 125

Ser Tyr His Ser Met Asn Phe Trp Gly Gln Gly Thr Ser Val Thr Val
                130                 135                 140

Ser Ser Ala Ser Gly Ser Gly Gly Gly Ser Gly Gly Gly Gly Gly Ser
145                 150                 155                 160

Gly Gly Gly Gly Ser Asp Ile Gln Met Thr Gln Thr Ser Ser Ser Leu
                165                 170                 175

Ser Ala Ser Leu Gly Asp Arg Val Thr Ile Ser Cys Arg Ala Ser Gln
                180                 185                 190

Asp Ile Ser Asn Tyr Leu Asn Trp Tyr Gln Arg Lys Pro Asp Gly Thr
                195                 200                 205

Val Lys Leu Leu Ile Tyr Tyr Thr Ser Arg Leu His Ser Gly Val Pro
                210                 215                 220

Ser Arg Phe Ser Gly Ser Gly Ser Gly Thr Asp Tyr Ser Leu Thr Ile
225                 230                 235                 240

Ser Asn Leu Glu Gln Glu Asp Ile Ala Thr Tyr Phe Cys Gln Gln Gly
                245                 250                 255

Asn Thr Leu Pro Phe Thr Phe Gly Ser Gly Thr Lys Leu Glu Ile Lys
                260                 265                 270

Ser Ser Ala Ser Thr Lys Gly Pro Ser Val Phe Pro Leu Ala Pro Ser
                275                 280                 285

Ser Lys Ser Thr Ser Gly Gly Thr Ala Ala Leu Gly Cys Leu Val Lys
                290                 295                 300

Asp Tyr Phe Pro Glu Pro Val Thr Val Ser Trp Asn Ser Gly Ala Leu
305                 310                 315                 320

Thr Ser Gly Val His Thr Phe Pro Ala Val Leu Gln Ser Ser Gly Leu
                325                 330                 335

Tyr Ser Leu Ser Ser Val Val Thr Val Pro Ser Ser Ser Leu Gly Thr
                340                 345                 350

Gln Thr Tyr Ile Cys Asn Val Asn His Lys Pro Ser Asn Thr Lys Val
                355                 360                 365

Asp Lys Arg Val Glu Pro Lys Ser Cys Asp Lys Thr His Thr Cys Pro
370                 375                 380

Pro Cys Pro Ala Pro Glu Leu Leu Gly Gly Pro Ser Val Phe Leu Phe
385                 390                 395                 400

Pro Pro Lys Pro Lys Asp Thr Leu Met Ile Ser Arg Thr Pro Glu Val
                405                 410                 415

Thr Cys Val Val Val Asp Val Glu His Glu Asp Pro Glu Val Lys Phe
                420                 425                 430

Asn Trp Tyr Val Asp Gly Val Glu Val His Asn Ala Lys Thr Lys Pro
                435                 440                 445

Arg Glu Glu Gln Tyr Asn Ser Thr Tyr Arg Val Val Ser Val Leu Thr
                450                 455                 460

Val Leu His Gln Asp Trp Leu Asn Gly Lys Glu Tyr Lys Cys Lys Val
465                 470                 475                 480
```

Ser Asn Lys Ala Phe Pro Ala Pro Ile Glu Lys Thr Ile Ser Lys Ala
            485                 490                 495

Lys Gly Gln Pro Arg Glu Pro Gln Val Tyr Thr Leu Pro Pro Ser Arg
        500                 505                 510

Glu Glu Met Thr Lys Asn Gln Val Ser Leu Thr Cys Leu Val Lys Gly
            515                 520                 525

Phe Tyr Pro Ser Asp Ile Ala Val Glu Trp Glu Ser Asn Gly Gln Pro
        530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
            580                 585                 590

Tyr Thr Gln Lys Ser Leu Ser Leu Ser Pro Gly Lys
        595                 600

<210> SEQ ID NO 33
<211> LENGTH: 379
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: complete light chain of B-4H6/3H3-hFc**
      bispecific antibody including signal peptide

<400> SEQUENCE: 33

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Ile Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Arg Leu Thr Ser Glu Asp Ser Ala Val
            100                 105                 110

Tyr Tyr Cys Ala Arg Gly Gly Ile Asn Tyr Asp Tyr Leu Tyr Tyr Phe
        115                 120                 125

Asp Tyr Trp Gly Gln Gly Thr Thr Leu Thr Val Ser Ser Ala Ser Gly
    130                 135                 140

Ser Gly Gly Gly Ser Gly Gly Gly Ser Gly Gly Gly Ser
145                 150                 155                 160

Asp Val Val Met Thr Gln Ile Pro Leu Ser Leu Pro Val Ser Leu Gly
                165                 170                 175

Asp Gln Ala Ser Ile Ser Cys Arg Ser Ser Gln Ser Leu Val His Ser
            180                 185                 190

Asn Gly Asn Thr Tyr Leu His Trp Tyr Leu Gln Lys Pro Gly Gln Ser
        195                 200                 205

Pro Lys Leu Leu Ile Tyr Lys Val Ser Asn Arg Phe Ser Gly Val Pro

```
                    210                 215                 220
Asp Arg Phe Ser Gly Ser Gly Ser Gly Thr Asp Phe Thr Leu Lys Ile
225                 230                 235                 240

Ser Arg Val Glu Ala Glu Asp Leu Gly Val Tyr Phe Cys Ser Gln Ser
                    245                 250                 255

Thr His Val Pro His Thr Phe Gly Gly Gly Thr Lys Leu Glu Ile Lys
                260                 265                 270

Arg Thr Val Ala Ala Pro Ser Val Phe Ile Phe Pro Pro Ser Asp Glu
                275                 280                 285

Gln Leu Lys Ser Gly Thr Ala Ser Val Val Cys Leu Leu Asn Asn Phe
            290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335

Thr Tyr Ser Leu Ser Ser Thr Leu Thr Leu Ser Lys Ala Asp Tyr Glu
                340                 345                 350

Lys His Lys Val Tyr Ala Cys Glu Val Thr His Gln Gly Leu Ser Ser
            355                 360                 365

Pro Val Thr Lys Ser Phe Asn Arg Gly Glu Cys
        370                 375

<210> SEQ ID NO 34
<211> LENGTH: 585
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: mature heavy chain of B-4H6/3H3-hFc**
      bispecific antibody

<400> SEQUENCE: 34

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Val Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Gly Glu Phe Asp Tyr Tyr Gly Ser Ser Leu Leu Ser Tyr His
            100                 105                 110

Ser Met Asn Phe Trp Gly Gln Gly Thr Ser Val Thr Val Ser Ser Ala
        115                 120                 125

Ser Gly Ser Gly Gly Gly Gly Ser Gly Gly Gly Ser Gly Gly Gly
    130                 135                 140

Gly Ser Asp Ile Gln Met Thr Gln Thr Thr Ser Ser Leu Ser Ala Ser
145                 150                 155                 160

Leu Gly Asp Arg Val Thr Ile Ser Cys Arg Ala Ser Gln Asp Ile Ser
                165                 170                 175
```

-continued

```
Asn Tyr Leu Asn Trp Tyr Gln Arg Lys Pro Asp Gly Thr Val Lys Leu
            180                 185                 190
Leu Ile Tyr Tyr Thr Ser Arg Leu His Ser Gly Val Pro Ser Arg Phe
        195                 200                 205
Ser Gly Ser Gly Ser Gly Thr Asp Tyr Ser Leu Thr Ile Ser Asn Leu
    210                 215                 220
Glu Gln Glu Asp Ile Ala Thr Tyr Phe Cys Gln Gln Gly Asn Thr Leu
225                 230                 235                 240
Pro Phe Thr Phe Gly Ser Gly Thr Lys Leu Glu Ile Lys Ser Ser Ala
                245                 250                 255
Ser Thr Lys Gly Pro Ser Val Phe Pro Leu Ala Pro Ser Ser Lys Ser
            260                 265                 270
Thr Ser Gly Gly Thr Ala Ala Leu Gly Cys Leu Val Lys Asp Tyr Phe
        275                 280                 285
Pro Glu Pro Val Thr Val Ser Trp Asn Ser Gly Ala Leu Thr Ser Gly
    290                 295                 300
Val His Thr Phe Pro Ala Val Leu Gln Ser Ser Gly Leu Tyr Ser Leu
305                 310                 315                 320
Ser Ser Val Val Thr Val Pro Ser Ser Ser Leu Gly Thr Gln Thr Tyr
                325                 330                 335
Ile Cys Asn Val Asn His Lys Pro Ser Asn Thr Lys Val Asp Lys Arg
            340                 345                 350
Val Glu Pro Lys Ser Cys Asp Lys Thr His Thr Cys Pro Pro Cys Pro
        355                 360                 365
Ala Pro Glu Leu Leu Gly Gly Pro Ser Val Phe Leu Phe Pro Pro Lys
    370                 375                 380
Pro Lys Asp Thr Leu Met Ile Ser Arg Thr Pro Glu Val Thr Cys Val
385                 390                 395                 400
Val Val Asp Val Glu His Glu Asp Pro Glu Val Lys Phe Asn Trp Tyr
                405                 410                 415
Val Asp Gly Val Glu Val His Asn Ala Lys Thr Lys Pro Arg Glu Glu
            420                 425                 430
Gln Tyr Asn Ser Thr Tyr Arg Val Val Ser Val Leu Thr Val Leu His
        435                 440                 445
Gln Asp Trp Leu Asn Gly Lys Glu Tyr Lys Cys Lys Val Ser Asn Lys
    450                 455                 460
Ala Phe Pro Ala Pro Ile Glu Lys Thr Ile Ser Lys Ala Lys Gly Gln
465                 470                 475                 480
Pro Arg Glu Pro Gln Val Tyr Thr Leu Pro Pro Ser Arg Glu Glu Met
                485                 490                 495
Thr Lys Asn Gln Val Ser Leu Thr Cys Leu Val Lys Gly Phe Tyr Pro
            500                 505                 510
Ser Asp Ile Ala Val Glu Trp Glu Ser Asn Gly Gln Pro Glu Asn Asn
        515                 520                 525
Tyr Lys Thr Thr Pro Pro Val Leu Asp Ser Asp Gly Ser Phe Phe Leu
    530                 535                 540
Tyr Ser Lys Leu Thr Val Asp Lys Ser Arg Trp Gln Gln Gly Asn Val
545                 550                 555                 560
Phe Ser Cys Ser Val Met His Glu Ala Leu His Asn His Tyr Thr Gln
                565                 570                 575
Lys Ser Leu Ser Leu Ser Pro Gly Lys
            580                 585
```

```
<210> SEQ ID NO 35
<211> LENGTH: 360
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: mature light chain of B-4H6/3H3-hFc**
      bispecific antibody

<400> SEQUENCE: 35

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Arg Leu Thr Ser Glu Asp Ser Ala Val Tyr Tyr Cys
                85                  90                  95

Ala Arg Gly Gly Ile Asn Tyr Asp Tyr Leu Tyr Tyr Phe Asp Tyr Trp
            100                 105                 110

Gly Gln Gly Thr Thr Leu Thr Val Ser Ser Ala Ser Gly Ser Gly Gly
        115                 120                 125

Gly Gly Ser Gly Gly Gly Gly Ser Gly Gly Gly Gly Ser Asp Val Val
    130                 135                 140

Met Thr Gln Ile Pro Leu Ser Leu Pro Val Ser Leu Gly Asp Gln Ala
145                 150                 155                 160

Ser Ile Ser Cys Arg Ser Ser Gln Ser Leu Val His Ser Asn Gly Asn
                165                 170                 175

Thr Tyr Leu His Trp Tyr Leu Gln Lys Pro Gly Gln Ser Pro Lys Leu
            180                 185                 190

Leu Ile Tyr Lys Val Ser Asn Arg Phe Ser Gly Val Pro Asp Arg Phe
        195                 200                 205

Ser Gly Ser Gly Ser Gly Thr Asp Phe Thr Leu Lys Ile Ser Arg Val
    210                 215                 220

Glu Ala Glu Asp Leu Gly Val Tyr Phe Cys Ser Gln Ser Thr His Val
225                 230                 235                 240

Pro His Thr Phe Gly Gly Gly Thr Lys Leu Glu Ile Lys Arg Thr Val
                245                 250                 255

Ala Ala Pro Ser Val Phe Ile Phe Pro Pro Ser Asp Glu Gln Leu Lys
            260                 265                 270

Ser Gly Thr Ala Ser Val Val Cys Leu Leu Asn Asn Phe Tyr Pro Arg
        275                 280                 285

Glu Ala Lys Val Gln Trp Lys Val Asp Asn Ala Leu Gln Ser Gly Asn
    290                 295                 300

Ser Gln Glu Ser Val Thr Glu Gln Asp Ser Lys Asp Ser Thr Tyr Ser
305                 310                 315                 320

Leu Ser Ser Thr Leu Thr Leu Ser Lys Ala Asp Tyr Glu Lys His Lys
                325                 330                 335

Val Tyr Ala Cys Glu Val Thr His Gln Gly Leu Ser Ser Pro Val Thr
            340                 345                 350
```

Lys Ser Phe Asn Arg Gly Glu Cys
        355                 360

<210> SEQ ID NO 36
<211> LENGTH: 17
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: linker

<400> SEQUENCE: 36

Gly Gly Gly Gly Ser Gly Gly Gly Gly Ser Gly Gly Gly Gly Ser Gly
1               5                   10                  15

Ser

<210> SEQ ID NO 37
<211> LENGTH: 19
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: linker

<400> SEQUENCE: 37

Ala Ser Gly Ser Gly Gly Gly Ser Gly Gly Gly Gly Ser Gly Gly Gly
1               5                   10                  15

Gly Gly Ser

<210> SEQ ID NO 38
<211> LENGTH: 13
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: linker

<400> SEQUENCE: 38

Ala Ser Thr Lys Gly Pro Ser Val Phe Pro Leu Ala Pro
1               5                   10

<210> SEQ ID NO 39
<211> LENGTH: 13
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: linker

<400> SEQUENCE: 39

Arg Thr Val Ala Ala Pro Ser Val Ile Phe Ile Pro Pro
1               5                   10

<210> SEQ ID NO 40
<211> LENGTH: 19
<212> TYPE: PRT
<213> ORGANISM: Artificial sequence
<220> FEATURE:
<223> OTHER INFORMATION: Synthesized
<220> FEATURE:

```
<221> NAME/KEY: MISC_FEATURE
<223> OTHER INFORMATION: linker

<400> SEQUENCE: 40

Ala Ser Gly Ser Gly Gly Gly Gly Ser Gly Gly Gly Gly Ser Gly Gly
1               5                   10                  15

Gly Gly Ser

<210> SEQ ID NO 41
<211> LENGTH: 8
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<223> OTHER INFORMATION: FLAG peptide

<400> SEQUENCE: 41

Asp Tyr Lys Asp Asp Asp Asp Lys
1               5
```

HIGHLY POTENT ANTIBODIES BINDING TO DEATH RECEPTOR 5

CROSS-REFERENCE TO RELATED APPLICATIONS

The present application is a divisional of U.S. Ser. No. 15/772,014 filed Apr. 27, 2018, which is a US national stage of PCT/US16/59517 filed Oct. 28, 2016, which claims the benefit of provisional application No. 62/248,782 filed Oct. 30, 2015, each incorporated by reference in its entirety for all purposes.

REFERENCE TO A SEQUENCE LISTING

This application includes an electronic sequence listing in a file named 552519SEQLST.txt, created Feb. 2, 2021, and containing 43,894 bytes, which is hereby incorporated by reference in its entirety for all purposes.

FIELD OF THE INVENTION

The present invention relates generally to the combination of monoclonal antibody (mAb) and recombinant DNA technologies for developing novel biologics, and more particularly, for example, to the production of monoclonal antibodies that bind and activate death receptors 4 and 5.

BACKGROUND OF THE INVENTION

Tumor necrosis factor-related apoptosis inducing ligand (TRAIL, also known as Apo2 ligand, and also designated as Apo2L or Apo2L/TRAIL) is a member of the TNF ligand superfamily (reviewed in IAM van Roosmalen et al., Biochem Pharmacol 91:447-456, 2014). TRAIL is expressed on many cells of the immune system in a stimulus dependent manner and modulates immune responses, for example as a key effector molecule in NK cell mediated cytotoxicity (C Falschlehner et al., Immunol 127:145-154, 2009). TRAIL activates the extrinsic apoptotic pathway by binding to the cell membrane receptors death receptor 4 (DR4, also called TRAIL-R1) and/or death receptor 5 (DR5, also called TRAIL-R2 or Apo2), thus inducing killing of susceptible cells. More specifically, the active, soluble form of TRAIL is a self-assembling, non-covalent homotrimer that binds the extracellular domain of three receptor molecules with high affinity. This induces oligomerization of the intracellular death domains and formation of homomeric or heteromeric complexes (FC Kischkel et al., Immunity 12:611-620, 2000), followed by recruitment of Fas-associated protein with death domain (FADD) and formation of the death inducing signaling complex (DISC) leading to activation of caspases and then apoptosis, programmed cell death (see van Roosmalen et al., op. cit.). Many cancer cells express DR4 and/or DR5, and TRAIL is able to selectively induce apoptosis of cancer cells (reviewed in J Lemke et al., Cell Death Differ 21: 1350-1364, 2014) and in cross-linked form of tumor endothelial cells (NS Wilson et al., Cancer Cell 22:80-90, 2012). TRAIL itself and various TRAIL-receptor agonists have demonstrated strong antitumor activity against cancer cell lines and in preclinical models (e.g., A Ashkenazi et al., J Clin Invest 104:155-162, 1999). These include recombinant human TRAIL (rhTRAIL; dulanermin) consisting of the extracellular region of human TRAIL (R Pitti et al., J. Biol Chem 271: 12687-12690, 1996), and a number of agonist monoclonal antibodies (mAbs) against DR4 or DR5, including murine, chimeric, humanized and human mAbs (see van Roosmalen et al., op. cit.). Such mAbs include the 4H6.17.8 mAb (designated herein 4H6; U.S. Pat. No. 7,252,994) and mapatumumab (HGS-ETR1; Pukac et al., Br J Cancer 92:1430-1441, 2005) against DR4; and the 3H3.14.5 mAb (designated herein 3H3; U.S. Pat. No. 6,252,050), conatumumab (AMG 655; P Kaplan-Lefko et al., Cancer Biol Ther 9:618-631, 2010), drozitumab (Apomab; C Adams et al., Cell Death Differ 15:751-761, 2008), lexatumumab (HGS-ETR2; G Georgakis et al., Br J Haematol 130:501-510, 2005) and TRA-8 and its humanized form tigatuzumab (CS-1008, A Yada et al., Ann Oncol 19:1060-1067, 2008) against DR5; as well as other mAbs listed in van Roosmalen, op. cit. (see Table 1 on p. 450).

However, while all these agents are very effective at killing tumor cells in vitro and generally in animal models (see references cited above), none of them has demonstrated strong activity in clinical trials, whether used alone or in combination with other agents, and none has advanced into Phase III (reviewed in P M Holland, Cytokine Growth Factor Rev 25:185-193, 2014, and in Lemke et al., op cit. See especially Table 1 in Holland and Tables 2 and 3 in Lemke et al., and references cited therein). For the mAbs, one reason may be the requirement for cross-linking of the mAbs to oligomerize the death receptors to trigger the apoptosis pathway. Such a requirement could be satisfied in vivo by binding of the Fc domain of the mAbs to Fc gamma receptors (FcγR) on immune cells, but there may be too few immune cells infiltrating the tumors or such binding may not be of high enough affinity. Cancer cells may also express inhibitors of apoptosis proteins (see Lemke et al., op. cit.). To improve efficacy, modified forms of TRAIL are being developed, including fusions with other protein domains to enhance stability, oligomerization and/or targeting (Lemke et al., op cit. and Holland, op. cit.). Similarly, constructs comprising multiple antibody binding domains to DR4 and/or DR5 have been developed (K Miller et al., J Immunol 170:4854-4861, 2003; W Wang et al., Immunol Cell Biol 91:360-367, 2013; JE Allen et al., Mol Cancer Ther 11:2087-95, 2012; H Huet et al., Cancer Res 72 abstract 3853, 2012; WO 2014/022592; WO 2015/017822) but have either not entered or not been successful in clinical trials (K P Papadopoulos et al., Cancer Chemother Pharmacol; Feb. 27, 2015, PMID: 25721064); their very unnatural structure may limit their clinical utility. In another approach, combination or co-administration of TRAIL and the anti-DR5 mAb AMG 655 was more effective than either agent alone in vitro and in vivo (JD Graves et al., Cancer Cell 26:177-189, 2014).

SUMMARY OF THE CLAIMED INVENTION

The invention provides monoclonal antibodies (mAbs) that bind to DR4 and DR5, such as D114 and G4.2 and their humanized forms. In one embodiment, the invention provides a bispecific monoclonal antibody comprising two pairs of a heavy chain and a light chain, wherein each heavy/light chain pair comprises a domain that binds to DR4 and a domain that binds to DR5. In other embodiments, the invention provides a multimeric monoclonal antibody that has four binding domains for DR4, or four binding domains for DR5. In preferred embodiments, the antibody has the form of a Bs(scFv)$_4$-IgG antibody as this term is defined below. In any of the bispecific or multimeric mAbs, each binding domain is preferably from a humanized or human mAb, such as humanized forms of D114 and G4.2. Also, any mAb of the invention can contain a constant region comprising mutations that enhance binding to a cellular Fc gamma receptor (FcγR), for example FcγRIIb, e.g., the S267E and/or L328F mutations in a gamma-1 constant region (according to Kabat numbering with EU index), preferably two or more such mutations. Advantageously, the mAb inhibits growth of a human tumor xenograft in a mouse. In another aspect, a pharmaceutical composition comprising any of these mAbs is provided. In a third aspect, such a pharmaceutical composition is administered to a patient to treat cancer or other disease.

BRIEF DESCRIPTION OF THE DRAWINGS

FIGS. 1A, B. Schematic diagrams of the Bs(scFv)$_4$-IgG antibody format showing individual variable and constant regions (A) or the domains formed by folding together of each light chain region with respective heavy chain region (B). $V_H1$ (respectively $V_L1$)=heavy (resp. light) chain variable region of first antibody; and similarly for $V_H2$ and $V_L2$ of second antibody. $C_H1$, $C_H2$, $C_H3$ (resp. $C_L$)=heavy (resp. light) constant region regions; H=hinge region. V1 (resp. V2)=full variable domain of first (resp. second) antibody.

FIGS. 2A-D. (A) Graph showing binding of 4H6 and D114 mAbs to DR4. (B) Graph showing inhibition of binding of Apo2L to DR4 by 4H6 and D114 mAbs. (C) Graph showing binding of 3H3 and G4.2 mAbs to DR5. (D) Graph showing inhibition of binding of Apo2L to DR5 by 3H3 and G4.2 mAbs. mIgG is mouse negative control mAb.

FIGS. 3A-D. Cell viability of H60 lung tumor cells (A) and SW480 colon tumor cells (B) after treatment with 4H6 and D114 mAbs in the presence of goat anti-mouse IgG-Fc antibody (anti-mIgG-Fc); cell viability of H60 lung tumor cells (C) and COLO 205 colon tumor cells (D) after treatment with 3H3 and G4.2 mAbs in the presence of anti-mIgG-Fc.

FIGS. 4A-D. Amino acid sequences of the mature heavy (A) and light (B) chain variable regions of the 4H6 mAb, and of the mature heavy (C) and light (D) chain variable regions of the 3H3 mAb, using the 1-letter code (SEQ ID NOS:1-4 respectively).

FIGS. 5A-D. Amino acid sequences of the mature variable regions of the HuD114-L1 light chain (A) and HuD114-H1 and HuD114-H2 heavy chains (B) are shown aligned with mouse D114 and human acceptor V regions; and amino acid sequences of the mature variable regions of the HuG4.2-L1 and HuG4.2-L2 light chains (C) and HuG4.2-H1 and HuG4.2-H2 heavy chains (D) are shown aligned with mouse G4.2 and human acceptor V regions. The sequences are designated (A) SEQ ID NOS. 5-7, (B) SEQ ID NOS. 8-11, (C) SEQ ID NOS. 12-15, and (D) SEQ ID NOS. 16-19. The CDRs are underlined in the D114 (respectively G4.2) sequences. CDR-L1, -L2, -L3, -H1, -H2 and -H3 of D114 are designated SEQ ID NOS. 20-25 respectively and of G4.2 are designated SEQ ID NOS. 26-31) and the amino acids substituted with mouse D114 (resp. G4.2) amino acids are double underlined in the HuD114 (resp. HuG4.2) sequences. The 1-letter amino acid code and Kabat numbering system are used for both the light and heavy chain in all figures herein.

FIGS. 6A, B. Amino acid sequences (1-letter code) of the complete heavy (A) and light (B) chains of the B-3H3/4H6-hFc** bispecific antibody (SEQ ID NOS. 32 and 33), including signal peptides that are cleaved off and thus not present in the mature proteins, which mature proteins are designated SEQ ID NOS: 34 and 35. Arrows under the sequences separate in order the signal peptide (shown struck through), 4H6 $V_H$ region (A) or respectively 3H3 $V_H$ region (B), linker sequence (shown underlined), 4H6 $V_L$ region (A) or respectively 3H3 $V_L$ region (B), and heavy chain (A) or light chain (B) constant region. The mutated amino acids 267E and 328F are double underlined.

FIGS. 7A, B. Cell viability of SW480 colon tumor cells after treatment by the indicated agents in the absence (A) and presence (B) of goat anti-hIgG-Fc, as measured by a WST-8 assay. hIgG is control human mAb in the figures herein.

FIGS. 8A, B. Cell viability of H460 lung tumor cells after treatment by the indicated agents without goat anti-hIgG-Fc (A) and in the presence of human PBMCs (B).

FIGS. 9A, B. (A) Cell viability of COLO 205 colon tumor cells after incubation with 0.5 µg/mL of the indicated agents with PBMCs from 4 human donors. (B) Cell viability of the indicated cells after incubation with 1.0 µg/mL of the indicated agents with PBMCs. Error bars are standard error of the mean (SEM) in the figures herein.

FIGS. 10A, B. (A) Cell viability of COLO 205 cells after treatment by the indicated agents in the presence of PBMCs (short dashes, 4H6-hFc; long dashes, 4H6-hFc*). (B) Inhibition of growth of COLO 205 colon tumor xenografts by the indicated agents.

FIGS. 11A-C. Inhibition of growth of COLO 205 colon tumor xenografts (A, C) and SW480 colon tumor xenografts (B) by the indicated agents FIGS. 12A, B. Inhibition of growth of COLO 205 colon tumor xenografts (A) and MIA PaCa-2 pancreatic tumor xenografts (B) by the indicated agents.

FIGS. 13A, B. Graphs showing binding of the indicated anti-DR4 mAbs to DR4 (A) and anti-DR5 mAbs to DR5 (B). In all figure legends herein, the -Fc and -Fc suffixes mean the same as -hFc and -hFc respectively (e.g., HuD114-Fc #1 means the same as HuD114-hFc #1, etc.) In this and the following figures, as indicated by the legends, generally solid lines denote the hFc** form of mAbs, dashed lines denote the hFc or hFc* form, and dotted lines denote mouse mAbs.

FIGS. 14A, B. Cell viability of COLO 205 colon tumor cells after treatment by anti-DR4 mAbs (A) and anti-DR5 mAbs (B) in the presence of goat anti-hIgG-Fc. Different concentration units are used in (A) and (B).

FIGS. 15A-D. Cell viability of COLO 205 colon tumor cells (A), SW480 colon tumor cells (B), COLO 205 cells (C) and MIA PaCa-2 pancreatic tumor cells (D) after treatment by the indicated mAbs, in the presence of anti-mIgG-Fc in the case of the mouse TRA-8 mAb or goat anti-hIgG-Fc in the case of humanized or human mAbs.

FIGS. 16A-B. Cell viability of H60 lung tumor cells (A) and SW480 colon tumor cells (B) after treatment by the indicated agents in the presence of goat anti-hIgG-Fc.

FIGS. 17A-F. Cell viability of COLO 205 colon tumor cells (A, C and E) and H60 lung tumor cells (B, D, and F) after treatment by the indicated agents in the presence of human PBMCs.

FIGS. 18A-D. Inhibition of growth of COLO 205 colon tumor xenografts (A), H60 lung tumor xenografts (B), COLO 205 xenografts (C), and Ramos lymphoma xenografts (D) by the indicated agents.

FIGS. 19A, B. Inhibition of growth of COLO 205 colon tumor xenografts (A) and MIA PaCa-2 pancreatic tumor xenografts (B) by the indicated agents.

FIGS. 20A-D. (A, C) Results of ELISA assay measuring simultaneous binding of each indicated agent to DR4 and DR5. In (A), the curves for 4H6-hFc and 3H3-hFc superimpose and cannot be distinguished. (B, D) Cell viability of COLO 205 cells after treatment by the indicated agents in the absence of goat anti-mIgG-Fc.

DETAILED DESCRIPTION OF THE PREFERRED EMBODIMENTS

1. Antibodies

Figure 11C:
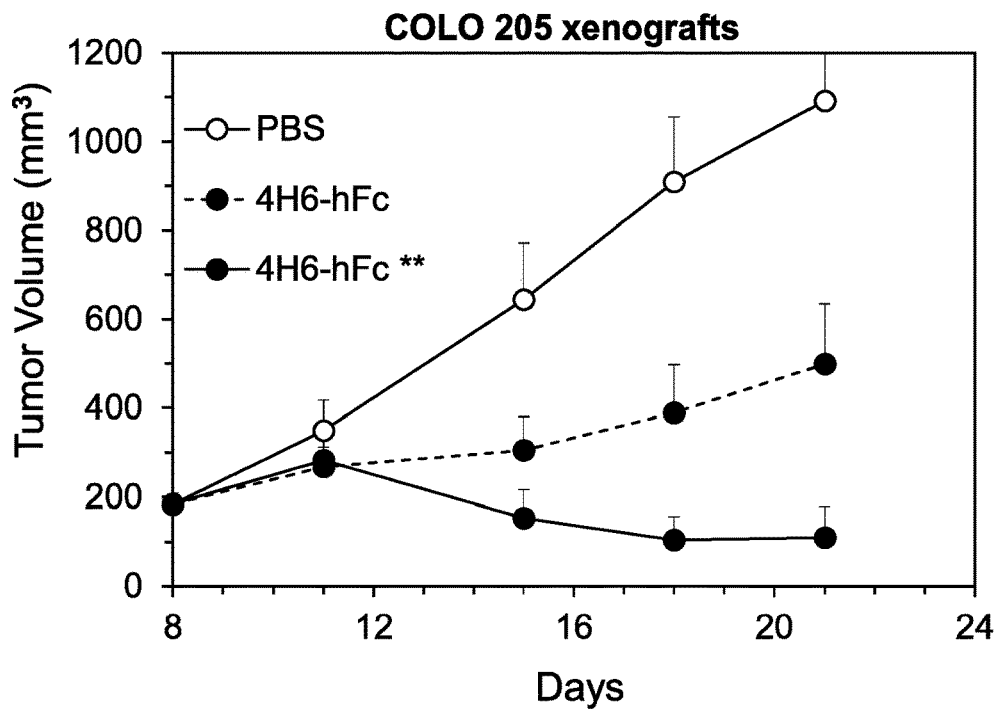

As used herein, "antibody" means a protein containing one or more domains capable of binding an antigen, where such domain(s) are derived from or homologous to the variable domain of a natural antibody. A monoclonal antibody ("mAb") is simply a unique species of antibody, in contrast to a mixture of different antibodies. The antibodies described herein are generally monoclonal, unless otherwise indicated by the context. An "antigen" of an antibody means a compound to which the antibody specifically binds and is typically a polypeptide, but can also be a small peptide or small-molecule hapten or carbohydrate or other moiety. Examples of antibodies include natural, full-length tetrameric antibodies; antibody fragments such as Fv, Fab, Fab' and (Fab')$_2$; single-chain (scFv) antibodies (Huston et al., Proc. Natl. Acad. Sci. USA 85:5879, 1988; Bird et al., Science 242:423, 1988); single-arm antibodies (Nguyen et al., Cancer Gene Ther 10:840, 2003); and bispecific, chimeric and humanized antibodies, as these terms are further explained below. Antibodies may be derived from any vertebrate species, including chickens, rodents (e.g., mice, rats and hamsters), rabbits, camels, primates and humans. An antibody comprising a constant domain may be of any of the known isotypes IgG, IgA, IgM, IgD and IgE and their subtypes, e.g., human IgG1, IgG2, IgG3, IgG4 and mouse IgG1, IgG2a, IgG2b, and IgG3, and their allotypes and isoallotypes, including permutations of residues occupying polymorphic positions in allotypes and isoallotypes. An antibody can also be of chimeric isotype, that is, one or more of its constant (C) regions can contain regions from different isotypes, e.g., a gamma-1 $C_H1$ region together with hinge, $C_H2$ and/or $C_H3$ domains from the gamma-2, gamma-3 and/or gamma-4 genes. The antibody may also contain replacements in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc Natl Acad Sci USA 103:4005, 2006), or to prolong half-life in humans (see, e.g., Hinton et al., J Biol Chem 279:6213, 2004).

A natural antibody molecule is generally a tetramer consisting of two identical heterodimers, each of which comprises one light chain paired with one heavy chain. Each light chain and heavy chain consists of a variable ($V_L$ for the light chain, or $V_H$ for the heavy chain, or V for both) region followed by a constant ($C_L$ or $C_H$, or C) region. The $C_H$ region itself comprises $C_H1$, hinge (H), $C_H2$, and $C_H3$ regions. In 3-dimensional (3D) space, the $V_L$ and $V_H$ regions fold up together to form a V domain, which is also known as a binding domain since it binds to the antigen. The CL region folds up together with the $C_H1$ region, so that the light chain $V_L$-CL and the $V_H$-$C_H1$ region of the heavy chain together form a part of the antibody known as a Fab: a naturally "Y-shaped" antibody thus contains two Fabs, one from each heterodimer, forming the arms of the Y. The $C_H2$ region of one heterodimer is positioned opposite the $C_H2$ region of the other heterodimer, and the respective $C_H3$ regions fold up with each other, forming together the single Fc domain of the antibody (the base of the Y), which interacts with other components of the immune system.

Within each light or heavy chain variable region, there are three short segments (averaging about 10 amino acids in length) called the complementarity determining regions ("CDRs"). The six CDRs in an antibody variable domain (three from the light chain and three from the heavy chain) fold up together in 3D space to form the actual antibody binding site which locks onto the target antigen. The position and length of the CDRs have been precisely defined by E Kabat et al., Sequences of Proteins of Immunological Interest, U.S. Department of Health and Human Services, 1983, 1987, 1991. The part of a variable region not contained in the CDRs is called the framework, which forms the environment for the CDRs. Chothia et al., J. Mol. Biol. 196:901, 1987, have defined the related concept of hypervariable regions or loops determined by structure.

As used herein, a "genetically engineered" mAb is one for which the genes have been constructed or put in an unnatural environment (e.g., human genes in a mouse or on a bacteriophage) with the help of recombinant DNA techniques, and therefore includes chimeric antibodies and humanized antibodies, as described below, but would not encompass a mouse or other rodent mAb made with conventional hybridoma technology. A chimeric antibody (or respectively chimeric antibody light or heavy chain) is an antibody (or respectively antibody light or heavy chain) in which the variable region of a mouse (or other non-human species) antibody (or respectively antibody light or heavy chain) is combined with the constant region of a human antibody; their construction by means of genetic engineering is well-known. Such antibodies retain the binding specificity of the mouse antibody, while being about two-thirds human.

A humanized antibody is a genetically engineered antibody in which CDRs from a non-human "donor" antibody (e.g., chicken, mouse, rat, rabbit or hamster) are grafted into human "acceptor" antibody sequences, so that the humanized antibody retains the binding specificity of the donor antibody (see, e.g., Queen, U.S. Pat. No. 5,530,101 and Winter, U.S. Pat. No. 5,225,539; Carter, U.S. Pat. No. 6,407,213; Adair, U.S. Pat. Nos. 5,859,205 6,881,557; Foote, U.S. Pat. No. 6,881,557). The acceptor antibody sequences can be, for example, a mature human antibody sequence, a consensus sequence of human antibody sequences, a germline human antibody sequence, or a composite of two or more such sequences. Thus, a humanized antibody is an antibody having some or all CDRs entirely or substantially from a donor antibody and variable region framework sequences and constant regions, if present, entirely or substantially from human antibody sequences. Similarly, a humanized light chain (respectively heavy chain) has at least one, two and usually all three CDRs entirely or substantially from a donor antibody light (resp. heavy) chain, and a light (resp. heavy) chain variable region framework and light (resp. heavy) chain constant region, if present, substantially from a human light (resp. heavy) acceptor chain. A humanized antibody generally comprises a humanized heavy chain and a humanized light chain. A CDR in a humanized antibody is substantially from a corresponding CDR in a non-human antibody when at least 85%, 90%, 95% or 100% of corresponding amino acids (as defined by Kabat) are identical between the respective CDRs. The variable region framework or constant region of an antibody chain are substantially from a human variable region or human constant region respectively when at least 85, 90, 95 or 100% of corresponding amino acids (as defined by Kabat) are identical.

Here, as elsewhere in this application, percentage sequence identities are determined with antibody sequences maximally aligned by the Kabat numbering convention (Eu index for the $C_H$ region). After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

In order to retain high binding affinity in a humanized antibody, at least one of two additional structural elements can be employed. See, U.S. Pat. No. 5,530,101 and incorporated herein by reference, which provide detailed instructions for construction of humanized antibodies. In the first structural element, the framework of the heavy chain variable region of the acceptor or humanized antibody is chosen to have high sequence identity (between 65% and 95%) with the framework of the heavy chain variable region of the donor antibody, by suitably selecting the acceptor antibody heavy chain from among the many known human antibodies. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are chosen on the basis of their ability to interact with the CDRs. For example, the replaced amino acids can be adjacent to a CDR in the donor antibody sequence or within 4-6 angstroms of a CDR in the humanized antibody as measured in 3-dimensional space.

Other approaches to design humanized antibodies may also be used to achieve the same result as the methods in U.S. Pat. Nos. 5,530,101 and 5,585,089 described above, for example, "superhumanization" (see Tan et al. J Immunol 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641. Veneered antibodies are made more human-like by replacing specific amino acids in the variable region frameworks of the non-human donor antibody that may contribute to B- or T-cell epitopes, for example exposed residues (Padlan, Mol. Immunol. 28:489, 1991). Other types of genetically engineered antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or by using transgenic animals (Lonberg et al., WO93/12227; Kucherlapati WO91/10741, each of which is incorporated herein by reference).

The terms "antibody" or "mAb" also encompass bispecific antibodies. A "bispecific antibody" is an antibody that contains a first domain binding to a first antigen and a second (different) domain binding to a second antigen, where the first and second domains are derived from or homologous to variable domains of natural antibodies. The first antigen and second antigen may be the same antigen, in which case the first and second domains can bind to different epitopes on the antigen. The term bispecific antibody encompasses multispecific antibodies, which in addition to the first and second domains contain one or more other domains binding to other antigens and derived from or homologous to variable domains of natural antibodies. The term bispecific antibody also encompasses an antibody containing a first binding domain derived from or homologous to a variable domain of a natural antibody, and a second binding domain derived from another type of protein, e.g., the extracellular domain of a receptor, (a "bispecific antibody-immunoadhesin"). And the term bispecific antibody further encompasses a "two-in-one" antibody with a dual specificity binding domain (G Schaefer et al., Cancer Cell 20:472-486, 2011).

Bispecific antibodies have been produced in a variety of forms (see, e.g., Kontermann, MAbs 4:182-197, 2012 and references cited therein), for example single chain variable fragment (scFv), Fab-scFv, and scFv-scFv fusion proteins (Coloma et al., Nat Biotechnol 15:125-126, 1997; Lu et al., J Immunol Methods 267:213-226, 2002; Mallender, J Biol Chem 269:199-206, 1994), Bs(scFv)$_4$-IgG (Z Zuo et al., Protein Eng 13: 361-367, 2000), double variable domain antibodies (C Wu et al., Nat Biotechnol 25:1290-1297, 2007), and diabodies (Holliger et al., Proc Natl Acad Sci USA 90:6444-6448, 1993). Bispecific F(ab')2 antibody fragments have been produced by chemical coupling (Brennan et al., Science 229:81, 1985) or by using leucine zippers (Kostelny et al., J Immunol 148:1547-1553, 1992). A more naturally shaped bispecific antibody, with each heavy chain-light chain pair having a different V region, can be made, e.g., by chemically cross-linking the two heavy chain-light chain pairs produced separately (Karpovsky et al., J Exp Med 160:1686-1701, 1984), Naturally shaped bispecific antibodies can also be produced by expressing both required heavy chains and light chains in a single cell, made by fusing two hybridoma cell lines (a "quadroma"; Milstein et al., Nature 305: 537-540) or by transfection. Association of the correct light and heavy chains expressed in a cell to form the desired bispecific antibody can be promoted by using "knobs-into-holes" technology (Ridgway et al., Protein Eng 9:617-621, 1996; Atwell et al., J Mol Biol 270:26-1997; and U.S. Pat. No. 7,695,936); optionally with exchange or "crossing over" of heavy chain and light chain domains within the antigen binding fragment (Fab) of one light chain-heavy chain pair, thus creating bispecific antibodies called "CrossMabs" (Schaefer et al., Proc Natl Acad Sci USA 108:11187-11192, 2011; WO 2009/080251; WO 2009/080252; WO 2009/080253).

Related to the concept of bispecific antibodies are "multimeric" antibodies, which are mAbs that contain more than two binding domains, each binding to the same antigen. Many of the formats for bispecific mAbs, for example Bs(scFv)$_4$-IgG and double variable domain, may be adapted to make multimeric mAbs by using the same variable domain as each binding domain. So for example, a multimeric Bs(scFv)$_4$-IgG antibody would contain 4 copies of the same binding domain.

An antibody is said to bind "specifically" to an antigen if it binds to a significantly greater extent than irrelevant antibodies not binding the antigen, and thus typically has binding affinity (K a) of at least about $10^6$ but preferably $10^7$, $10^8$, $10^9$ or $10^{10}$ $M^{-1}$ for the antigen. Generally, when an antibody is said to bind to an antigen, specific binding is meant. If an antibody is said not to bind an antigen, it is meant that any signal indicative of binding is not distinguishable within experimental error from the signal of irrelevant control antibodies. The epitope of a mAb is the region of its antigen to which the mAb binds. Two antibodies are judged to bind to the same or overlapping epitopes if each competitively inhibits (blocks) binding of the other to the antigen. Competitively inhibits binding means that a 1× or 5× excess of one antibody inhibits binding of the other by at least 50% but preferably 75%, or that a 10×, 20× or 100× excess of one antibody inhibits binding of the other by at least 75% but preferably 90% or even 95% or 99% as measured in a competitive binding assay (see, e.g., Junghans et al., Cancer Res. 50:1495, 1990). One mAb (the second mAb) is said to "fully" compete for binding an antigen with another mAb (the first mAb) if the inhibitory concentration 50 (IC50) of the second mAb to inhibit binding (of the first mAb) is comparable to, that is, within 2-fold or 3-fold, of the IC50 of the first mAb to inhibit binding of itself, in competitive binding assays. A second mAb is said to "partially" compete for binding an antigen with a first mAb if the IC50 of the second mAb to inhibit binding (of the first mAb) is substantially greater than, e.g., greater than 3-fold or 5-fold or 10-fold, the IC50 of the first mAb to inhibit binding. In general, two mAbs have the same epitope on an antigen if each fully competes for binding to the antigen with the other, and have overlapping epitopes if at least one mAb partially competes for binding with the other mAb. Alternatively, two antibodies have the same epitope if essentially all amino acid mutations in the antigen that reduce or eliminate binding of one antibody reduce or eliminate binding of the other, while two antibodies have overlapping epitopes if some amino acid mutations that reduce or eliminate binding of one antibody reduce or eliminate binding of the other.

2. Anti-DR4 and anti-DR5 Antibodies

A monoclonal antibody that binds DR4, (i.e., an anti-DR4 mAb), or respectively an antibody that binds DR5 (i.e., an anti-DR5 mAb) is said to be agonist if binding of the mAb to the cell membrane receptor DR4 or respectively DR5 transmits an apoptotic signal to at least some types of cells, thus inducing apoptosis. Such an antibody may be blocking or non-blocking, i.e., inhibit or not inhibit binding of Apo2L/TRAIL to DR4 or DR5 respectively. An agonist mAb of the invention, which may be a bispecific antibody binding to either DR4 and DR5 and a second antigen, or to both DR4 and DR5, at a concentration of, e.g., 0.1, 1, 10, 100, 1000, or 10,000 ng/mL, inhibits cell viability or induces apoptosis by approximately 25%, 50%, 75%, 90%, 95%, 99% or more, as measured for example by inhibition of cellular metabolism, e.g., using the WST-8 assay. Such cell line may for example be the COLO 205 or SW480 colon tumor lines, H460 lung cancer line, or BxPC-3 pancreatic cancer cell line. Such activity may be obtained by use of the mAb alone, or in the presence of either human cells such as peripheral blood mononuclear cells or of an antibody that cross-links the mAb, for example goat anti-IgG-Fc (at e.g., 10 μg/mL). The activity is typically measured after incubation of the mAb plus cells plus any other agents overnight at 37° C.

MAbs to be used in the present invention are preferably specific for DR4 or respectively DR5, that is they do not (specifically) bind, or only bind to a much lesser extent (e.g., less than ten-fold), proteins that are related to DR4 or DR5 such as the tumor necrosis factor (TNF) receptors TNFR1 and TNFR2 and other members of the TNFR superfamily, other death receptors such as Apo-1 (Fas), and the decoy receptors DcR1 and DcR2. MAbs to be used in the invention typically have a binding affinity (K a) for DR4 or DR5 of at least $10^7$ $M^{-1}$ but preferably $10^8$ $M^{-1}$ or higher, and most preferably $10^9$ $M^{-1}$, $10^{10}$ $M^{-1}$ or $10^{11}$ $M^{-1}$ or higher. Such a mAb binds human DR4 or DR5, but advantageously also DR4 or DR5 from other species, e.g., mice or non-human primates such as cynomolgus monkeys, ideally with binding affinity similar to (e.g., within 10-fold) the binding affinity to human DR4 or DR5. The sequence of human DR4 and DR5 are respectively provided, e.g., by G Pan et al., Science. 276:111-113, 1997 (GenBank: AAC51226.1) and H Walczak et al., EMBO J 16:5386-5397, 1997 (GenBank: CAG46696.1).

Exemplary antibodies of the invention are D114 and G4.2 and their chimeric and humanized forms such as HuD114 and HuG4.2. These as well as other anti-DR4 mAbs such as 4H6 (produced by the hybridoma ATCC HB-12455; see U.S. Pat. No. 7,252,994), and anti-DR5 mAbs such as 3H3 (produced by the hybridoma ATCC HB-12534; see U.S. Pat. No. 6,252,050) or other antibody includes all the CDRs of 4H6 or 3H3 can be used in the bispecific and multimeric mAbs of the invention, with chimeric, humanized or human agonist mAbs preferred for such use. Other embodiments of the invention include a preferably agonist anti-DR4 or anti-DR5 mAb—either an ordinary IgG or a bispecific or multimeric antibody—comprising mutations in the constant region that increase binding to an Fc receptor such as a receptor for IgG antibodies (FcγR), e.g., the FcγRIIb receptor, for example the HuD114-hFc and HuG4.2-hFc mAbs described below. Exemplary mutations are the single G236D, L328F, S239D, and S267E mutations, and preferably double mutations such as G236D/S267E, S239D/S267E and most preferably S267E/L328F that provide greater binding affinity to an FcγR than either constituent single mutation (S Y Chu et al., Mol Immunol 45:3926-3933, 2008), as well as other mutations at these amino acid positions, using the Kabat numbering system, which is used to define all amino acid positions set forth herein. Of these, the S267E single mutation has been shown to increase the potency of an anti-DR5 mAb in vitro and in vivo (F Li et al., Proc Natl Acad Sci USA 109:10966-10971, 2012). Most preferably, the mAb of the invention inhibits growth of a human tumor xenograft in a mouse as assessed by any of the assays in the Examples or otherwise known in the art.

MAbs that have CDRs (for example three CDRs in the light chain and three CDRs in the heavy chain), as defined by Kabat, that individually or collectively are at least 90%, 95% or 98% or completely identical to the CDRs of D114 (respectively G4.2) in amino acid sequence and that maintain its functional properties, e.g., a humanized D114 (resp. G4.2) mAb, or which differ from D114 (resp. G4.2) by a small number of functionally inconsequential amino acid substitutions (e.g., conservative substitutions, as defined below), deletions, or insertions are also an embodiment of the invention, with or without the mutations described above.

Once a single, archetypal anti-human-DR4 (respectively anti-human-DR5) mAb, for example D114 (resp. G4.2), has been isolated that has the desired properties described herein, it is straightforward to generate other mAbs with similar properties by using art-known methods, including mAbs that compete with D114 (resp. G4.2) for binding to DR4 (resp. DR5) and/or have the same epitope. For example, mice may be immunized with the extracellular domain of DR4 (resp. DR5), hybridomas produced, and the resulting mAbs screened for the ability to compete with D114 (resp. G4.2) for binding to DR4 (resp. DR5). Mice can also be immunized with a smaller fragment of DR4 (resp. DR5) containing the epitope to which D114 (resp. G4.2) binds. The epitope can be localized by, e.g., screening for binding to a series of overlapping peptides spanning DR4 (resp. DR5). Mouse mAbs generated in these ways can then be humanized. Alternatively, the method of Jespers et al., Biotechnology 12:899, 1994, which is incorporated herein by reference, may be used to guide the selection of mAbs having the same epitope and therefore similar properties to D114 (resp. G4.2). Using phage display, first the heavy chain of D114 (resp. G4.2) is paired with a repertoire of (preferably human) light chains to select a DR4-binding (resp. DR5-binding) mAb, and then the new light chain is paired with a repertoire of (preferably human) heavy chains to select a (preferably human) DR4-binding (resp. DR5-binding) mAb having the same epitope as D114 (resp. G4.2). Alternatively variants of D114 (resp. G4.2) can be obtained by mutagenesis of DNA encoding the heavy and light chains of D114 (resp. G4.2).

Genetically engineered mAbs, e.g., chimeric or humanized or bispecific mAbs, may be expressed by a variety of art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, poly A sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NS0, and cells expressing the antibodies selected by appropriate antibiotic selection. See, e.g., U.S. Pat. No. 5,530,101. Larger amounts of antibody may be produced by growing the cells in commercially available bioreactors. Hence, the invention provides cell lines expressing any of the mAbs described herein.

Once expressed, the mAbs of the invention including bispecific mAbs may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% homogeneity are preferred, and 98% or 99% or more homogeneity most preferred, for pharmaceutical uses. It is also understood that when the mAb is manufactured by conventional procedures, one to several amino acids at the amino or carboxy terminus of the light and/or heavy chain, such as the C-terminal lysine of the heavy chain, may be missing or derivatized in a proportion or all of the molecules, and such a composition is still considered to be the same mAb.

3. Bispecific and Multimeric Antibodies

In one embodiment, the invention provides a bispecific monoclonal antibody comprising at least one binding domain that binds to DR4 and at least one binding domain that binds to DR5. Such an antibody is called a bispecific DR4/DR5 antibody or mAb herein. In preferred embodiments, each binding domain is from a humanized or human mAb. In preferred embodiments, the bispecific antibody comprises two or more binding domains that bind to DR4 and two or more binding domains that bind to DR5; often the two binding domains to DR4 are the same and the two binding domains to DR5 are the same. In any case, the bispecific mAb is preferably agonist as described above, i.e., induces an apoptotic signal through DR4 and/or DR5 in susceptible cells such as cancer cells. Exemplary bispecific mAbs comprise the binding domain of the 4H6 anti-DR4 mAb or the D114 mAb disclosed herein or their humanized forms, and the binding domain of the 3H3 anti-DR5 mAb or the G4.2 mAb disclosed herein or their humanized forms.

The bispecific antibody of the invention may be in any format, such as any of those listed in Kontermann, op. cit. In one preferred embodiment, the bispecific antibody is in the Bs(scFv)$_4$-IgG format described in Zuo et al., op. cit. and illustrated in FIGS. 1A, B. In this format, one binding domain in single chain (scFv) form is connected to the $C_L$ region and thus becomes the N-terminal domain of the light chain, while the other binding domain in scFv form is connected to the $C_H1$ domain and thus becomes the N-terminal domain of the heavy chain; two light chains and two heavy chains form a homodimer as in an ordinary IgG antibody, but containing two of each binding domain. Thus, an advantage of the Bs(scFv)4-IgG format is that it is a homodimer, with the same heavy chain and light chain in each monomer, so that no precautions need to be taken to ensure correct heterodimerization. The linker within each scFv connecting the V.sub.L and V.sub.H regions is often chosen as $(G_4S)_3GS$ (SEQ ID NO:36) or $ASGS(G_4S)_3$ (SEQ ID NO:37). Each scFv binding domain may be in the form $V_L$-linker-$V_H$ or in the form $V_H$-linker-$V_L$ (as shown in FIG. 1A), and either binding domain may be part of the light chain while the other is part of the heavy chain, so in total 2×2×2=8 variants of a Bs(scFv)4-IgG antibody can be made from two given binding domains (e.g., those of HuD114 and HuG4.2), which may have differing properties.

In another embodiment of the invention, the bispecific antibody is in the double variable domain format described in, e.g., Wu et al., op. cit., (see FIG. 1A with labeling therein). Like Bs(scFv)4-IgG mAbs, such a bispecific mAb is a homodimer, with each monomer containing one of each of the binding domains, linked in the sequence V1-V2-constant domain. A variety of peptide linkers may be used to connect the first and second variable regions, e.g., ASTKGPSVFPLAP (SEQ ID NO:38) in the heavy chain and RTVAAPSVIFIPP (SEQ ID NO:39) in the light chain, or $ASGS(G_4S)_3$ (SEQ ID NO:40) in both chains. For example, in such a bispecific mAb, the variable domain of HuG4.2 could be the first domain, the variable domain of HuD114 could be the second domain; the linkers could be the former ones mentioned above, and the constant region could be of the human IgG1, kappa isotype.

In other preferred embodiments of the invention, one monomer of the anti-DR4 mAb comprising a light and heavy chain pairs with one monomer of the anti-DR5 mAb comprising a light and heavy chain to form a heterodimer with the normal configuration of an IgG molecule. If all four chains are to be expressed in a cell, formation of the desired heterodimer bispecific antibodies instead of homodimers is promoted by inserting knobs and holes into the $C_H3$ regions of the respective heavy chains (Ridgway et al., Protein Eng 9:617-21, 1996; Atwell et al., J Mol Biol 270:26-35, 1997; and U.S. Pat. No. 7,695,936), while correct pairing of the light and heavy chains to form each anti-DR4 and anti-DR5 monomer is promoted by "crossing over" of heavy chain and light chain domains within one of the monomers (Schaefer et al., Proc Natl Acad Sci USA 108:11187-92, 2011; WO 2009/080251; WO 2009/080252; WO 2009/080253).

In another embodiment, the invention provides a multimeric antibody containing three or more binding domains for DR4 or three or more binding domains for DR5, e.g., four binding domains. In preferred embodiments, the anti-DR4 or anti-DR5 multimeric mAb is in the Bs(scFv) 4-IgG or double variable domain format, so that it contains precisely four binding domains for DR4 or DR5 respectively.

In especially preferred embodiments of the invention, the bispecific DR4/DR5 or multimeric anti-DR4 or anti-DR5 antibody, in any form including the ones specifically described above such as Bs(scFv)$_4$-IgG and double variable domain, comprises mutations in the constant region that increase binding to an Fc receptor, for example the FcγRIIb receptor. Exemplary mutations are the single G236D, L328F, S239D, S267E mutations, and preferably double mutations G236D/S267E, S239D/S267E, and most preferably S267E/L328F (described in S Y Chu et al., op. cit.), as well as other mutations at these amino acid positions. Any Bs(scFv)$_4$-IgG or double variable domain bispecific antibody with the V1 domain binding to DR5 and the V2 domain binding to DR4 (see FIG. 1B) with natural human constant regions is designated B-DR5/DR4-hFc and is designated B-DR5/DR4-hFc if it further contains the S267E/L328F double mutations; analogously for B-DR4/DR5-hFc and B-DR4/DR5-hFc with V1 binding to DR4 and V2 binding to DR5. A multimeric Bs(scFv)$_4$-IgG or double variable domain antibody in which both V1 and V2 bind to DR4 (resp. DR5) is designated B-DR4/DR4-hFc (resp. B-DR5/DR5-hFc), and as B-DR4/DR4-hFc (resp. B-DR5/DR5-hFc) if it further contains the S267E/L328F mutations.

The invention provides also variant antibodies including bispecific antibodies whose light and heavy chain differ from the ones specifically described herein by a small number (e.g., typically no more than 1, 2, 3, 5 or 10) of replacements, deletions or insertions, usually in the C region or V region framework but possibly in the CDRs. Most often the replacements made in the variant sequences are conservative with respect to the replaced amino acids. Amino acids can be grouped as follows for determining conservative substitutions, i.e., substitutions within a group: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Preferably, replacements in the antibody have no substantial effect on the binding affinity or potency of the antibody, that is, on its ability to transmit an apoptotic signal through DR4 and/or DR5. Preferably the variant sequences are at least 90%, more preferably at least 95%, and most preferably at least 98% identical to the original sequences. In addition, other allotypes or isotypes of the constant regions may be used.

4. Therapeutic Methods

In a preferred embodiment, the present invention provides a pharmaceutical formulation comprising any antibody described herein, for example a B-DR5/DR4-hFc, B-DR5/DR4-hFc, B-DR4/DR5-hFc or B-DR4/DR5-hFc bispecific mAb, or B-DR4/DR4-hFc, B-DR4/DR4-hFc, B-DR5/DR5-hFc or B-DR5/DR5-hFc multimeric mAb, as well as humanized forms of D114 and G4.2 such as HuD114-hFc and HuG4.2-hFc. Pharmaceutical formulations contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art (Remington's Pharmaceutical Science 16th edition, Osol, A. Ed. 1980). The mAb is typically present at a concentration of 0.1-1 mg/kg or 1-100 mg/ml, but most often 10-50 mg/ml, e.g., 10, 20, 30, 40 or 50 mg/ml.

In another preferred embodiment, the invention provides a method of treating a patient with a disease by administering any antibody of the invention, for example a B-DR5/DR4-hFc, B-DR5/DR4-hFc, B-DR4/DR5-hFc or B-DR4/DR5-hFc bispecific mAb, or B-DR4/DR4-hFc, B-DR4/DR4-hFc, B-DR5/DR5-hFc or B-DR5/DR5-hFc multimeric mAb, as well as humanized forms of D114 and G4.2 such as HuD114-hFc and HuG4.2-hFc, in a pharmaceutical formulation, typically in order to destroy harmful cells such as cancer cells expressing DR4 and/or DR5. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given is sufficient to alleviate the condition being treated ("therapeutically effective dose") and is likely to be 0.1 to 5 mg/kg body weight, for example 1, 2, 3, 4 or 5 mg/kg, but may be as high as 10 mg/kg or even 15 or 20 or 30 mg/kg, e.g., in the ranges 0.1-1 mg/kg, 1-10 mg/kg or 1-20 mg/kg. A fixed unit dose may also be given, for example, 50, 100, 200, 500 or 1000 mg, or the dose may be based on the patient's surface area, e.g., 1000 mg/m$^2$. Usually between 1 and 8 doses, (e.g., 1, 2, 3, 4, 5, 6, 7 or 8) are administered to treat cancer, but 10, 20 or more doses may be given. The mAb can be administered daily, twice per week, weekly, every other week, monthly or at some other interval, depending, e.g. on the half-life of the mAb, for 1 week, 2 weeks, 4 weeks, 6 weeks, 8 weeks, 3-6 months or longer. Repeated courses of treatment are also possible, as is chronic administration.

Diseases especially susceptible to therapy with the mAbs of this invention include those associated with cells such as cancer cells expressing elevated levels of DR4 and/or DR5, compared with normal cells of the same tissue type, for example ovarian cancer, breast cancer, lung cancer (small cell or non-small cell), colon cancer, prostate cancer, pancreatic cancer, gastric cancer, liver cancer (hepatocellular carcinoma), kidney cancer (renal cell carcinoma), head-and-neck tumors, melanoma, sarcomas, and brain tumors (e.g., glioblastomas). Hematologic malignancies such as leukemias and lymphomas may also be susceptible. Optionally expression of DR4 and/or DR5 in cancer cells of a subject being treated can be assessed before initiating or continuing treatment. Expression can be assessed at the mRNA or preferably at the protein level, for example by immune assay of biopsy specimens, such as immunohistochemistry (IHC). Expression of DR4 and/or DR5 is preferably at least above background assessed with an irrelevant control antibody by immune assay and more preferably above the level of noncancerous cells of the same tissue type. Other diseases susceptible to therapy with the mAbs of the invention include autoimmune diseases such as rheumatoid arthritis, multiple sclerosis and inflammatory bowel disease.

In a preferred embodiment, the mAb of the invention is administered in combination with (i.e., together with, that is, before, during or after) other therapy. For example, to treat cancer, the mAb may be administered together with any one or more of the known chemotherapeutic drugs, for example alkylating agents such as carmustine, chlorambucil, cisplatin, carboplatin, oxaliplatin, procarbazine, and cyclophosphamide; antimetabolites such as fluorouracil, floxuridine, fludarabine, gemcitabine, methotrexate and hydroxyurea; natural products including plant alkaloids and antibiotics such as bleomycin, doxorubicin, daunorubicin, idarubicin, etoposide, mitomycin, mitoxantrone, vinblastine, vincristine, and Taxol (paclitaxel) or related compounds such as Taxotere®; the topoisomerase 1 inhibitor irinotecan; and inhibitors of tyrosine kinases such as Gleevec® (imatinib), Sutent® (sunitinib), Nexavar® (sorafenib), Tarceva® (erlotinib), Tykerb® (lapatinib), Iressa® (gefitinib) and Xalkori® (crizotinib); Rapamycin® (sirolimus) and other mTOR inhibitors; and inhibitors of angiogenesis; and all approved and experimental anti-cancer agents listed in WO 2005/017107 A2 (which is herein incorporated by reference). The mAb may be used in combination with 1, 2, 3 or more of these other agents, preferably in a standard chemotherapeutic regimen. Normally, the other agents are those already believed or known to be effective for the particular type of cancer being treated.

Other agents with which the mAb of the invention can be administered to treat cancer include biologics such as monoclonal antibodies, including Herceptin® or Perjeta® (pertuzumab), against the HER2 antigen; Avastin® against VEGF; or antibodies to the Epidermal Growth Factor (EGF) receptor such as Erbitux® (cetuximab) and Vectibix® (panitumumab), activators of the immune system such as Yervoy® (ipilimumab) including anti-PD-1 mAbs such as Opdivo® (nivolurnab) and Keytruda® (pembroluzimab), as well as antibody-drug conjugates such as Kadcyla™ (ado-trastuzumab emtansine). Moreover, the mAb can be used together with any form of surgery and/or radiation therapy.

Treatment (e.g., standard chemotherapy) including the mAb of the invention may increase the median progression-free survival or overall survival time of patients with a particular type of cancer such as those listed above by at least 20% or 30% or 40% but preferably 50%, 60% to 70% or even 100% or longer, compared to the same treatment (e.g., chemotherapy) but without the mAb; or by (at least) 2, 3, 4, 6 or 12 months. In addition or alternatively, treatment (e.g., standard chemotherapy) including the mAb may increase the complete response rate, partial response rate, or objective response rate (complete+partial) of patients (especially when relapsed or refractory) by at least 30% or 40% but preferably 50%, 60% to 70% or even 100% compared to the same treatment (e.g., chemotherapy) but without the mAb.

Typically, in a clinical trial (e.g., a phase II, phase II/III or phase III trial), the aforementioned increases in median progression-free survival and/or response rate of the patients treated with chemotherapy plus the mAb of the invention, relative to the control group of patients receiving chemotherapy alone (or plus placebo), is statistically significant, for example at the p=0.05 or 0.01 or even 0.001 level. It is also understood that response rates are determined by objective criteria commonly used in clinical trials for cancer, e.g., as accepted by the National Cancer Institute and/or Food and Drug Administration, for example the RECIST criteria (Response Evaluation Criteria In Solid Tumors).

5. Other Methods

The mAbs of the invention also find use in diagnostic, prognostic and laboratory methods. They may be used to measure the level of DR4 and/or DR5 in a tumor or in the circulation of a patient with a tumor, and therefore to follow and guide treatment of the tumor. For example, a tumor associated with high levels of DR4 and/or DR5 would be especially susceptible to treatment with the mAb. In particular embodiments, the mAbs can be used in an ELISA or radioimmunoassay to measure the level of DR4 and/or DR5, e.g., in a tumor biopsy specimen or in serum. The use of one anti-DR4 mAb and one anti-DR5 mAb is especially useful to detect cells that express both DR4 and DR5. For various assays, the mAb may be labeled with fluorescent molecules, spin-labeled molecules, enzymes or radioisotopes, and may be provided in the form of kit with all the necessary reagents to perform the assay. In other uses, the mAbs are used to purify DR4 or DR5, e.g., by affinity chromatography.

6. Examples

Example 1: Generation of Anti-DR4 and Anti-DR5 mAbs

To generate and assay mAbs that bind to human DR4, several fusion proteins were constructed using standard methods of molecular biology. To produce DR4-hFc, cDNA encoding the extracellular domain (amino acids 109 to 239) of human DR4 was generated and inserted into derivatives of the pCI vector (Invitrogen), linked to a human Ig gamma-1 Fc region (hinge-cH2-cH3) at the C-terminus, transfected and expressed in 293F mammalian cells. A cynomolgus monkey cDR4-hFc fusion protein was similarly constructed using the monkey DR4 extracellular domain cloned from cynomolgus monkey liver cDNA (Biochain) to obtain the monkey DR4 domain. These Fc-fusion proteins were purified from 293F culture supernatant by using a protein A column. The DR4-KF fusion protein was similarly produced by linking the human DR4 extracellular domain to the human Ig kappa constant region followed by the FLAG peptide (DYKDDDDK, SEQ ID NO:41) at the C-terminus; an analogous protein cDR4-KF was made using cynomolgus monkey DR4. These FLAG-tagged fusion proteins were purified using anti-FLAG columns. To generate and assay mAbs that bind to human DR5, a completely analogous set of proteins DR5-hFc and DR5-KF, and cDR5-hFc and cDR5-KF, were made in the same manner as for DR4 using the human and cynomolgus monkey DR5 extracellular domain (amino acids 54-183) respectively. For blocking assays, human Apo2L/TRAIL protein (amino acids 95-281) was used (R&D systems). Commercial human DR4-Fc and DR5-Fc fusion proteins (R&D systems) were also used.

To generate anti-DR4 mAbs, Balb/c mice were immunized in each hind footpad twice weekly 11 times with 1 µg DR4-hFc (TRAILR1-Fc from R&D Systems) and then 5 times with 5 µg DR4-hFc prepared as described above, resuspended in MPL/TDM adjuvant (Sigma-Aldrich). Three days after the final boost, popliteal lymph node cells were fused with murine myeloma cells, P3X63AgU.1 (ATCC CRL1597), using 35% polyethylene glycol. Hybridomas were selected in HAT medium as described (Chuntharapai and Kim, J Immunol 163:766, 1997). Ten days after the fusion, hybridoma culture supernatants were screened in the DR4 binding ELISA described below. Selected hybridomas were cloned twice by limiting dilution. MAbs in ascites and culture fluids of selected hybridomas were purified using a protein A/G column. Of several antibodies selected for further analysis, the antibody D114 was chosen for development because of its superior agonist activity shown in cell killing assays. The isotype of D114 was determined to be IgG1, kappa using an isotyping kit.

To generate anti-DR5 mAbs, Balb/c mice were immunized in each hind footpad twice weekly 12 times with 5 µg DR5-hFc and then once with 1 µg DR5-hFc resuspended in MPL/TDM adjuvant (Sigma-Aldrich). Three days after the final boost, popliteal lymph node cells were fused with murine myeloma cells and hybridomas selected in HAT medium as described above for anti-DR4 mAbs. Ten days after the fusion, hybridoma culture supernatants were screened in the DR5 binding ELISA described below. Selected hybridomas were then cloned twice by limiting dilution and the mAbs purified as described above for anti-DR4 mAbs. Selected mAbs were further tested for their effects on COLO 205 cell viability and for their binding activity to monkey DR5 as described below. Of several selected antibodies, the antibody G4.2 was chosen for development because of its superior agonist activity shown in cell killing assays. The isotype of G4.2 was determined to be IgG1, kappa using an isotyping kit.

Example 2: Binding and Blocking Activity of Antibodies

Each step of each ELISA assay described in this patent application was performed by room temperature incubation with the appropriate reagent for 1 hour, except the initial plate coating step was done overnight at 4° C. followed by blocking with 2% BSA for 1 hr. Between each step, plates were washed 3 times in PBS containing 0.05% Tween Data points were generally in duplicate or triplicate; there was generally little variability between replicate data points.

To measure binding of mAbs to DR4 (respectively DR5), capture assays were generally used: plates were first coated with goat anti-mouse IgG-Fc (2 µg/mL) overnight, blocked with 2% BSA, incubated with hybridoma supernatant or increasing concentrations of purified antibody to be tested, and then with 0.3 µg/ml of DR4-KF (resp. DR5-KF). The DR4-KF (resp. DR5-KF) captured was detected by addition of HRP-goat anti-human kappa, and then TMB substrate. However, to measure binding of the HuG4.2 variants to DR5 as described below, a direct binding assay was used: plates were coated with Dr5-Fc (0.5 µg/mL), blocked, incubated with increasing concentrations of mAbs, and bound mAb detected with HRP-goat anti-human kappa.

To measure blocking activity of mAbs, plates were first coated with goat anti-human IgG-Fc (2 µg/ml) overnight, blocked with 2% BSA and then incubated with DR4-hFc or resp. DR5-hFc (0.5 µg/ml). Then 50 ng/ml Apo2L (TRAIL, R&D Systems) mixed with various concentrations of purified mAb were added to the wells, and the bound Apo2L was detected by the addition of 0.2 µg/ml of biotinylated anti-TRAIL antibody (R&D Systems), followed by the addition of HRP-Streptavidin and then TMB substrate. Using these ELISA assays, it was shown that D114 binds to DR4 as well as 4H6 does (FIG. 2A), and blocks the binding of Apo2L to DR4 as well as 4H6 does (FIG. 2B). It was similarly shown that D114 binds to cynomolgus monkey DR4 about as well as to human DR4 by using the cDR4-hFc protein in the binding assay. It was also shown that G4.2 binds well to DR5 (FIG. 2C) and effectively blocks the binding of Apo2L to DR5 (FIG. 2D). Moreover, it was shown that G4.2 also binds well to cynomolgus monkey DR5 by using the cDR5-hFc protein in the binding assay described above, whereas 3H3 does not bind to cynomolgus DR5 in this assay, providing an advantage of G4.2 relative to 3H3 and showing that G4.2 must have a different epitope than 3H3.

Example 3: Cell Killing by D114 and G4.2

To perform assays to measure reduction of cell viability (called cell killing herein), human tumor cell lines in DMEM/10% FCS were plated into a 96-well plate at $2 \times 10^4$ cells/100 µl/well and incubated overnight (in standard conditions of 37° C. and 5% $CO_2$). The media was then removed and replaced by 100 µl of the same media containing increasing concentrations of mAb, with or without 10 µg/mL goat anti-mouse IgG-Fc (anti-mIgG-Fc) for mouse antibodies and goat anti-human IgG-Fc (anti-hIgG-Fc) for human, humanized or chimeric antibodies. In certain assays, the mAb and anti-IgG-Fc were instead included in the media when the tumor cells were plated. Each concentration of mAb was done in duplicate. After incubation overnight in standard conditions, the cell viability was determined by the addition of 10 µl/well of WST-8 for 1 hr and measurement of absorbance at OD 450. The purpose of the goat anti-mIgG-Fc or anti-hIgG-Fc used in some experiments was to cross-link (oligomerize) the anti-DR4 or anti-DR5 antibody being tested, thus potentially transmitting a stronger apoptotic signal to the cells. Such cross-linking by anti-IgG-Fc antibody is believed to mimic the cross-linking that occurs when the anti-DR4 or anti-DR5 antibody binds to and is thus linked by white blood cells infiltrating a tumor via FcγR on the surface of such cells.

Using this assay, it was determined that D114 inhibits cell viability of the H460 lung tumor cell line (ATCC HTB-177; FIG. 3A) and the SW480 colon tumor cell line (ATCC CCL-228; FIG. 3B) and other tested cell lines as well as 4H6, in the presence of anti-mIgG-Fc. Similarly, G4.2 inhibits cell viability of H460 cells (FIG. 3C) and COLO 205 colon tumor cells (ATCC CCL-222; FIG. 3D) almost as well as 3H3 does.

Example 4: Construction and Characterization of Antibodies

Cloning of the heavy and light chain variable regions of the mAbs, construction and expression of various mAbs, and introduction of mutations were all performed using standard methods of molecular biology, e.g. as described in U.S. Pat. No. 7,632,926, which is herein incorporated by reference for all purposes. The amino acid sequences of the (mature) heavy and light chain variable regions of 4H6 are shown respectively in FIGS. 4A and 4B and the (mature) heavy and light chain variable regions of 3H3 are shown respectively in FIGS. 4C and 4D. The (mature) heavy and light chain variable regions of D114 are shown respectively in FIGS. 5A and 5B, top lines labeled D114; and the (mature) heavy and light chain variable regions of G4.2 are shown respectively in FIGS. 5C and 5D, top lines labeled G4.2.

In addition, for comparison to the mAbs disclosed herein, several other anti-DR5 mAbs were constructed based on their published sequences: the human mAbs drozitumab (Apomab; FIGS. 17 and 18 of U.S. Pat. No. 8,030,023) and conatumumab (AMG 655; FIG. 19 of WO 2012/106556), and the mouse mAb TRA-8 (FIGS. 23 and 24 of U.S. Pat. No. 7,244,429).

As a convention used herein, the hFc suffix (also written as Fc in certain figures) applied to an antibody means it contains the human gamma-1 constant region with S267E and L328F mutations, the sequence of which is shown as part of FIG. 6A (see legend to FIG. 6A), whereas the hFc suffix means it contains the human gamma-1 constant region without the S267E and L328F mutations (thus having S and L at those amino acid positions). We constructed 3H3-hFc, 4H6-hFc, D114-hFc and G4.2-hFc chimeric antibodies by combining the variable regions of the respective mouse antibodies with a human kappa constant region and human gamma-1 constant region, and the corresponding 3H3-hFc, 4H6-hFc, D114-hFc and G4.2-hFc chimeric antibodies with the human gamma-1 constant region containing the S267E and L328F mutations. For comparison in some experiments, we also constructed the antibody Apomab-hFc by combining the human Apomab variable regions with human gamma-1 constant region containing the S267E and L328F mutations A bispecific antibody B-4H6/3H3-hFc in the Bs (scFv)$_4$-IgG format was constructed: the amino acid sequences of the heavy and light chains of this mAb are shown respectively in FIG. 6A and FIG. 6B, with each mature chain starting at the first amino after the signal peptide. Hence, this mAb has the configuration shown in FIG. 1A with $V_H1$ and $V_L1$ from the 4H6 mAb and $V_H2$ and $V_L2$ from the 3H3 mAb.

Example 5: Cell Killing by Antibodies

The ability of various antibodies described above to kill different cell lines (i.e., reduce cell viability) was tested in the cell killing assay described above. In the absence of anti-hIgG-Fc, neither 3H3-hFc nor 4H6-hFc nor even a combination (mixture) of these two mAbs showed any killing of either the SW480 colon tumor cells (FIG. 7A) or H460 lung tumor cells (FIG. 8A), because without a cross-linking agent to oligomerize the antibodies, they cannot transmit a death signal to the cells. However, 3H3-hFc* and to an even greater extent 4H6-hFc could kill the SW480 cells in the presence of the cross linking agent anti-hIgG-Fc (FIG. 7B); adding 3H3-hFc to 4H6-hFc** did not further increase killing.

To determine whether the antibody forms with mutations would have an advantage in killing tumor cells in the presence of FcγRIIb-expressing cells, peripheral blood mononuclear cells (PBMCs) consisting largely of monocytes and lymphocytes were isolated from human blood using Ficoll-Paque PLUS (GE Healthcare) according to the manufacturer's instructions. The cell viability assays were performed as described above, except the media containing mAbs also contained generally 2×10 5 human PBMCs. In the presence of the PBMCs, 4H6-hFc** in fact killed H460 tumor cells substantially more effectively than 4H6-hFc (FIG. 8B)

We next explored whether two mutations in the human gamma-1 constant region provided greater cell killing activity than a single mutation. We thus constructed the chimeric 4H6-hFc* mAb (denoted by hFc* with a single asterisk) having only the 5267E mutation, rather than the S267E/L328F double mutation in 4H6-hFc**. The cell killing assay described above was used with a fixed concentration of 0.5 µg/mL mAb, 4×10$^4$ COLO 205 tumor cells per well and 4×10$^5$ PBMCs per well from four different human donors, to take into account potential variability of PBMCs. For each of the donors, 4H6-hFc modestly reduced viability of the tumor cells (relative to control hIgG mAb set to 100% viability for each donor), 4H6-hFc* with single mutation reduced viability slightly to significantly more than 4H6-hFc, but 4H6-hFc** reduced viability substantially better than 4H6-hFc* (FIG. 9A), showing the advantage of two mutations that increase binding to FcγRIIb over one such mutation. To determine whether this was also true of other combinations of at least two mutations, we introduced other pairs of mutations into 4H6-hFc according to the following table:

TABLE 1

| Mutation Variants | | | |
|---|---|---|---|
| Designation | 1st mutation | 2nd mutation | 3$^{rd}$ mutation |
| 4H6-hFc** (2) | S267E | L328F | — |
| 4H6-hFc** (3) | S267E | S239D | — |
| 4H6-hFc** (4) | I332E | S239D | — |
| 4H6-hFc*** (5) | I332E | S239D | A330L |

At a fixed antibody concentration of 1 µg/mL and in the presence of human PBMCs, all four variants reduced cell viability approximately equally for COLO 205 cells, MDA-MB-231 cells (ATCC HTB-26) and H460 cells (FIG. 9B), with the greatest effect seen on the COLO 205 cells and only a modest effect seen for H60 under the conditions of the assay. Hence, various combinations of two or more mutations that each increase binding to FcγRIIb are equally suitable to enhance tumor cell killing.

To further explore the advantage of two mutations over one mutation, the ability of 4H6-hFc, 4H6-hFc*, and 4H6-hFc** to kill COLO 205 cells in the presence of PBMCs was tested over a range of antibody concentrations (FIG. 10A). No killing by 4H6-hFc was seen in this experiment, modest killing by 4H6-hFc*, and substantial killing by 4H6-hFc**, again showing the advantage of two over one mutation.

As a final experiment in this regard, the ability of 4H6-hFc, 4H6-hFc*, and 4H6-hFc to inhibit growth of COLO 205 tumor xenografts in mice was compared, using the methods described just below. When 2 mg/kg of each mAb was administered twice per week, 4H6-hFc with two mutations inhibited the xenografts more strongly than either 4H6-Fc or 4H6-Fc* (FIG. 10B) with respectively no and one mutation, consistent with the cell killing results.

Example 6: Ability of Antibodies to Inhibit Growth of Tumor Xenografts

Xenograft experiments were carried out essentially as described previously (Kim et al., Nature 362:841, 1993). Human tumor cells typically grown in complete DMEM medium were harvested in HBSS. Female immunodeficient mice (4-6 weeks old) were injected subcutaneously with 2-10×10$^6$ cells in 0.1-0.2 ml of HBSS, with Matrigel (Corning) in some experiments, in the dorsal areas. When the tumor size reached about 100 mm$^3$, the mice were grouped randomly, and typically 0.5-5 mg/kg of mAbs were administered i.p. once only or once or twice per week in a volume of 0.1 ml. Tumor sizes were determined twice a week by measuring in two dimensions [length (a) and width (b)]. Tumor volume was calculated according to V=ab 2/2 and expressed as mean tumor volume±SEM. The number of mice in each treatment group was typically 5-7 mice. Statistical analysis can be performed, e.g., using Student's t test on the final data point.

We first conducted xenograft experiments to determine whether, consistent with the enhanced cell killing in the presence of PBMCs described above, the hFc forms of anti-DR4 and anti-DR5 mAbs were more effective than the hFc forms in vivo, due to enhanced FcγR binding provided by the mutations in the hFc constant region. Indeed, whereas the anti-DR4 mAb D114-hFc only moderately inhibited growth of COLO 205 xenografts when administered as a single dose of 2 mg/kg, D114-hFc almost completely inhibited the xenografts under these conditions (FIG. 11A). (As described below, very similar results were obtained for inhibition of COLO 205 xenografts by the humanized forms, HuD114-hFc and HuD114-hFc; FIG. 18A). And whereas D114-hFc did not significantly inhibit growth of SW480 colon tumor xenografts when also administered in this manner, D114-hFc moderately inhibited xenograft growth under these conditions (FIG. 11B). Finally, another anti-DR4 mAb 4H6-hFc moderately inhibited growth of COLO 205 xenografts when given at 2 mg/kg twice per week, but 4H6-hFc completely inhibited xenografts under these conditions (FIG. 11C).

Regarding anti-DR5 mAbs, 3H3-Fc did not significantly inhibit growth of COLO 205 xenografts when administered once at 0.5 mg/kg, but 3H3-hFc completely inhibited growth of these xenografts even when given at this very low dose level (FIG. 12A). Similarly, 3H3-Fc only modestly inhibited growth of MIA PaCa-2 (ATCC CRL-1420) pancreatic tumor xenografts when administered once at 1 mg/kg, but 3H3-hFc completely inhibited growth of these xenografts even when given at this very low dose level (FIG. 12B). Analogously, as described below, when administered once at 1 mg/kg, the humanized mAb HuG4.2-hFc inhibited growth of both COLO 205 xenografts and MIA PaCa-2 xenografts better than HuG4.2-hFc did (FIGS. 19A, B). Thus for both anti-DR4 and anti-DR5 mAbs, the hFc forms with mutations were much more effective in vivo than the hFc forms without mutations.

Example 7: Construction and Characterization of Humanized Antibodies

Design, construction, expression and purification of humanized D114 and humanized G4.2 mAbs were all performed using standard methods of molecular biology, e.g. as described in U.S. Pat. No. 7,632,926 for the L2G7 mAb, which is herein incorporated by reference for all purposes. More specifically, to design a humanized D114 (respectively G4.2) mAb, the methods of Queen et al., U.S. Pat. Nos. 5,530,101 and 5,585,089 were generally followed. The human VK sequence AIT38746 and VH sequence AAC18293 (respectively human VK sequence AAQ02698 and VH sequence AAC50998), as shown in FIGS. 5A and 5B (resp. 5C and 5D), bottom lines, were respectively chosen to serve as acceptor sequences for the D114 (resp. G4.2) VL and VH sequences, because they have particularly high framework homology (i.e., sequence identity) to them. A computer-generated molecular model of the D114 (respectively G4.2) variable domain was used to locate the amino acids in the framework that are close enough to the CDRs to potentially interact with them. To design the humanized D114 (respectively G4.2) light and heavy chain variable regions, the CDRs from the mouse D114 (resp. G4.2) mAb were first conceptually grafted into the acceptor framework regions. At framework positions where the computer model suggested significant contact with the CDRs, which may be needed to maintain the CDR conformation, the amino acids from the mouse antibody were substituted for the human framework amino acids.

For D114, such substitutions were made at residues 48 and 71 of the light chain (HuD114-L1), and at residues 48 and 71 of the heavy chain (HuD114-H1) or at these residues plus the additional heavy chain residues 67 and 69 (HuD114-H2). The light and heavy chain V region sequences of humanized D114 are shown in FIGS. 5A and 5B respectively, middle lines labeled HuD114, where they are aligned against the respective D114 donor and human acceptor V regions. The mAbs with the HuD114-L1 light chain and HuD114-H1 or HuD114-H2 heavy chain are respectively designated HuD114 #1 and HuD114 #2. Each of these was made in two forms: HuD114-hFc where the human gamma-1 constant region does not have the S267E and L328F mutations (and thus has S and L at positions 267 and 328), and HuD114-hFc where the constant region does have these mutations. Using the binding assay described above, both HuD114-hFc #1 and HuD114-hFc #2 bind to DR4 as well as the chimeric antibody D114-hFc described above (FIG. 13A), indicating that no affinity was lost during humanization. HuD114-hFc #1 and HuD114-hFc #2 kill COLO 205 cells in the presence of goat anti-hIgG-Fc equally well (FIG. 14A). In an attempt to improve cell killing activity, new versions of the HuD114 light and heavy chain were produced having additional mouse substitutions: HuD114-L2, which contains mouse substitutions at residues 48 and 71 plus 43 and 44, and HuD114-H3, which contains mouse substitutions at residues 48, 67, 69 and 71 plus 91. Six antibodies consisting of all combinations of HuD114-L1 and HuD114-L2 with HuD114-H1, HuD114-H2 and HuD114-H3 were produced, but they all had comparable binding activity and cell killing activity. Hence, HuD114-hFc #2 and HuD114-hFc #2 were used for further studies and are denoted HuD114-hFc and HuD114-hFc** henceforward and in the figures.

The invention also includes variants of these preferred antibodies, for example humanized antibodies comprising a light chain V region with a sequence at least 90, 95, 98 or 99% identical to HuD114-L1 in FIG. 5A and a heavy chain V region with a sequence at least 90, 95, 98 or 99% identical to HuD114-H1 or HuD114-H2 in FIG. 5B. Preferably all CDR residues in such antibodies are those of the donor. Preferably, light chain positions 48 and 71 are occupied by V and Y respectively and heavy chain positions 48 and 71 are occupied by L and A respectively.

Similarly, for G4.2 mouse substitutions were made at residues 4 and 68 of the light chain (HuG4.2-L1) or at these residues plus residue 1 (HuG4.2-L2), and at residues 27, 28, 30 and 93 of the heavy chain (HuG4.2-H1) or at these residues plus residue 47 (HuG4.2-H2). The light and heavy chain V region sequences of HuG4.2 are shown in FIGS. 5C and 5D respectively, middle lines labeled HuG4.2, where they are aligned against the respective G4.2 donor and human acceptor V regions. By combining each of the humanized light chains with each of the humanized heavy chains, four different humanized G4.21 antibodies designated HuG4.2 #1, #2, #3 and #4 were made, as shown in the following table, where the number of substitutions in each chain is given in parentheses. As for HuD114, each of these mAbs was made in two forms: hFc without mutations in the human gamma-1 heavy chain constant region, and hFc** with the mutations S267E and L328F.

TABLE 2

| HuG4.2 Variants | | |
|---|---|---|
| HuG4.2 | Light Chain | Heavy Chain |
| #1 | L1 (2) | H1 (4) |
| #2 | L1 (2) | H2 (5) |
| #3 | L2 (3) | H1 (4) |
| #4 | L2 (3) | H2 (5) |

All four versions of HuG4.2 bound well to DR5, with HuG4.2-hFc #1 and HuG4.2-hFc #2 slightly better than HuG4.2-hFc #3 and HuG4.2-hFc #4 (FIG. 13B). Indeed, HuG4.2-hFc #1 and #2 bound to DR5 comparably to the chimeric antibody G4.2-hFc, indicating that little or no affinity was lost during humanization. All four versions of HuG4.2 also killed COLO 205 cells well in the presence of goat anti-hIgG-Fc (FIG. 14B), with HuG4.2-hFc #2 slightly better than the others and essentially the same as the chimeric antibody G4.2-hFc. Hence, HuG4.2-Fc #2 and HuG4.2-hFc #2 were used for further studies, and are denoted HuG4.2-Fc and HuG4.2-Fc henceforward and in the figures.

The invention also includes variants of HuG4.2 which comprise a light chain V region with a sequence at least 90, 95, 98 or 99% identical to HuG4.2-L1 or HuG4.2-L2 in FIG. 5C and a heavy chain V region with a sequence at least 90, 95, 98 or 99% identical to HuG4.2-H1 or HuG4.2-H2 in FIG. 5D. Preferably all CDR residues in such antibodies are those of the donor antibody. Preferably light chain positions 4 and 68 are occupied by L and R respectively, and heavy chain positions 27, 28, 30 and 93 are occupied by L, P, N and T respectively. Optionally, heavy chain position 47 is occupied by L.

The ability of the various humanized mAbs to kill cells was tested in the presence of goat anti-IgG-Fc (10 µg/mL) as cross-linking agent. Both HuD114-hFc and HuD114-hFc killed COLO 205 colon tumor cells (FIG. 15A) and SW480 colon tumor cells (FIG. 15B) much better than did mapatumumab, the anti-DR4 mAb that has been tested in clinical trials. However, there was no significant difference between HuD114-hFc and HuD114-hFc, as expected because the increase in binding to FcγRIIb provided by the mutations should not have an effect in the absence of FcγRIIb-expressing cells. Similarly, the ability of HuG4.2-hFc and/or HuG4.2-hFc was compared with that of the anti-DR5 mAbs Apomab, AMG 655 and lexatumumab to kill COLO 205 cells (FIG. 15C), and with Apomab and TRA-8 to kill MIA PaCa-2 pancreatic tumor cells (FIG. 15D). Again, where tested, there was no significant difference between HuG4.2-hFc and HuG4.2-hFc because of the absence of FcγRIIb-expressing cells. However, HuG4.2-hFc and HuG4.2-hFc killed both cell lines substantially better than the other tested mAbs, which have been in clinical trials. The ability of various mAbs to kill H460 cells (FIG. 16A) and SW480 cells (FIG. 16B) in the presence of anti-hIgG-Fc was also determined. HuD114-hFc and HuG4.2-hFc killed H460 cells substantially better than the anti-DR5 mAbs Apomab and AMG 655, while HuD114-hFc killed SW480 cells substantially better and HuG4.2-hFc** slightly better than Apomab and AMG655, consistent with the results just noted (FIGS. 15A-D).

Next, we compared the ability of various mAbs to kill cells in the presence of human PBMCs, where the hFc forms might be superior to the hFc forms due to the enhanced FcγRIIb binding provided by the S267E and L328F mutations. Indeed, HuG4.2-Fc killed either COLO 205 cells (FIG. 17A) or H60 cells (FIG. 17B) much better than HuG4.2-Fc, and likewise Apomab-hFc, a form of Apomab in which we introduced these mutations as described above, killed the cells better than Apomab itself (FIG. 17A, B). However, HuG4.2-hFc still killed either COLO 205 or H60 cells substantially better than Apomab-hFc (and better than AMG 655), again showing the superior potency of the HuG4.2-hRFc anti-DR5 mAb.

To compare the effect of two versus one mutation in the context of HuD114 and HuG4.2, we tested the cell-killing ability in the presence of PBMCs of the mAbs HuD114-hFc (respectively HuG4.2-hFc) without mutations, the mAbs HuD114-hFc* (resp. HuG4.2-hFc*) with only the S267E mutation, and the mAbs HuD114-hFc (resp. HuG4.2-hFc) with the S267E/L328F double mutation. HuD114-hFc* killed COLO 205 cells (FIG. 17C) and H460 cells (FIG. 17D) slightly better than HuD114-hFc did, while HuD114-hFc** killed the cells much better. Similarly, HuG4.2-hFc* killed COLO 205 cells (FIG. 17E) and H460 cells (FIG. 17F) slightly better than HuG4.2-hFc did, while HuG4.2-hFc** killed the cells much better. Hence the presence of two mutations in the constant region is substantially advantageous over one mutation.

Turning finally to the ability of the humanized mAbs HuD114 and HuG4.2 to inhibit growth of xenografts, HuD114-hFc moderately inhibited the growth of COLO 205 xenografts when administered once at 2 mg/kg, while HuD114-hFc completely inhibited xenograft growth under these conditions (FIG. 18A). HuD114-hFc given once at 2 mg/kg also strongly inhibited growth the ability of H460 lung tumor xenografts (FIG. 18B). In another experiment, at the low dose tested, HuD114-hFc* completely inhibited growth of COLO 205 xenografts, while the antibody mapatumumab, which has been tested in clinical trials, had no effect (FIG. 18C). When administered once at 2 mg/kg, HuD114-hFc was also somewhat more effective than mapatumumab in inhibiting growth of Ramos (ATCC CRL-1596) lymphoma xenografts (FIG. 18D). A single dose of 1 mg/kg of HuG4.2-hFc or HuG4.2-hFc inhibited growth of COLO 205 xenografts (FIG. 19A) and MIA PaCa-2 pancreatic tumor xenografts (FIG. 19B), with HuG4.2-hFc clearly more effective than HuG4.2-hFc. (HuD114-hFc was also effective in this model; FIG. 19B). Greater efficacy of the hFc forms of these mAbs relative to the hFc forms in xenograft models is consistent with the greater ability of the hFc forms to kill tumor cells in vitro in the presence of PBMCs described above.

Example 8: Characterization of a Bispecific Antibody

To show that the bispecific 6-4H6/3H3-hFc mAb described above (FIGS. 6A, B) can simultaneously bind to DR4 and DR5, plates were first coated overnight with an anti-DR4 mAb (2 µg/ml) that does not compete for binding with 4H6, blocked with 2% BSA and then incubated with DR4-hFc (0.5 µg/ml). Then increasing concentrations of 6-4H6/3H3-hFc mAb were added to the wells, followed by 0.5 µg/ml of DR5-KF. Bound DR5-KF was detected with HRP-anti-Flag M2 (Sigma) and substrate. As only a mAb that can bind to both DR4 (in the form of DR4-hFc) and DR5 (in the form of DR5-KF) will give a positive result in this ELISA assay, the results (FIG. 20A) show that 6-4H6/3H3-hFc has this capability, whereas of course the mAbs 4H6-hFc and 3H3-hFc** do not.

The ability of 6-4H6/3H3-hFc to kill COLO 205 without the cross-linking agent anti-mIgG-Fc was determined. 4H6-hFc was not able to kill the cells in these conditions, while 3H3-hFc exhibited some killing (FIG. 20B). This is due to the fact that COLO 205 cells are very sensitive to death receptor agonists, more so than other cell lines such as H60 and SW480 utilized herein. However, the B-4H6/3H3-hFc bispecific mAb killed the cells substantially better than 3H3-hFc, although the 4H6 component had no cell killing ability on its own (FIG. 20B). In contrast, simply mixing the separate mAbs 3H3-hFc and 4H6-hFc** did not increase the cell killing ability of either one (FIG. 7A, B).

Another bispecific antibody B-HuD114/HuG4.2-hFc was constructed in the Bs(scFv)$_4$-IgG format in the same manner as B-4H6/3H3-hFc, and also containing the double mutation in the constant region. Using the ELISA assay described above in this example, this B-HuD114/HuG4.2-hFc mAb bound to both DR4 and DR5, while HuG4.2-hFC did not (FIG. 20C). A B-HuD114/HuG4.2-hFc** mAb also killed COLO 205 cells in the absence of anti-hIgG-Fc (FIG. 20D), even better than the natural ligand TRAIL did.

Although the invention has been described with reference to the presently preferred embodiments, it should be understood that various modifications can be made without departing from the invention. Unless otherwise apparent from the context any step, element, embodiment, feature or aspect of the invention can be used with any other. All publications, patents and patent applications including accession numbers and the like cited are herein incorporated by reference in their entirety for all purposes to the same extent as if each individual publication, patent and patent application was specifically and individually indicated to be incorporated by reference in its entirety for all purposes. The word "herein" indicates anywhere in this patent application, not merely within the section where the word "herein" occurs. If more than one sequence is associated with an accession number at different times, the sequence associated with the accession number as of the effective filing date of this application is intended, the effective filing date meaning the actual filing date or earlier date of a filing of a priority application disclosing the accession number in question.

We claim:

1. A monoclonal antibody (mAb) that binds to a death receptor 5 and which comprises a light chain variable (V) region having three CDRs from the light chain V region sequence of SEQ ID NO: 12 and a heavy chain V region having three CDRs from the heavy chain V region sequence of SEQ ID NO: 16.

2. The monoclonal antibody of claim 1, wherein the three CDRs of the light chain V region comprise SEQ ID NOS: 26-28 respectively, and the three CDRs of the heavy chain V region comprise SEQ ID NOS:29-31 respectively.

3. The mAb of claim 1 which is a humanized antibody.

4. The mAb of claim 3, which comprises a light chain V region with a sequence at least 90% identical to SEQ ID NO: 13 or SEQ ID NO: 14 and a heavy chain V region with a sequence at last 90% identical SEQ ID NO: 17 or SEQ ID NO: 18, wherein light chain positions 4 and 68 by Kabat numbering are occupied by L and R respectively and heavy chain positions 27, 28, 30 and 93 by Kabat numbering are occupied by L, P, N and T respectively.

5. The mAb of claim 3, which comprises a light chain V region with the sequence of SEQ ID NO: 13 or SEQ ID NO: 14 and a heavy chain V region with the sequence of SEQ ID NO: 17 or SEQ ID NO: 18.

6. The mAb of claim 1, which inhibits growth of a human tumor xenograft in a mouse, wherein the tumor expresses death receptor 5.

7. The mAb of claim 1, which is a bispecific antibody.

8. The mAb of claim 1 comprising a human constant region having one or more mutations that increase binding to a human Fc gamma receptor.

9. The mAb of claim 8, wherein the human constant region is the gamma-1 constant region and the one or more mutations comprise one or both of the S267E and L328F mutations.

10. A pharmaceutical composition comprising the antibody of claim 1 in a pharmaceutically acceptable carrier.

11. A method of treating a patient suffering from a cancer expressing death receptor 5, comprising administering a therapeutically effective dose of the pharmaceutical composition of claim 10.

* * * * *